United States Patent
Tesar et al.

(10) Patent No.: US 10,881,286 B2
(45) Date of Patent: *Jan. 5, 2021

(54) MEDICAL APPARATUS FOR USE WITH A SURGICAL TUBULAR RETRACTOR

(71) Applicant: CAMPLEX, INC., Germantown, TN (US)

(72) Inventors: John Tesar, Tucson, AZ (US); Steven T. Charles, Memphis, TN (US)

(73) Assignee: CamPlex, Inc., Germantown, TN (US)

( * ) Notice: Subject to any disclaimer, the term of this patent is extended or adjusted under 35 U.S.C. 154(b) by 1554 days.

This patent is subject to a terminal disclaimer.

(21) Appl. No.: 14/491,935

(22) Filed: Sep. 19, 2014

(65) Prior Publication Data
US 2015/0141755 A1 May 21, 2015

Related U.S. Application Data

(60) Provisional application No. 61/880,808, filed on Sep. 20, 2013, provisional application No. 61/920,451, (Continued)

(51) Int. Cl.
*A61B 90/50* (2016.01)
*A61B 1/00* (2006.01)
(Continued)

(52) U.S. Cl.
CPC ............ *A61B 1/3132* (2013.01); *A61B 1/005* (2013.01); *A61B 1/00154* (2013.01);
(Continued)

(58) Field of Classification Search
CPC ... A61B 1/3132; A61B 1/00154; A61B 1/005; A61B 1/051; A61B 1/0676; A61B 1/07; A61B 1/0125; A61B 34/20; A61B 90/361; A61B 90/50; A61B 17/0206; A61B 17/0218; A61B 17/1611; A61B 17/3423;
(Continued)

(56) References Cited

U.S. PATENT DOCUMENTS

| 497,064 A | 5/1893 | Van Meter |
| 2,826,114 A | 3/1958 | Bryan |

(Continued)

FOREIGN PATENT DOCUMENTS

| CN | 2336380 Y | 9/1999 |
| CN | 101518438 | 9/2009 |

(Continued)

OTHER PUBLICATIONS

Aesculap Inc.; Aesculap Neurosurgery Pneumatic Kerrison; http://www.aesculapusa.com/assets/base/doc/doc763-pneumatic_kerrison_brochure.pdf; 2008; pp. 12.

(Continued)

*Primary Examiner* — Timothy J Neal
*Assistant Examiner* — William B Chou
(74) *Attorney, Agent, or Firm* — Knobbe, Martens, Olson & Bear, LLP

(57) ABSTRACT

A surgical retractor includes a plurality of cameras integrated therein. One such retractor includes a tubular retractor and an insert supporting said plurality of cameras can be disposed within a tubular retractor.

25 Claims, 33 Drawing Sheets

Related U.S. Application Data filed on Dec. 23, 2013, provisional application No. 61/921,051, filed on Dec. 26, 2013, provisional application No. 61/921,389, filed on Dec. 27, 2013, provisional application No. 61/922,068, filed on Dec. 30, 2013, provisional application No. 61/923,188, filed on Jan. 2, 2014.

(51) Int. Cl.
| | |
|---|---|
| *A61B 34/20* | (2016.01) |
| *A61B 1/313* | (2006.01) |
| *A61B 90/00* | (2016.01) |
| *A61B 17/02* | (2006.01) |
| *G02B 23/24* | (2006.01) |
| *A61B 17/16* | (2006.01) |
| *G02B 17/08* | (2006.01) |
| *G02B 21/36* | (2006.01) |
| *G02B 27/02* | (2006.01) |
| *A61B 1/005* | (2006.01) |
| *A61B 1/05* | (2006.01) |
| *A61B 1/06* | (2006.01) |
| *A61B 1/07* | (2006.01) |
| *A61B 17/34* | (2006.01) |
| *G02B 21/00* | (2006.01) |
| *G02B 21/20* | (2006.01) |
| *A61B 90/30* | (2016.01) |
| *A61B 17/00* | (2006.01) |
| *A61B 50/13* | (2016.01) |
| *G02B 13/06* | (2006.01) |

(52) U.S. Cl.
CPC ............ *A61B 1/051* (2013.01); *A61B 1/0676* (2013.01); *A61B 1/07* (2013.01); *A61B 17/0206* (2013.01); *A61B 17/0218* (2013.01); *A61B 17/1611* (2013.01); *A61B 17/3423* (2013.01); *A61B 34/20* (2016.02); *A61B 90/361* (2016.02); *A61B 90/50* (2016.02); *G02B 17/08* (2013.01); *G02B 21/0012* (2013.01); *G02B 21/20* (2013.01); *G02B 21/361* (2013.01); *G02B 21/362* (2013.01); *G02B 21/367* (2013.01); *G02B 21/368* (2013.01); *G02B 23/2415* (2013.01); *G02B 23/2484* (2013.01); *G02B 27/022* (2013.01); *G02B 27/026* (2013.01); *A61B 1/00045* (2013.01); *A61B 17/3421* (2013.01); *A61B 50/13* (2016.02); *A61B 2017/00535* (2013.01); *A61B 2017/3445* (2013.01); *A61B 2034/2048* (2016.02); *A61B 2034/2051* (2016.02); *A61B 2034/2055* (2016.02); *A61B 2034/2057* (2016.02); *A61B 2090/306* (2016.02); *A61B 2090/371* (2016.02); *G02B 13/06* (2013.01)

(58) Field of Classification Search
CPC .......... A61B 2017/00296; G02B 17/08; G02B 21/0012; G02B 21/20; G02B 21/361; G02B 21/362; G02B 21/367; G02B 21/368; G02B 23/2415; G02B 23/2484; G02B 27/022; G02B 27/026

See application file for complete search history.

(56) References Cited

U.S. PATENT DOCUMENTS

| | | |
|---|---|---|
| 3,050,870 A | 8/1962 | Heilig |
| 3,108,781 A | 10/1963 | Saffir |
| 3,128,988 A | 4/1964 | Mandroian |
| 3,141,650 A | 7/1964 | Saffir |
| 3,405,990 A | 10/1968 | Nothnagle et al. |
| 3,409,346 A | 11/1968 | Stapsy |
| 3,664,330 A | 5/1972 | Deutsch |
| 4,056,310 A | 11/1977 | Shimizu et al. |
| 4,063,557 A | 12/1977 | Wuchinich et al. |
| 4,087,198 A | 5/1978 | Theis, Jr. |
| 4,167,302 A | 9/1979 | Karasawa |
| 4,176,453 A | 12/1979 | Abbott |
| 4,223,676 A | 9/1980 | Wuchinich et al. |
| 4,226,228 A | 10/1980 | Shin et al. |
| 4,344,746 A | 8/1982 | Leonard |
| 4,354,734 A | 10/1982 | Nkahashi |
| 4,395,731 A | 7/1983 | Schoolman |
| 4,562,832 A | 1/1986 | Wilder et al. |
| 4,651,201 A | 3/1987 | Schoolman |
| 4,655,557 A | 4/1987 | Takahashi |
| 4,665,391 A | 5/1987 | Spani |
| 4,684,224 A | 8/1987 | Yamashita et al. |
| 4,703,314 A | 10/1987 | Spani |
| 4,718,106 A | 1/1988 | Weinblatt |
| 4,750,488 A | 6/1988 | Wuchinich et al. |
| 4,750,902 A | 6/1988 | Wuchinich et al. |
| 4,779,968 A | 10/1988 | Sander |
| 4,783,156 A | 11/1988 | Yokota |
| 4,786,155 A | 11/1988 | Fantone et al. |
| 4,813,927 A | 3/1989 | Morris et al. |
| 4,873,572 A | 10/1989 | Miyazaki et al. |
| 4,900,301 A | 2/1990 | Morris et al. |
| 4,905,670 A | 3/1990 | Adair |
| 4,920,336 A | 4/1990 | Meijer |
| 4,922,902 A | 5/1990 | Wuchinich et al. |
| 4,986,622 A | 1/1991 | Martinez |
| 4,989,452 A | 2/1991 | Toon et al. |
| 5,032,111 A | 7/1991 | Morris et al. |
| 5,047,009 A | 9/1991 | Morris et al. |
| 5,098,426 A | 3/1992 | Sklar et al. |
| 5,143,054 A | 9/1992 | Adair |
| 5,151,821 A | 9/1992 | Marks |
| 5,176,677 A | 1/1993 | Wuchinich et al. |
| 5,201,325 A | 4/1993 | McEwen et al. |
| 5,221,282 A | 6/1993 | Wuchinich |
| 5,251,613 A | 10/1993 | Adair |
| 5,327,283 A | 7/1994 | Zobel |
| 5,354,314 A | 10/1994 | Hardy et al. |
| 5,417,210 A | 5/1995 | Funda |
| 5,441,059 A | 8/1995 | Dannan |
| 5,464,008 A | 11/1995 | Kim |
| 5,523,810 A | 6/1996 | Volk |
| 5,537,164 A | 7/1996 | Smith |
| 5,553,995 A | 9/1996 | Martinez |
| 5,575,789 A | 11/1996 | Bell et al. |
| 5,584,796 A | 12/1996 | Cohen |
| 5,593,402 A | 1/1997 | Patrick |
| 5,601,549 A | 2/1997 | Miyagi |
| 5,625,493 A | 4/1997 | Matsumura et al. |
| 5,634,790 A | 6/1997 | Pathmanabhan et al. |
| 5,667,481 A | 9/1997 | Villalta et al. |
| 5,697,891 A | 12/1997 | Hori |
| 5,712,995 A | 1/1998 | Cohn |
| 5,716,326 A | 2/1998 | Dannan |
| 5,743,731 A | 4/1998 | Lares et al. |
| 5,743,846 A | 4/1998 | Takahashi et al. |
| 5,747,824 A | 5/1998 | Jung et al. |
| 5,751,341 A | 5/1998 | Chaleki |
| 5,797,403 A | 8/1998 | DiLorenzo |
| 5,803,733 A | 9/1998 | Trott et al. |
| 5,822,036 A | 10/1998 | Massie et al. |
| 5,825,534 A | 10/1998 | Strahle |
| 5,835,266 A | 11/1998 | Kitajima |
| 5,841,510 A | 11/1998 | Roggy |
| 5,861,983 A | 1/1999 | Twisselman |
| 5,889,611 A | 3/1999 | Zonneveld |
| 5,897,491 A | 4/1999 | Kastenbauer et al. |
| 5,909,380 A | 6/1999 | Dubois |
| 5,913,818 A | 6/1999 | Co et al. |
| 5,928,139 A | 7/1999 | Koros et al. |
| 5,949,388 A | 9/1999 | Atsumi |
| 5,982,532 A | 11/1999 | Mittelstadt et al. |
| 6,016,607 A | 1/2000 | Morimoto et al. |

(56) References Cited

U.S. PATENT DOCUMENTS

| | | |
|---|---|---|
| 6,023,638 A | 2/2000 | Swanson |
| 6,088,154 A | 7/2000 | Morita |
| 6,139,493 A | 10/2000 | Koros et al. |
| 6,152,736 A | 11/2000 | Schmidinger |
| 6,152,871 A | 11/2000 | Foley et al. |
| 6,176,825 B1 | 1/2001 | Chin et al. |
| 6,217,188 B1 | 4/2001 | Wainwright et al. |
| 6,246,898 B1 | 6/2001 | Vesely et al. |
| 6,293,911 B1 | 9/2001 | Imaizumi et al. |
| 6,317,260 B1 | 11/2001 | Ito |
| 6,319,223 B1 | 11/2001 | Wortrich et al. |
| 6,340,363 B1 | 1/2002 | Bolger et al. |
| 6,350,235 B1 | 2/2002 | Cohen et al. |
| 6,354,992 B1 | 3/2002 | Kato |
| 6,398,721 B1 | 6/2002 | Nakamura |
| 6,405,072 B1 | 6/2002 | Cosman |
| 6,434,329 B1 | 8/2002 | Dube et al. |
| 6,443,594 B1 | 9/2002 | Marshall et al. |
| 6,450,706 B1 | 9/2002 | Chapman |
| 6,450,950 B2 | 9/2002 | Irion |
| 6,491,661 B1 | 12/2002 | Boukhny et al. |
| 6,508,759 B1 | 1/2003 | Taylor et al. |
| 6,517,207 B2 | 2/2003 | Chapman |
| 6,525,310 B2 | 2/2003 | Dunfield |
| 6,525,878 B1 | 2/2003 | Takahashi |
| 6,527,704 B1 | 3/2003 | Chang et al. |
| 6,538,665 B2 | 3/2003 | Crow et al. |
| 6,549,341 B2 | 4/2003 | Nomura et al. |
| 6,561,999 B1 | 5/2003 | Nazarifar et al. |
| 6,582,358 B2 | 6/2003 | Akui et al. |
| 6,587,711 B1 | 7/2003 | Alfano et al. |
| 6,589,168 B2 | 7/2003 | Thompson |
| 6,618,207 B2 | 9/2003 | Lei |
| 6,626,445 B2 | 9/2003 | Murphy et al. |
| 6,633,328 B1 | 10/2003 | Byrd et al. |
| 6,635,010 B1 | 10/2003 | Lederer |
| 6,636,254 B1 | 10/2003 | Onishi et al. |
| 6,661,571 B1 | 12/2003 | Shioda et al. |
| 6,668,841 B1 | 12/2003 | Chou |
| 6,698,886 B2 | 3/2004 | Pollack et al. |
| 6,720,988 B1 | 4/2004 | Gere et al. |
| 6,757,021 B1 | 6/2004 | Nguyen-Nhu |
| 6,805,127 B1 | 10/2004 | Karasic |
| 6,817,975 B1 | 11/2004 | Farr et al. |
| 6,824,525 B2 | 11/2004 | Nazarifar et al. |
| 6,847,336 B1 | 1/2005 | Lemelson et al. |
| 6,869,398 B2 | 3/2005 | Obenchain et al. |
| 6,873,867 B2 | 3/2005 | Vilsmeier |
| 6,892,597 B2 | 5/2005 | Tews |
| 6,903,883 B2 | 6/2005 | Amanai |
| 6,908,451 B2 | 6/2005 | Brody et al. |
| 6,985,765 B2 | 1/2006 | Morita |
| 6,996,460 B1 | 2/2006 | Krahnstoever et al. |
| 7,034,983 B2 | 4/2006 | Desimone et al. |
| 7,050,225 B2 | 5/2006 | Nakamura |
| 7,050,245 B2 | 5/2006 | Tesar et al. |
| 7,054,076 B2 | 5/2006 | Tesar et al. |
| 7,116,437 B2 | 10/2006 | Weinstein et al. |
| 7,125,119 B2 | 10/2006 | Farberov |
| 7,150,713 B2 | 12/2006 | Shener et al. |
| 7,150,714 B2 | 12/2006 | Myles |
| 7,154,527 B1 | 12/2006 | Goldstein et al. |
| 7,155,316 B2 | 12/2006 | Sutherland |
| 7,163,543 B2 | 1/2007 | Smedley et al. |
| 7,226,451 B2 | 6/2007 | Shluzas et al. |
| 7,244,240 B2 | 7/2007 | Nazarifar et al. |
| 7,278,092 B2 | 10/2007 | Krzanowski |
| 7,298,393 B2 | 11/2007 | Morita |
| 7,306,559 B2 | 12/2007 | Williams |
| 7,307,799 B2 | 12/2007 | Minefuji |
| 7,326,183 B2 | 2/2008 | Nazarifar et al. |
| 7,471,301 B2 | 12/2008 | Lefevre |
| 7,480,872 B1 | 1/2009 | Ubillos |
| 7,494,463 B2 | 2/2009 | Nehls |
| 7,518,791 B2 | 4/2009 | Sander |
| 7,537,565 B2 | 5/2009 | Bass |
| 7,538,939 B2 | 5/2009 | Zimmerman et al. |
| 7,559,887 B2 | 7/2009 | Dannan |
| 7,621,868 B2 | 11/2009 | Breidenthal et al. |
| 7,633,676 B2 | 12/2009 | Brunner et al. |
| 7,644,889 B2 | 1/2010 | Johnson |
| 7,651,465 B1 | 1/2010 | Sperling et al. |
| 7,713,237 B2 | 5/2010 | Nazarifar et al. |
| 7,764,370 B2 | 7/2010 | Williams et al. |
| 7,766,480 B1 | 8/2010 | Graham et al. |
| 7,777,941 B2 | 8/2010 | Zimmer |
| 7,785,253 B1 | 8/2010 | Arambula |
| 7,786,457 B2 | 8/2010 | Gao |
| 7,806,865 B1 | 10/2010 | Wilson |
| 7,844,320 B2 | 11/2010 | Shahidi |
| 7,872,746 B2 | 1/2011 | Gao et al. |
| 7,874,982 B2 | 1/2011 | Selover |
| 7,896,839 B2 | 3/2011 | Nazarifar et al. |
| 7,907,336 B2 | 3/2011 | Abele et al. |
| 7,927,272 B2 | 4/2011 | Bayer et al. |
| 7,932,925 B2 | 4/2011 | Inbar et al. |
| 7,956,341 B2 | 6/2011 | Gao |
| 8,009,141 B1 | 8/2011 | Chi et al. |
| 8,012,089 B2 | 9/2011 | Bayat |
| 8,018,523 B2 | 9/2011 | Choi |
| 8,018,579 B1 | 9/2011 | Krah |
| 8,027,710 B1 | 9/2011 | Dannan |
| 8,038,612 B2 | 10/2011 | Paz |
| 8,070,290 B2 | 12/2011 | Gille et al. |
| 8,088,066 B2 | 1/2012 | Grey |
| 8,136,779 B2 | 3/2012 | Wilson et al. |
| 8,149,270 B1 | 4/2012 | Yaron et al. |
| 8,159,743 B2 | 4/2012 | Abele et al. |
| 8,169,468 B2 | 5/2012 | Scott et al. |
| 8,187,167 B2 | 5/2012 | Kim |
| 8,187,180 B2 | 5/2012 | Pacey |
| 8,194,121 B2 | 6/2012 | Blumzvig et al. |
| 8,221,304 B2 | 7/2012 | Shioda et al. |
| 8,229,548 B2 | 7/2012 | Frangioni |
| 8,294,733 B2 | 10/2012 | Eino |
| 8,295,693 B2 | 10/2012 | McDowall |
| 8,351,434 B1 | 1/2013 | Fukuda et al. |
| 8,358,330 B2 | 1/2013 | Riederer |
| 8,405,733 B2 | 3/2013 | Saijo |
| 8,408,772 B2 | 4/2013 | Li |
| 8,409,088 B2 | 4/2013 | Grey et al. |
| 8,419,633 B2 | 4/2013 | Koshikawa et al. |
| 8,419,634 B2 | 4/2013 | Nearman et al. |
| 8,430,840 B2 | 4/2013 | Nazarifar et al. |
| 8,439,830 B2 | 5/2013 | McKinley et al. |
| 8,460,184 B2 | 6/2013 | Nearman et al. |
| 8,464,177 B2 | 6/2013 | Ben-Yoseph |
| 8,482,606 B2 | 7/2013 | Razzaque |
| 8,498,695 B2 | 7/2013 | Westwick et al. |
| 8,521,331 B2 | 8/2013 | Itkowitz |
| 8,702,592 B2 | 4/2014 | Langlois et al. |
| 8,702,602 B2 | 4/2014 | Berci et al. |
| 8,734,328 B2 | 5/2014 | McDowall |
| 8,786,946 B2 | 7/2014 | Nakamura |
| 8,827,899 B2 | 9/2014 | Farr et al. |
| 8,827,902 B2 | 9/2014 | Dietze, Jr. et al. |
| 8,836,723 B2 | 9/2014 | Tsao et al. |
| 8,858,425 B2 | 10/2014 | Farr et al. |
| 8,876,711 B2 | 11/2014 | Lin et al. |
| 8,878,924 B2 | 11/2014 | Farr |
| 8,882,662 B2 | 11/2014 | Charles |
| 8,976,238 B2 | 3/2015 | Ernsperger et al. |
| 8,979,301 B2 | 3/2015 | Moore |
| 9,033,870 B2 | 5/2015 | Farr et al. |
| 9,216,068 B2 | 12/2015 | Tesar |
| 9,492,065 B2 | 11/2016 | Tesar et al. |
| 9,615,728 B2 | 4/2017 | Charles et al. |
| 9,629,523 B2 | 4/2017 | Tesar et al. |
| 9,642,606 B2 | 5/2017 | Charles et al. |
| 9,681,796 B2 | 6/2017 | Tesar et al. |
| 9,723,976 B2 | 8/2017 | Tesar |
| 9,782,159 B2 | 10/2017 | Tesar |
| 9,936,863 B2 | 4/2018 | Tesar |
| 10,022,041 B2 | 7/2018 | Charles et al. |

(56) References Cited

U.S. PATENT DOCUMENTS

| | | |
|---|---|---|
| 10,028,651 B2 | 7/2018 | Tesar |
| 10,231,607 B2 | 3/2019 | Charles et al. |
| 10,555,728 B2 | 2/2020 | Charles et al. |
| 10,568,499 B2 | 2/2020 | Tesar |
| 10,702,353 B2 | 7/2020 | Tesar |
| 2001/0055062 A1 | 12/2001 | Shioda et al. |
| 2002/0013514 A1 | 1/2002 | Brau |
| 2002/0049367 A1 | 4/2002 | Irion et al. |
| 2002/0065461 A1 | 5/2002 | Cosman |
| 2002/0082498 A1 | 6/2002 | Wendt et al. |
| 2003/0055410 A1 | 3/2003 | Evans et al. |
| 2003/0059097 A1 | 3/2003 | Abovitz et al. |
| 2003/0078494 A1 | 4/2003 | Panescu et al. |
| 2003/0088179 A1 | 5/2003 | Seeley et al. |
| 2003/0102819 A1 | 6/2003 | Min et al. |
| 2003/0103191 A1 | 6/2003 | Staurenghi et al. |
| 2003/0142204 A1 | 7/2003 | Rus et al. |
| 2003/0147254 A1 | 8/2003 | Yoneda et al. |
| 2004/0017607 A1 | 1/2004 | Hauger et al. |
| 2004/0027652 A1 | 2/2004 | Erdogan et al. |
| 2004/0036962 A1 | 2/2004 | Brunner et al. |
| 2004/0070822 A1 | 4/2004 | Shioda et al. |
| 2004/0087833 A1 | 5/2004 | Bauer et al. |
| 2004/0111183 A1 | 6/2004 | Sutherland |
| 2004/0196553 A1 | 10/2004 | Banju et al. |
| 2004/0230191 A1 | 11/2004 | Frey et al. |
| 2005/0018280 A1 | 1/2005 | Richardson |
| 2005/0019722 A1 | 1/2005 | Schmid et al. |
| 2005/0026104 A1 | 2/2005 | Takahashi |
| 2005/0031192 A1 | 2/2005 | Sieckmann |
| 2005/0033117 A1 | 2/2005 | Ozaki et al. |
| 2005/0052527 A1 | 3/2005 | Remy et al. |
| 2005/0063047 A1 | 3/2005 | Obrebski et al. |
| 2005/0064936 A1 | 3/2005 | Pryor |
| 2005/0065435 A1 | 3/2005 | Rauch et al. |
| 2005/0095554 A1 | 5/2005 | Wilkinson |
| 2005/0107808 A1 | 5/2005 | Evans et al. |
| 2005/0171551 A1 | 8/2005 | Sukovich et al. |
| 2005/0215866 A1 | 9/2005 | Kim |
| 2005/0228232 A1 | 10/2005 | Gillinov et al. |
| 2005/0279355 A1 | 12/2005 | Loubser |
| 2006/0004261 A1 | 1/2006 | Douglas |
| 2006/0020213 A1 | 1/2006 | Whitman et al. |
| 2006/0025656 A1 | 2/2006 | Buckner et al. |
| 2006/0069315 A1 | 3/2006 | Miles et al. |
| 2006/0069316 A1 | 3/2006 | Dorfman et al. |
| 2006/0085969 A1 | 4/2006 | Bennett et al. |
| 2006/0092178 A1 | 5/2006 | Tanguya, Jr. et al. |
| 2006/0114411 A1 | 6/2006 | Wei et al. |
| 2006/0129140 A1 | 6/2006 | Todd et al. |
| 2006/0152516 A1 | 7/2006 | Plummer |
| 2006/0235279 A1 | 10/2006 | Hawkes et al. |
| 2006/0236264 A1 | 10/2006 | Cain et al. |
| 2006/0241499 A1 | 10/2006 | Irion et al. |
| 2006/0276693 A1 | 12/2006 | Pacey |
| 2006/0293557 A1 | 12/2006 | Chuanggui et al. |
| 2007/0010716 A1 | 1/2007 | Malandain |
| 2007/0019916 A1 | 1/2007 | Takami |
| 2007/0038080 A1 | 2/2007 | Salisbury, Jr. et al. |
| 2007/0086205 A1 | 4/2007 | Krupa et al. |
| 2007/0129608 A1 | 6/2007 | Sandhu |
| 2007/0129719 A1* | 6/2007 | Kendale ............ A61B 1/00096 606/41 |
| 2007/0153541 A1 | 7/2007 | Bennett et al. |
| 2007/0173853 A1 | 7/2007 | MacMillan |
| 2007/0238932 A1 | 10/2007 | Jones et al. |
| 2007/0282171 A1 | 12/2007 | Karpowicz et al. |
| 2008/0015417 A1 | 1/2008 | Hawkes et al. |
| 2008/0058606 A1 | 3/2008 | Miles et al. |
| 2008/0081947 A1 | 4/2008 | Irion et al. |
| 2008/0091066 A1 | 4/2008 | Sholev |
| 2008/0094583 A1 | 4/2008 | Williams et al. |
| 2008/0096165 A1 | 4/2008 | Virnicchi et al. |
| 2008/0097467 A1 | 4/2008 | Gruber et al. |
| 2008/0123183 A1 | 5/2008 | Awdeh |
| 2008/0151041 A1 | 6/2008 | Shafer et al. |
| 2008/0183038 A1 | 7/2008 | Tilson et al. |
| 2008/0195128 A1 | 8/2008 | Orbay et al. |
| 2008/0221394 A1 | 9/2008 | Melkent et al. |
| 2008/0221591 A1 | 9/2008 | Farritor et al. |
| 2008/0266840 A1 | 10/2008 | Nordmeyer et al. |
| 2008/0269564 A1 | 10/2008 | Gelnett |
| 2008/0269730 A1 | 10/2008 | Dotson |
| 2008/0278571 A1 | 11/2008 | Mora |
| 2008/0300465 A1 | 12/2008 | Feigenwinter et al. |
| 2008/0303899 A1 | 12/2008 | Berci |
| 2008/0310181 A1 | 12/2008 | Gurevich et al. |
| 2008/0319266 A1 | 12/2008 | Poll et al. |
| 2009/0030436 A1 | 1/2009 | Charles |
| 2009/0034286 A1 | 2/2009 | Krupa et al. |
| 2009/0040783 A1 | 2/2009 | Krupa et al. |
| 2009/0052059 A1 | 2/2009 | Lin |
| 2009/0105543 A1 | 4/2009 | Miller et al. |
| 2009/0137893 A1 | 5/2009 | Seibel et al. |
| 2009/0137989 A1 | 5/2009 | Kataoka |
| 2009/0149716 A1 | 6/2009 | Diao et al. |
| 2009/0156902 A1 | 6/2009 | Dewey et al. |
| 2009/0185392 A1 | 7/2009 | Krupa et al. |
| 2009/0190209 A1 | 7/2009 | Nakamura |
| 2009/0190371 A1 | 7/2009 | Root et al. |
| 2009/0209826 A1 | 8/2009 | Sanders et al. |
| 2009/0238442 A1 | 9/2009 | Upham et al. |
| 2009/0244259 A1 | 10/2009 | Kojima et al. |
| 2009/0245600 A1 | 10/2009 | Hoffman et al. |
| 2009/0248036 A1 | 10/2009 | Hoffman et al. |
| 2009/0258638 A1 | 10/2009 | Lee |
| 2009/0304582 A1 | 12/2009 | Rousso et al. |
| 2009/0318756 A1 | 12/2009 | Fisher et al. |
| 2009/0326322 A1 | 12/2009 | Diolaiti |
| 2009/0326331 A1 | 12/2009 | Rosen |
| 2010/0013910 A1 | 1/2010 | Farr |
| 2010/0013971 A1 | 1/2010 | Amano |
| 2010/0081919 A1 | 4/2010 | Hyde et al. |
| 2010/0107118 A1 | 4/2010 | Pearce |
| 2010/0128350 A1 | 5/2010 | Findlay et al. |
| 2010/0161129 A1 | 6/2010 | Costa et al. |
| 2010/0168520 A1 | 7/2010 | Poll et al. |
| 2010/0182340 A1 | 7/2010 | Bachelder et al. |
| 2010/0198014 A1 | 8/2010 | Poll et al. |
| 2010/0198241 A1 | 8/2010 | Gerrah et al. |
| 2010/0208046 A1 | 8/2010 | Takahashi |
| 2010/0245557 A1 | 9/2010 | Luley, III et al. |
| 2010/0249496 A1 | 9/2010 | Cardenas et al. |
| 2010/0286473 A1 | 11/2010 | Roberts |
| 2010/0305409 A1 | 12/2010 | Chang |
| 2010/0312069 A1 | 12/2010 | Sutherland et al. |
| 2010/0318099 A1 | 12/2010 | Itkowitz et al. |
| 2010/0331855 A1 | 12/2010 | Zhao et al. |
| 2011/0034781 A1 | 2/2011 | Loftus |
| 2011/0038040 A1 | 2/2011 | Abele et al. |
| 2011/0042452 A1 | 2/2011 | Cormack |
| 2011/0046439 A1 | 2/2011 | Pamnani et al. |
| 2011/0063734 A1 | 3/2011 | Sakaki |
| 2011/0065999 A1 | 3/2011 | Manzanares |
| 2011/0071359 A1 | 3/2011 | Bonadio et al. |
| 2011/0080536 A1 | 4/2011 | Nakamura et al. |
| 2011/0115882 A1 | 5/2011 | Shahinian et al. |
| 2011/0115891 A1 | 5/2011 | Trusty |
| 2011/0144436 A1 | 6/2011 | Nearman et al. |
| 2011/0178395 A1 | 7/2011 | Miesner et al. |
| 2011/0184243 A1 | 7/2011 | Wright et al. |
| 2011/0190588 A1 | 8/2011 | McKay |
| 2011/0234841 A1 | 9/2011 | Akeley et al. |
| 2011/0249323 A1 | 10/2011 | Tesar et al. |
| 2011/0257488 A1 | 10/2011 | Koyama et al. |
| 2011/0263938 A1 | 10/2011 | Levy |
| 2011/0264078 A1 | 10/2011 | Lipow et al. |
| 2011/0288560 A1 | 11/2011 | Shohat et al. |
| 2011/0298704 A1 | 12/2011 | Krah |
| 2011/0301421 A1 | 12/2011 | Michaeli et al. |
| 2011/0316994 A1 | 12/2011 | Lemchen |
| 2012/0029280 A1 | 2/2012 | Kucklick |
| 2012/0035423 A1 | 2/2012 | Sebastian et al. |
| 2012/0035638 A1 | 2/2012 | Mathaneswaran et al. |

(56) References Cited

U.S. PATENT DOCUMENTS

| | | |
|---|---|---|
| 2012/0040305 A1 | 2/2012 | Karazivan et al. |
| 2012/0041272 A1 | 2/2012 | Dietze, Jr. et al. |
| 2012/0041534 A1 | 2/2012 | Clerc et al. |
| 2012/0059222 A1 | 3/2012 | Yoshida |
| 2012/0065468 A1 | 3/2012 | Levy et al. |
| 2012/0087006 A1 | 4/2012 | Signaigo |
| 2012/0088974 A1 | 4/2012 | Maurice |
| 2012/0089093 A1 | 4/2012 | Trusty |
| 2012/0097567 A1 | 4/2012 | Zhao et al. |
| 2012/0108900 A1 | 5/2012 | Viola et al. |
| 2012/0116173 A1 | 5/2012 | Viola |
| 2012/0127573 A1 | 5/2012 | Robinson et al. |
| 2012/0130399 A1 | 5/2012 | Moll et al. |
| 2012/0134028 A1 | 5/2012 | Maruyama |
| 2012/0157775 A1 | 6/2012 | Yamaguchi |
| 2012/0157787 A1 | 6/2012 | Weinstein et al. |
| 2012/0157788 A1 | 6/2012 | Serowski et al. |
| 2012/0158015 A1 | 6/2012 | Fowler et al. |
| 2012/0190925 A1 | 7/2012 | Luiken |
| 2012/0197084 A1 | 8/2012 | Drach et al. |
| 2012/0230668 A1 | 9/2012 | Vogt |
| 2012/0232352 A1 | 9/2012 | Lin et al. |
| 2012/0245432 A1 | 9/2012 | Karpowicz et al. |
| 2012/0265023 A1 | 10/2012 | Berci et al. |
| 2012/0320102 A1 | 12/2012 | Jorgensen |
| 2012/0330129 A1 | 12/2012 | Awdeh |
| 2013/0012770 A1 | 1/2013 | Su |
| 2013/0027516 A1 | 1/2013 | Hart et al. |
| 2013/0041226 A1 | 2/2013 | McDowall |
| 2013/0041368 A1 | 2/2013 | Cunningham et al. |
| 2013/0060095 A1 | 3/2013 | Bouquet |
| 2013/0066304 A1 | 3/2013 | Belson et al. |
| 2013/0072917 A1 | 3/2013 | Kaschke et al. |
| 2013/0076863 A1 | 3/2013 | Rappel |
| 2013/0077048 A1 | 3/2013 | Mirlay |
| 2013/0085337 A1 | 4/2013 | Hess et al. |
| 2013/0159015 A1 | 6/2013 | O'Con |
| 2013/0197313 A1 | 8/2013 | Wan |
| 2013/0245383 A1 | 9/2013 | Friedrich et al. |
| 2013/0298208 A1 | 11/2013 | Ayed |
| 2013/0331730 A1 | 12/2013 | Fenech et al. |
| 2014/0005485 A1 | 1/2014 | Tesar et al. |
| 2014/0005486 A1 | 1/2014 | Charles |
| 2014/0005487 A1 | 1/2014 | Tesar |
| 2014/0005488 A1 | 1/2014 | Charles et al. |
| 2014/0005489 A1 | 1/2014 | Charles |
| 2014/0005555 A1 | 1/2014 | Tesar |
| 2014/0081659 A1 | 3/2014 | Nawana et al. |
| 2014/0168785 A1 | 6/2014 | Belgum |
| 2014/0168799 A1 | 6/2014 | Hurbert et al. |
| 2014/0179998 A1 | 6/2014 | Pacey et al. |
| 2014/0187859 A1 | 7/2014 | Leeuw et al. |
| 2014/0198190 A1 | 7/2014 | Okumu |
| 2014/0247482 A1 | 9/2014 | Doi et al. |
| 2014/0275801 A1 | 9/2014 | Menchaca et al. |
| 2014/0276008 A1 | 9/2014 | Steinbach et al. |
| 2014/0285403 A1 | 9/2014 | Kobayashi |
| 2014/0316209 A1 | 10/2014 | Overes et al. |
| 2014/0327742 A1 | 11/2014 | Kiening et al. |
| 2014/0347395 A1 | 11/2014 | Tsao et al. |
| 2014/0362228 A1 | 12/2014 | McCloskey et al. |
| 2014/0378843 A1 | 12/2014 | Valdes et al. |
| 2015/0018622 A1 | 1/2015 | Tesar |
| 2015/0025324 A1 | 1/2015 | Wan |
| 2015/0080982 A1 | 3/2015 | Van Funderburk |
| 2015/0085095 A1 | 3/2015 | Tesar |
| 2015/0087918 A1 | 3/2015 | Vasan |
| 2015/0094533 A1 | 4/2015 | Kleiner et al. |
| 2015/0112148 A1 | 4/2015 | Bouquet |
| 2015/0141759 A1 | 5/2015 | Tesar et al. |
| 2015/0238073 A1 | 8/2015 | Charles |
| 2015/0272694 A1 | 10/2015 | Charles |
| 2015/0297311 A1 | 10/2015 | Tesar |
| 2015/0300816 A1 | 10/2015 | Yang et al. |
| 2016/0018598 A1 | 1/2016 | Hansson |
| 2016/0089026 A1 | 3/2016 | Heerren |
| 2016/0100908 A1 | 4/2016 | Tesar |
| 2016/0139039 A1 | 5/2016 | Ikehara et al. |
| 2016/0220324 A1 | 8/2016 | Tesar |
| 2017/0020627 A1 | 1/2017 | Tesar |
| 2017/0143442 A1 | 5/2017 | Tesar |
| 2017/0258550 A1 | 9/2017 | Vazales |
| 2018/0055348 A1 | 3/2018 | Tesar et al. |
| 2018/0055502 A1 | 3/2018 | Charles et al. |
| 2018/0064316 A1 | 3/2018 | Charles et al. |
| 2018/0064317 A1 | 3/2018 | Tesar |
| 2018/0070804 A1 | 3/2018 | Tesar |
| 2018/0256145 A1 | 9/2018 | Tesar |
| 2018/0318033 A1 | 11/2018 | Tesar |
| 2018/0353059 A1 | 12/2018 | Tesar |
| 2018/0368656 A1 | 12/2018 | Austin et al. |
| 2019/0046021 A1 | 2/2019 | Charles et al. |
| 2019/0053700 A1 | 2/2019 | Tesar |
| 2019/0380566 A1 | 12/2019 | Charles |

FOREIGN PATENT DOCUMENTS

| | | |
|---|---|---|
| CN | 102495463 | 6/2012 |
| CN | 202920720 | 11/2012 |
| DE | 103 41 125 | 4/2005 |
| DE | 10 2010 030 285 | 12/2011 |
| DE | 10 2010 044 502 | 3/2012 |
| EP | 0 293 228 | 11/1988 |
| EP | 0 233 940 | 11/1993 |
| EP | 0 466 705 | 6/1996 |
| EP | 1 175 106 | 1/2002 |
| EP | 1 333 305 | 8/2003 |
| EP | 2 641 561 | 9/2013 |
| JP | 49-009378 | 3/1974 |
| JP | 03-018891 | 1/1991 |
| JP | 06-315487 | 11/1994 |
| JP | 07-194602 | 8/1995 |
| JP | 07-261094 | 10/1995 |
| JP | 08-131399 | 5/1996 |
| JP | 2001-087212 | 4/2001 |
| JP | 2001-117049 | 4/2001 |
| JP | 2001-161638 | 6/2001 |
| JP | 2001-161640 | 6/2001 |
| JP | 2002-011022 | 1/2002 |
| JP | 3402797 | 5/2003 |
| JP | 2003-322803 | 11/2003 |
| JP | 2004-024835 | 1/2004 |
| JP | 3549253 | 8/2004 |
| JP | 2004-305525 | 11/2004 |
| JP | 2007-068876 | 3/2007 |
| JP | 2009-288296 | 12/2009 |
| JP | 4503748 | 7/2010 |
| JP | 2010-206495 | 9/2010 |
| JP | 2011-118741 | 6/2011 |
| WO | WO 87/001276 | 3/1987 |
| WO | WO 91/012034 | 8/1991 |
| WO | WO 99/017661 | 4/1999 |
| WO | WO 00/078372 | 12/2000 |
| WO | WO 01/072209 | 10/2001 |
| WO | WO 2007/047782 | 4/2007 |
| WO | WO 2008/073243 | 6/2008 |
| WO | WO 2009/051013 | 4/2009 |
| WO | WO 2010/079817 | 7/2010 |
| WO | WO 2010/114843 | 10/2010 |
| WO | WO 2010/123578 | 10/2010 |
| WO | WO 2011/069469 | 6/2011 |
| WO | WO 2012/047962 | 4/2012 |
| WO | WO 2012/078989 | 6/2012 |
| WO | WO 2013/049679 | 4/2013 |
| WO | WO 2013/109966 | 7/2013 |
| WO | WO 2013/116489 | 8/2013 |
| WO | WO 2014/004717 | 1/2014 |
| WO | WO 2014/060412 | 4/2014 |
| WO | WO 2014/189969 | 11/2014 |
| WO | WO 2015/042460 | 3/2015 |
| WO | WO 2015/042483 | 3/2015 |
| WO | WO 2015/100310 | 7/2015 |
| WO | WO 2016/090336 | 6/2016 |
| WO | WO 2016/154589 | 9/2016 |

(56) References Cited

FOREIGN PATENT DOCUMENTS

| | | |
|---|---|---|
| WO | WO 2017/091704 | 6/2017 |
| WO | WO 2018/208691 | 11/2018 |
| WO | WO 2018/217951 | 11/2018 |

OTHER PUBLICATIONS

Aliaga, Daniel G.; "Image Morphing and Warping", Department of Computer Science; Purdue University; Spring 2010; in 61 pages.

"Arri Medical Shows SeeFront 3D Display with HD 3D Surgical Microscope", dated Jun. 9, 2013, downloaded from http://www.seefront.com/news-events/article/arri-medical-shows-seefront-3d-display-with-hd-3d-surgical-microscope/.

"Arriscope: A New Era in Surgical Microscopy", Arriscope Brochure published May 20, 2014 in 8 pages.

AustriaMicroSystems; "AS5050: Smallest Magnetic Rotary Encoder for µA Low Power Applications"; www.austriamicrosystems.com/AS5050 printed Nov. 2012 in 2 pages.

Bayonet Lock Video, 00:16 in length, Date Unknown, [Screenshots captured at 00:00, 00:02, 00:05, 00:08, and 00:16].

BellowsTech; "Actuators"; www.bellowstech.com/metal-bellows/actuators/, printed Jul. 17, 2012 in 4 pages.

"Carl Zeiss Unveils $99 VR One Virtual Reality Headset"; www.electronista.com/articles/14/10/10/zeiss.vr.one.able.to.accept.variety.of.smartphones.using.custom.trays printed Oct. 13, 2014 in 2 pages.

Designboom; "Bright LED"; http://www.designboom.com/project/fiber-optics-light-glove/; Sep. 28, 2007.

Fei-Fei, Li; Lecture 10: Multi-View Geometry; Stanford Vision Lab; Oct. 24, 2011; pp. 89.

"Fuse™, Full Spectrum Endoscopy™"; http://www.endochoice.com/Fuse printed Oct. 7, 2013 in 3 pages.

Hardesty, Larry; "3-D Cameras for Cellphones: Clever math could enable a high-quality 3-D camera so simple, cheap and power-efficient that it could be incorporated into handheld devices"; MIT News Office; http://web.mit.edu/newsoffice/2011/lidar-3d-camera-cellphones-0105.html; Jan. 5, 2012; pp. 4.

Hartley et al.; "Multiple View Geometry in Computer Vision: Chapter 9—Epipolar Geometry and the Fundamental Matrix"; http://www.robots.ox.ac.uk/~vgg/hzbook/hzbook2/HZepipolar.pdf; Mar. 2004; 2nd Edition; Ch. 9; pp. 239-261.

Heidelberg Engineering; "MultiColor: Scanning Laser Imaging"; htto://www.heidelbergengineering.com/us/products/spectralis-models/imaging-modes/multicolor/; Copyright © 2013; printed Apr. 5, 2013.

Krishna, Golden; "Watch: What Good is a Screen?" http://www.cooper.com/author/golden_krishna as printed Jul. 9, 2014 in 62 pages.

Lang et al.; "Zeiss Microscopes for Microsurgery"; Springer-Verlag; Berlin, Heidelberg; 1981.

"Leica Microsystems and TrueVision® 3D Surgical create the first 3D digital hybrid microscope", Press Release, Oct. 5, 2012, pp. 2.

Male Bayonet Video, 00:04 in length, Date Unknown, [Screenshots captured at 00:00, 00:01, 00:02, 00:03, and 00:04].

Melexis; "MLX75031 Optical Gesture and Proximity Sensing IC"; httg://melexis.com/optical-sensors/optical-sensing.mlx75031-815.aspx?sta printed Mar. 15, 2013 in 1 page.

MMR Technologies; "Micro Miniature Refrigerators"; www.mmr-tech.com/mmr_overview.php; Copyright © 2011; printed Feb. 11, 2013.

Moog; "Surgical Handpieces: Therapeutic Ultrasonic Devices"; http://www.moog.com/products/surgical-hpieces/ printed Sep. 25, 2013 in 1 page.

Morita; "TwinPower Turbine® High Speed Handpieces Standard, 45°, and Ultra Series Head Designs"; J. Morita Mfg. Corp., http://www.morita.com/usa/root/img/pool/pdf/product_brochures/twinpower_brochure_1-264_0512_web.pdf; May 2012; pp. 20.

Olympus; "Olympus Introduces the World's First and Only Monopolar, Disposable Tonsil Adenoid Debrider (DTAD)"; htto://www.olympusamerica.com/corporate/corp_presscenter_headline.asp?pressNo=926; Sep. 11, 2012; pp. 2.

OmniVision; "OV2722 full HD (1080p) product brief: ⅙-Inch Native 1080p HD CameraChip Sensor for Ultra-Compact Applications"; http://web.archive.org/web/20120730043057/http://www.ovt.com/download_document.php?type=sensor&sensorid=119; May 2012 in 2 pages.

Orthofix; "ProView MAP System Retractors"; www.us.orthofix.com/products/proviewretractors.asp?cid=39; Copyright © 2010; printed Apr. 1, 2013.

OrtusTech; "Sample Shipment Start: World's Smallest Size Full-HD Color TFT LCD"; http://ortustech.co.jp/english/notice/20120427.html printed May 22, 2012 in 2 pages.

Saab, Mark; "Applications of High-Pressure Balloons in the Medical Device Industry"; http://www.ventionmedical.com/documents/medicalballoonpaper.pdf; Copyright © 1999; pp. 19.

Purcher, Jack, "Apple Wins a Patent for an Oculus Rift-Like Display System," http://www.patentlyapple.com/patently-apple/2014/09/apple-wins-a-patent-for-an-oculus-rift-like-display-system.html, Sep. 9, 2014.

Savage, Lynn; "Sound and Light, Signifying Improved Imaging"; www.photonics.com/Article.aspx?AID=45039; Nov. 1, 2010; pp. 6.

Timm, Karl Walter; "Real-Time View Morphing of Video Streams"; University of Illinois; Chicago, Illinois; 2003; pp. 168.

Whitney et al.; "Pop-up book MEMS"; Journal of Micromechanics and Microengineering; Oct. 14, 2011; vol. 21; No. 115021; pp. 7.

Wikipedia, "Zoom Lens," http://en.wikipedia.org/wiki/Optical_Zoom, printed Oct. 7, 2014 in 3 pages.

Zeiss; "Informed for Medical Professionals, Focus: Fluorescence"; Carl Zeiss; 2nd Issue; Oct. 2006; 30-801-LBW-GFH-X-2006; Printed in Germany; pp. 32.

Zeiss; "Ophthalmic Surgery in Its Highest Form, OPMI® Visu 210"; Carl Zeiss, 2005, 30-097/III-e/USA Printed in Germany AW-TS-V/2005 Uoo; pp. 19.

Zeiss; "SteREO Discovery. V12, Expanding the Boundaries"; Carl Zeiss, Sep. 2004; 46-0008 e09.2004, pp. 6.

Zeiss; "Time for a Change: OPMI® pico for ENT"; Carl Zeiss, 2005, 30-451/III-e Printed in Germany LBW-TS-V/2005 Uoo, pp. 8.

Zhang, Michael; "LIFX: A WiFi-Enabled LED Bulb that May Revolutionize Photographic Lighting"; http://www.petapixel.com/2012/09/22/lifx-a-wifi-enabled-led-buib-that-may-revolutionize-photographic-lighting/ printed Sep. 28, 2012 in 9 pages.

Restriction Requirement in U.S. Appl. No. 13/802,362, dated Oct. 23, 2013.

Office Action in U.S. Appl. No. 13/802,362, dated Dec. 17, 2013.

Office Action in U.S. Appl. No. 13/802,362, dated Apr. 7, 2014.

International Search Report and Written Opinion in PCT Application No. PCT/US2013/047972, dated Jan. 3, 2014.

Office Action in U.S. Appl. No. 13/802,485, dated Jun. 20, 2014.

Restriction Requirement in U.S. Appl. No. 13/802,635, dated May 28, 2014.

Office Action in U.S. Appl. No. 13/802,509, dated Sep. 9, 2013.

Notice of Allowance in U.S. Appl. No. 13/802,509, dated Apr. 16, 2014.

Restriction Requirement in U.S. Appl. No. 13/802,582, dated Oct. 23, 2013.

Office Action in U.S. Appl. No. 13/802,582, dated Dec. 16, 2013.

Office Action in U.S. Appl. No. 13/802,582, dated Apr. 16, 2014.

International Search Report and Written Opinion in PCT Application No. PCT/US2014/038839, dated Oct. 17, 2014.

International Search Report and Written Opinion in PCT Application No. PCT/US2014/056643, dated Dec. 11, 2014.

Kramer, Jennifer; "The Right Filter Set Gets the Most out of a Microscope"; Biophotonics International; Jan./Feb. 1999; vol. 6; pp. 54-58.

Leica Microsystems; "Images TrueVision Integrated 3D"; http://www.leica-microsystems.com/products/surgical-mcroscopes/neurosurgery-spine/details/product/truevison-integrated-3d/gallery/; Nov. 26, 2014; in 3 pages.

Leica Microsystems; "Leica Microsystems' Ophthalmic Surgical Microscopes with TrueVision 3D Technology Available Globally";

(56) References Cited

OTHER PUBLICATIONS http://www.leica-microsystems.com/products/surgical-microscopes/neurosurgery-spine/details/product/truevision-integrated-3d/news/; Sep. 18, 2014; in 5 pages.
Lutze et al.; "Microsystems Technology for Use in a Minimally Invasive Endoscope Assisted Neurosurgical Operating System—MINOP II"; 2005; http://web.archive.org/web/20151120215151/http://www.meditec.hia.rwth-aachen.de/fileadmin/content/meditec/bilder/forschung/aktuelle_projekte/robotische/Exoscope_Aesculap.pdf; Nov. 20, 2015 in 4 pages.
MediTec; "MINOP II—Robotical Microscope Platform"; http://web.archive.org/web/20151120213932/http://www.meditec.hia.rwth-aachen.de/en/research/former-projects/minop-ii/; Nov. 20, 2015 in 3 pages.
"Narrow Band Imaging"; http://web.archive.org/web/20150701233623/https://en.wikipedia.org/wiki/Narrow_band_imaging printed Jul. 1, 2015 in 1 page.
Rustum, Dr. Abu; "ICG Mapping Endometrial Cancer"; Pinpoint Endometrium Ca Lenfedenektomi MSKCC May 2013; Memorial Sloan Kettering Cancer Center; May 2013; Published to YouTube.com Sep. 1, 2013; in 2 pages; http://web.archive.org/web/20150402210857/https://www.youtube.com/watch?v-DhChvaUCe4I.
Sun et al.; "Neurotoxin-Directed Synthesis and in Vitro Evaluation of Au Nanoclusters"; RSC Advances, 2015; vol. 5, No. 38; pp. 29647-29652.
TrueVision Microscopes; http://truevisionmicroscopes.com/images/productsnew/081a-f.jpg; printed Nov. 26, 2014 in 1 page.
TrueVision; "About TrueVision"; http://web.archive.org/web/20071208125103/http://www.truevisionsys.com/about.html; as viewed Dec. 8, 2007 in 2 pages.
TrueVision; "TrueVision Technology"; http://web.archive.org/web/20071208125125/http://www.truevisionsys.com/technology.html; as viewed Dec. 8, 2007 in 2 pages.
Zeiss; "Stereomicroscopes: Stemi SV 6, SV 11, SV 11 Apo"; the Profile; 1999; in 30 pages.
Zhang, Sarah; "The Obscure Neuroscience Problem That's Plaguing VR"; http://web.archive.org/web/20150812172934/http://www.wired.com/2015/08/obscure-neuroscience-problem-thats-plaguing-vr/; Aug. 11, 2015 in 5 pages.
Preliminary Amendment in U.S. Appl. No. 14/411,068, dated Aug. 13, 2015.
Office Action in U.S. Appl. No. 14/411,068, dated Aug. 17, 2017.
Official Communication in European Application No. 13808996.6, dated Jan. 4, 2016.
Official Communication in European Application No. 13808996.6, dated Apr. 14, 2016.
Official Communication in European Application No. 13808996.6, dated Feb. 21, 2017.
Official Communication in European Application No. 13808996.6, dated Jun. 6, 2017.
Official Communication in Japanese Application No. 2015-520471, dated May 9, 2017.
Official Communication in Japanese Application No. 2015-520471, dated Nov. 21, 2017.
International Preliminary Report on Patentability in PCT Application No. PCT/US2013/047972, dated Jan. 8, 2015.
Office Action in U.S. Appl. No. 13/802,635, dated Mar. 27, 2015.
Final Office Action in U.S. Appl. No. 13/802,635, dated Jan. 14, 2016.
Response to Final Office Action in U.S. Appl. No. 13/802,635, dated Jul. 13, 2016.
Office Action in U.S. Appl. No. 13/802,635, dated Sep. 27, 2016.
Amendment and Response to Office Action in U.S. Appl. No. 13/802,635, dated Mar. 24, 2017.
Notice of Allowance in U.S. Appl. No. 13/802,635, dated Apr. 27, 2017.
Notice of Allowance in U.S. Appl. No. 13/802,635, dated Aug. 15, 2017.
Amendment in U.S. Appl. No. 15/589,058, dated Nov. 15, 2017.
Office Action in U.S. Appl. No. 15/589,058, dated Dec. 8, 2017.
Office Action in U.S. Appl. No. 13/802,577, dated Sep. 30, 2016.
Response to Office Action in U.S. Appl. No. 13/802,577, dated Mar. 29, 2017.
Notice of Allowance in U.S. Appl. No. 13/802,577, dated Apr. 24, 2017.
Amendment in U.S. Appl. No. 13/802,577, dated May 25, 2017.
Office Action in U.S. Appl. No. 13/802,577, dated Jun. 20, 2017.
Amendment in U.S. Appl. No. 13/802,577, dated Nov. 20, 2017.
Notice of Allowance in U.S. Appl. No. 13/802,577, dated Dec. 6, 2017.
Official Communication in European Application No. 14800423.7, dated Feb. 8, 2017.
International Preliminary Report on Patentability in PCT Application No. PCT/US2014/038839, dated Dec. 3, 2015.
Preliminary Amendment in U.S. Appl. No. 14/491,827, dated Nov. 25, 2014.
Office Action in U.S. Appl. No. 14/491,827, dated Mar. 1, 2017.
Amendment in U.S. Appl. No. 14/491,827, dated Aug. 1, 2017.
Notice of Allowance in U.S. Appl. No. 14/491,827, dated Sep. 25, 2017.
Partial Supplementary European Search Report in European Application No. 14845427.5, dated May 4, 2017.
Extended European Search Report in European Application No. 14845427.5, dated Aug. 8, 2017.
European Search Report in European Application No. 14846410.0, dated Jun. 23, 2017.
International Preliminary Report on Patentability and Written Opinion in PCT Application No. PCT/US2014/056643, dated Mar. 31, 2016.
Invitation to Pay Additional Fees in PCT Application No. PCT/US2014/056681, dated Jan. 14, 2015.
International Search Report and Written Opinion in PCT Application No. PCT/US2014/056681, dated Mar. 20, 2015.
International Preliminary Report on Patentability and Written Opinion in PCT Application No. PCT/US2014/056681, dated Mar. 31, 2016.
Preliminary Amendment in U.S. Appl. No. 14/581,779, dated Jul. 6, 2015.
Restriction Requirement in U.S. Appl. No. 14/581,779, dated Oct. 31, 2017.
Extended European Search Report in European Application No. 14873324.9, dated Aug. 25, 2017.
Invitation to Pay Additional Fees in PCT Application No. PCT/US2014/072121, dated Mar. 2, 2015.
International Search Report and Written Opinion in PCT Application No. PCT/US2014/072121, dated May 1, 2015.
International Preliminary Report on Patentability and Written Opinion in PCT Application No. PCT/US2014/072121, dated Jul. 7, 2016.
Preliminary Amendment in U.S. Appl. No. 14/960,276, dated Apr. 18, 2016.
Office Action in U.S. Appl. No. 14/960,276, dated Jul. 28, 2017.
International Search Report and Written Opinion in PCT Application No. PCT/US2015/064133, dated Feb. 9, 2016.
International Preliminary Report on Patentability and Written Opinion in PCT Application No. PCT/US2015/064133, dated Jun. 15, 2017.
Preliminary Amendment in U.S. Appl. No. 15/081,653, dated Oct. 11, 2016.
International Search Report and Written Opinion in PCT Application No. PCT/US2016/024330, dated Jul. 1, 2016.
International Preliminary Report on Patentability and Written Opinion in PCT Application No. PCT/US2016/024330, dated Oct. 5, 2017.
Preliminary Amendment in U.S. Appl. No. 15/360,565, dated Feb. 6, 2017.
Invitation to Pay Additional Fees in PCT Application No. PCT/US2016/063549, dated Feb. 2, 2017.
International Search Report and Written Opinion in PCT Application No. PCT/US2016/063549, dated Apr. 14, 2017.

(56) References Cited

OTHER PUBLICATIONS

"Portion"; Definition; American Heritage® Dictionary of the English Language; Fifth Edition; 2016; Retrieved Apr. 12, 2018 from https://www.thefreedictionary.com/portion in 1 page.
Preliminary Amendment in U.S. Appl. No. 16/357,081, dated Sep. 4, 2019.
Official Communication in European Application No. 13808996.6, dated Jun. 15, 2018.
Official Communication in European Application No. 13808996.6, dated May 13, 2019.
Notice of Decision or Rejection in Japanese Application No. 2015-520471, dated Jul. 24, 2018.
Preliminary Amendment in U.S. Appl. No. 15/483,995, dated Nov. 21, 2017.
Office Action in U.S. Appl. No. 15/483,995, dated Mar. 9, 2018.
Amendment in U.S. Appl. No. 15/483,995, dated Sep. 7, 2018.
Final Office Action in U.S. Appl. No. 15/483,995, dated Nov. 29, 2018.
Amendment in U.S. Appl. No. 15/483,995, dated May 28, 2019.
Office Action in U.S. Appl. No. 15/483,995, dated Jun. 13, 2019.
Office Action in U.S. Appl. No. 15/645,589, dated Feb. 9, 2018.
Amendment in U.S. Appl. No. 15/645,589, dated Aug. 7, 2018.
Final Office Action in U.S. Appl. No. 15/645,589, dated Nov. 28, 2018.
Amendment in U.S. Appl. No. 15/645,589, dated May 28, 2019.
Office Action in U.S. Appl. No. 15/645,589, dated Jun. 13, 2019.
Preliminary Amendment filed in U.S. Appl. No. 16/036,665, dated Nov. 1, 2018.
Preliminary Amendment filed in U.S. Appl. No. 16/036,665, dated Sep. 5, 2019.
Office Action in U.S. Appl. No. 16/036,665, dated Sep. 26, 2019.
Office Action in U.S. Appl. No. 15/626,516, dated Mar. 14, 2018.
Amendment in U.S. Appl. No. 15/626,516, dated Sep. 13, 2018.
Final Office Action in U.S. Appl. No. 15/626,516, dated Jan. 15, 2019.
Response in U.S. Appl. No. 15/626,516, dated Jul. 15, 2019.
Restriction Requirement in U.S. Appl. No. 15/495,484, dated May 14, 2019.
Amendment in U.S. Appl. No. 15/589,058, dated Jun. 7, 2018.
Final Office Action in U.S. Appl. No. 15/589,058, dated Aug. 27, 2018.
Amendment in U.S. Appl. No. 15/589,058, dated Feb. 26, 2019.
Office Action in U.S. Appl. No. 15/589,058, dated Mar. 5, 2019.
Amendment in U.S. Appl. No. 15/589,058, dated Sep. 5, 2019.
Notice of Allowance in U.S. Appl. No. 15/589,058, dated Sep. 25, 2019.
Preliminary Amendment filed in U.S. Appl. No. 15/724,100, dated Jun. 5, 2018.
Office Action in U.S. Appl. No. 15/724,100, dated Oct. 9, 2019.
Preliminary Amendment in U.S. Appl. No. 16/042,318, dated Nov. 8, 2018.
Office Action in U.S. Appl. No. 16/042,318, dated May 8, 2019.
Amendment in U.S. Appl. No. 16/042,318, dated Sep. 9, 2019.
Notice of Allowance in U.S. Appl. No. 16/042,318, dated Oct. 9, 2019.
Official Communication in European Application No. 14846410.0, dated Jul. 18, 2018.
Official Communication in European Application No. 14846410.0, dated Mar. 20, 2019.
Official Communication in Japanese Application No. 2016-544032, dated Jun. 26, 2018.
Restriction Requirement and Election of Species Response in U.S. Appl. No. 14/581,779, dated Jan. 2, 2018.
Office Action in U.S. Appl. No. 14/581,779, dated Apr. 24, 2018.
Amendment in U.S. Appl. No. 14/581,779, dated Sep. 24, 2018.
Final Office Action in U.S. Appl. No. 14/581,779, dated Jan. 4, 2019.
Amendment in U.S. Appl. No. 14/581,779, dated Jul. 2, 2019.
Office Action in U.S. Appl. No. 14/581,779, dated Aug. 5, 2019.
Official Communication in Japanese Application No. 2016-542194, dated Nov. 6, 2018.
Decision of Rejection in Japanese Application No. 2016-542194, dated May 14, 2019.
Amendment in U.S. Appl. No. 14/960,276, dated Jan. 26, 2018.
Office Action in U.S. Appl. No. 14/960,276, dated Mar. 8, 2018.
Amendment in U.S. Appl. No. 14/960,276, dated Sep. 7, 2018.
Office Action in U.S. Appl. No. 14/960,276, dated Nov. 2, 2018.
Amendment in U.S. Appl. No. 14/960,276, dated May 2, 2019.
Final Office Action in U.S. Appl. No. 14/960,276, dated Jun. 7, 2019.
Extended European Search Report in European Application No. 15865454.1, dated Jun. 27, 2018.
Office Action in U.S. Appl. No. 15/081,653, dated Mar. 28, 2018.
Amendment in U.S. Appl. No. 15/081,653, dated Sep. 27, 2018.
Final Office Action in U.S. Appl. No. 15/081,653, dated Nov. 16, 2018.
Final Amendment in U.S. Appl. No. 15/081,653, dated May 15, 2019.
Office Action in U.S. Appl. No. 15/081,653, dated Jul. 12, 2019.
Extended European Search Report in European Application No. 16769809.1, dated Nov. 23, 2018.
Office Action in U.S. Appl. No. 15/360,565, dated Aug. 10, 2018.
Amendment in U.S. Appl. No. 15/360,565, dated Feb. 8, 2019.
Office Action in U.S. Appl. No. 15/360,565, dated May 22, 2019.
Extended European Search Report in European Application No. 16869253.1, dated May 29, 2019.
International Preliminary Report on Patentability and Written Opinion in PCT Application No. PCT/US2016/063549, dated Jun. 7, 2018.
Office Action in U.S. Appl. No. 15/973,433, dated Jun. 28, 2019.
International Search Report and Written Opinion in PCT Application No. PCT/US2018/031442, dated Sep. 14, 2018.
International Search Report and Written Opinion in PCT Application No. PCT/US2018/034227, dated Jul. 30, 2018.
Office Action in U.S. Appl. No. 16/357,081, dated Jul. 8, 2020.
Official Communication in Japanese Application No. 2018-218745, dated Feb. 25, 2020.
Amendment in U.S. Appl. No. 15/483,995, dated Dec. 12, 2019.
Final Office Action in U.S. Appl. No. 15/483,995, dated Feb. 20, 2020.
Office Action in U.S. Appl. No. 15/645,589, dated Dec. 26, 2019.
Amendment in U.S. Appl. No. 15/645,589, dated Jun. 26, 2020.
Notice of Allowance in U.S. Appl. No. 15/645,589, dated Jul 14, 2020.
Amendment filed in U.S. Appl. No. 16/036,665, dated Mar. 26, 2020.
Office Action in U.S. Appl. No. 16/036,665, dated Jul. 13, 2020.
Amendment in U.S. Appl. No. 15/626,516, dated Jan. 24, 2020.
Notice of Allowance in U.S. Appl. No. 15/626,516, dated Mar. 9, 2020.
Notice of Allowance in U.S. Appl. No. 15/626,516, dated Jun. 29, 2020.
Response to Restriction Requirement in U.S. Appl. No. 15/495,484, dated Nov. 13, 2019.
Office Action in U.S. Appl. No. 15/495,484, dated Nov. 27, 2019.
Amendment in U.S. Appl. No. 15/495,484, dated May 27, 2020.
Notice of Allowance in U.S. Appl. No. 15/495,484, dated Jun. 16, 2020.
Restriction Requirement in U.S. Appl. No. 15/948,842, dated Jan. 22, 2020.
Amendment filed in U.S. Appl. No. 15/724,100, dated Apr. 9, 2020.
Office Action in U.S. Appl. No. 15/724,100, dated Apr. 22, 2020.
Notice of Allowance in U.S. Appl. No. 15/724,100, dated Jul. 6, 2020.
Amendment in U.S. Appl. o. 14/581,779, dated Feb. 4, 2020.
Final Office Action in U.S. Appl. No. 14/581,779, dated Apr. 29, 2020.
Amendment in U.S. Appl. No. 15/081,653, dated Jan. 10, 2020.
Final Office Action in U.S. Appl. No. 15/081,653, dated Jan. 31, 2020.
Amendment in U.S. Appl. No. 15/081,653, dated Jul. 30, 2020.
Amendment in U.S. Appl. No. 15/360,565, dated Nov. 21, 2019.

(56) References Cited

OTHER PUBLICATIONS

Office Action in U.S. Appl. No. 15/360,565, dated Jan. 30, 2020.
Amendment in U.S. Appl. No. 15/360,565, dated Jul. 29, 2020.
Amendment in U.S. Appl. No. 15/973,433, dated Sep. 30, 2019.
Notice of Allowance in U.S. Appl. No. 15/973,433, dated Jan. 28, 2020.
Notice of Allowance in U.S. Appl. No. 15/973,433, dated Jun. 25, 2020.
International Preliminary Report on Patentability and Written Opinion in PCT Application No. PCT/US2018/031442, dated Nov. 21, 2019.
International Preliminary Report on Patentability and Written Opinion in PCT/US2018/034227, dated Dec. 5, 2019.

* cited by examiner

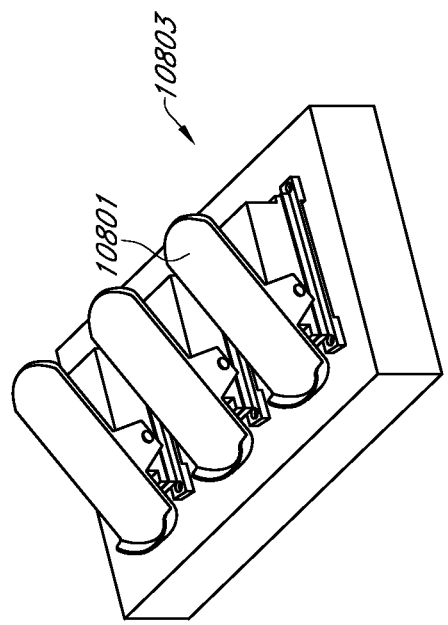
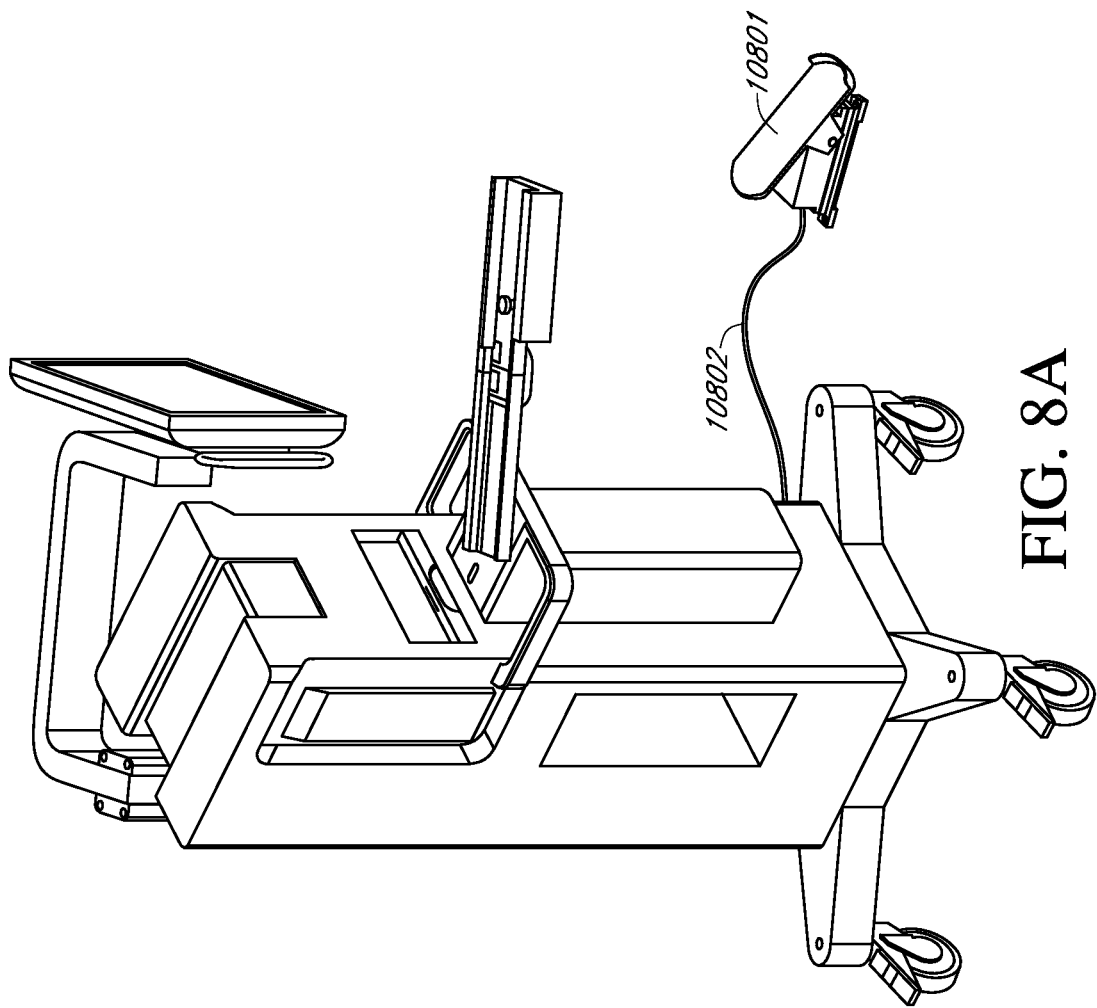
FIG. 8B
FIG. 8A

MEDICAL APPARATUS FOR USE WITH A SURGICAL TUBULAR RETRACTOR

RELATED APPLICATIONS

This application claims the benefit of priority to U.S. Prov. App. No. 61/880,808, entitled "SURGICAL VISUALIZATION SYSTEMS", filed Sep. 20, 2013; to U.S. Prov. App. No. 61/920,451, entitled "SURGICAL VISUALIZATION SYSTEMS", filed Dec. 23, 2013; to U.S. Prov. App. No. 61/921,051, entitled "SURGICAL VISUALIZATION SYSTEMS", filed Dec. 26, 2013; to U.S. Prov. App. No. 61/921,389, entitled "SURGICAL VISUALIZATION SYSTEMS", filed Dec. 27, 2013; to U.S. Prov. App. No. 61/922,068, entitled "SURGICAL VISUALIZATION SYSTEMS", filed Dec. 30, 2013; and to U.S. Prov. App. No. 61/923,188, entitled "SURGICAL VISUALIZATION SYSTEMS", filed Jan. 2, 2014.

BACKGROUND

Field

Embodiments of the present disclosure relate to surgical devices and visualization systems for use during surgery.

Description of Related Art

Some surgical operations involve the use of large incisions. These open surgical procedures provide ready access for surgical instruments and the hand or hands of the surgeon, allowing the user to visually observe and work in the surgical site, either directly or through an operating microscope or with the aide of loupes. Open surgery is associated with significant drawbacks, however, as the relatively large incisions result in pain, scarring, and the risk of infection as well as extended recovery time. To reduce these deleterious effects, techniques have been developed to provide for minimally invasive surgery. Minimally invasive surgical techniques, such as endoscopy, laparoscopy, arthroscopy, pharyngo-laryngoscopy, as well as small incision procedures utilizing an operating microscope for visualization, utilize a significantly smaller incision than typical open surgical procedures. Specialized tools may then be used to access the surgical site through the small incision. However, because of the small access opening, the surgeon's view and workspace of the surgical site is limited. In some cases, visualization devices such as endoscopes, laparoscopes, and the like can be inserted percutaneously through the incision to allow the user to view the surgical site.

The visual information available to a user through laparoscopic of endoscopic contain trade-offs in approach. Accordingly, there is a need for improved visualization systems, for use in minimally invasive surgery.

SUMMARY OF THE INVENTION

The systems, methods and devices of the disclosure each have several innovative aspects, no single one of which is solely responsible for the desirable attributes disclosed herein.

In one aspect, a medical apparatus for use with a surgical tubular retractor configured to hold open an incision and thereby provide a pathway for access of surgical tools to a surgical site, the surgical retractor having a first end, a second end, and a longitudinal axis extending between the first and second ends, wherein the pathway extends along the longitudinal axis into the surgical site and the first end is more proximal than the second end, the apparatus comprising: an imaging insert configured to be received within the tubular retractor, the imaging insert comprising a proximal end and a distal end, wherein the imaging insert is configured to extend along the longitudinal axis of the tubular retractor between the first and second ends of the tubular retractor without substantially obstructing the pathway and maintaining the pathway allowing the surgical tools to gain access to the surgical site through the proximal end of the imaging insert; and wherein the imaging insert comprises: a proximal head of the imaging insert at the proximal end, the proximal head configured to be disposed above the first end of the tubular retractor; and a plurality of cameras inwardly facing toward the pathway; and wherein the plurality of cameras are disposed on an inner surface of the imaging insert. In some embodiments, the medical apparatus wherein the imaging insert further comprises an illumination assembly disposed on an inner surface of the imaging insert. In some embodiments, the medical apparatus wherein the imaging insert is substantially tubular and an outer surface of the imaging insert is configured to contact an inner surface of the tubular retractor. In some embodiments, the medical apparatus wherein the imaging insert comprises one or more pieces configured to be extending from the proximal head, and wherein an outer surface of the one or more a pieces is configured to contact an inner surface of the tubular retractor. In some embodiments, the medical apparatus wherein the imaging insert comprises one or more pieces configured to be disposed adjacent to one another, and wherein an outer surface of the one or more a pieces is configured to contact an inner surface of the tubular retractor. In some embodiments, the medical apparatus wherein the imaging insert comprises one or more annular pieces configured to be disposed adjacent to one another to form a substantially tubular insert, and wherein an outer surface of the one or more annular pieces is configured to contact an inner surface of the tubular retractor. In some embodiments, the medical apparatus wherein the imaging insert comprises a restraint configured to prohibit the imaging insert from passing completely through the pathway of the tubular retractor. In some embodiments, the medical apparatus wherein the proximal head of the imaging insert is wider than a distal portion of the imaging insert to restrain the imaging insert from passing completely through the pathway of the tubular retractor. In some embodiments, the medical apparatus wherein the proximal end of the imaging insert abuts the first end of the tubular retractor and the distal end of the insert is configured to be aligned with the second end of the tubular retractor. In some embodiments, the medical apparatus wherein the imaging insert is configured to slidably engage with the tubular retractor. In some embodiments, the medical apparatus wherein the imaging insert comprises a ridge on an outer surface configured to correspond to a groove on an inner surface of the tubular retractor, wherein the groove is configured to receive the ridge and to allow the insert to be slidably engaged with the retractor. In some embodiments, the medical apparatus wherein the imaging insert comprises a groove on an outer surface configured to correspond to a ridge on an inner surface of the tubular retractor, wherein the groove is configured to receive the ridge and to allow the insert to be slidably engaged with the retractor. In some embodiments, the medical apparatus wherein at least one of the plurality of cameras are on a flexible cable is configured to be moved between the proximal and distal end of the imaging insert. In some embodiments, the medical apparatus wherein the flexible cable is configured to be fed through a slot on the proximal head of the imaging insert, wherein the at least one of the plurality of cameras on the flexible cable is moved closer or further from the distal end as the flexible cable is raised and lowered within the imaging insert. In some embodiments, the medical apparatus further comprising a plurality of connectors on the proximal head of the imaging insert, wherein the plurality of connectors comprise an optical fiber input port, a fluid port, or an air port. In some embodiments, the medical apparatus wherein the illumination assembly comprises at least one illumination source, the at least one illumination source comprising light guides or fibers. In some embodiments, the medical apparatus wherein the illumination assembly comprises at least one illumination source, the at least one illumination source configured to be longitudinally movable along a length of the imaging insert. In some embodiments, the medical apparatus wherein the plurality of cameras are configured to be longitudinally movable along a length of the imaging insert.

In another aspect, a medical apparatus comprising: a camera platform, the camera platform comprising a camera module; a flexible joint; a movement assembly; and a retractor connector surface, the retractor connector surface configured to be mounted to a surface of a retractor; wherein the flexible joint is configured to permit movement of the camera platform relative to the retractor connector surface. In some embodiments, the medical apparatus wherein the movement assembly comprises at least one set of push-pull cables. In some embodiments, the medical apparatus wherein the movement assembly comprises an electromechanical actuator configured to actuate the at least one set of push-pull cables. In some embodiments, the medical apparatus wherein the movement assembly comprises an actuator configured to move the camera platform, wherein the actuator is pneumatically or hydraulically driven.

In certain aspects, a movable mechanical device for positioning a camera on a surgical device is disclosed. The device can include a camera platform configured to attach to the camera, a surgical device connector surface configured to attach to the surgical device, and an electro mechanical actuator configured to control the position of the camera. The electro mechanical actuator can comprise a Micro-Electro-Mechanical System (MEMS) actuator. In some embodiments, the surgical device can include a surgical tool. In other embodiments, the surgical device can include a retractor configured to hold open a surgical incision and to provide access to a surgical site.

In certain aspects, an imaging module for disposing on a surgical device is disclosed. The imaging module can be configured to provide images of a surgical site within a field-of-view of the imaging module. The imaging module can include at least one optical sensor having at least one active detection area on a front face of the at least one optical sensor. The imaging module can also include first and second channels. The first channel can include first imaging optics configured to focus light from the surgical site onto the at least one active detection area to form left-eye view images of the surgical site on the at least one active detection area. The first imaging optics can comprise one or more lenses. The second channel can include second imaging optics configured to focus light from the surgical site onto the at least one active detection area to form right-eye view images of the surgical site on the at least one active detection area. The second imaging optics can include one or more lenses.

The imaging module can also include redirection optics between the first and second imaging optics and the at least one active detection area. The redirection optics can be configured to redirect light from the first and second imaging optics to the at least active detection area such that the at least one optical sensor can be oriented so as to reduce obstruction to the surgical site by the at least one optical sensor. In addition, the imaging module can include a mask associated with the at least one optical sensor. The mask can be configured to partition the at least one active detection area of the at least one optical sensor to define left-eye and right-eye views of the left-eye and right-eye view images.

In various embodiments, the mask can be an electronic mask implemented via software. The mask can be configured to be movable along an axis of the at least one optical sensor. The mask can include two portions. A distance between the two portions can be configured to be adjustable. For example, the distance between the two portions can be configured to be adjustable to control a convergence angle of the imaging module. In some embodiments, the mask can comprise an opening and a size of the opening can be adjustable. The mask can be configured to be controllable via a user interface.

In some embodiments, the at least one optical sensor can comprise a single sensor comprising a single chip. In other embodiments, the at least one optical sensor can comprise first and second sensors. In addition, in some embodiments, the redirection optics can comprise first and second prisms.

The imaging module of certain embodiments can be disposed on a surgical tool. In other embodiments, the imaging module can be disposed on a retractor configured to hold open a surgical incision and to provide access to the surgical site.

In certain aspects, a stereo optical assembly for disposing on a surgical device is disclosed. The assembly can be configured to provide stereo imaging of a surgical site within a field-of-view of the assembly. The stereo optical assembly can include an imaging module. The imaging module can include an optical sensor assembly comprising one or more optical sensors. The imaging module can also include first and second channels. The first channel can comprise first imaging optics configured to focus light from the surgical site onto the optical sensor assembly to form left-eye view images of the surgical site on the optical sensor assembly. The first imaging optics can include one or more lenses. The second channel can comprise second imaging optics configured to focus light from the surgical site onto the optical sensor assembly to form right-eye view images of the surgical site on the optical sensor assembly. The second imaging optics can include one or more lenses.

The imaging module can also include first and second redirection optics. The first redirection optics can be between the first and second imaging optics and the optical sensor assembly. The first redirection optics can be configured to redirect light from the first and second imaging optics to the optical sensor assembly such that the optical sensor assembly can be oriented so as to reduce obstruction to the surgical site by the optical sensor assembly. The second redirection optics can be configured to redirect light from the surgical site to the first and second imaging optics. The second redirection optics can be configured to control a convergence angle of the imaging module. For example, the second redirection optics is configured to increase the convergence angle of the imaging module.

In some embodiments of the stereo optical assembly, the first and second channels can comprise first and second ends respectively. The first and second ends can be configured to receive light from the second redirection optics. The second redirection optics can comprise first and second optical apertures configured to receive light from the surgical site. A center-to-center distance between the first and second optical apertures can be greater than a center-to-center distance between the first and second ends. In some embodiments, the second redirection optics can include first and second prisms.

In various embodiments, the imaging module is a first imaging module, and the stereo optical assembly further comprises a second imaging module. The second imaging module can include a second optical sensor assembly comprising one or more optical sensors. The second imaging module can also include a third channel and a fourth channel. The third channel can comprise third imaging optics configured to focus light from the surgical site onto the second optical sensor assembly to form second left-eye view images of the surgical site on the second optical sensor assembly. The third imaging optics can include one or more lenses. The fourth channel can comprise fourth imaging optics configured to focus light from the surgical site onto the second optical sensor assembly to form second right-eye view images of the surgical site on the second optical sensor assembly. The fourth imaging optics can include one or more lenses.

The second imaging module can also include third redirection optics between the third and fourth imaging optics and the second optical sensor assembly. The second redirection optics can be configured to redirect light from the third and fourth imaging optics to the second optical sensor assembly.

In some such embodiments, the first imaging module has a first convergence angle, the second imaging module has a second convergence angle, and the first convergence angle is substantially equal to the second convergence angle. The first imaging module is located at a proximal location, the second imaging module is located at a distal location, and the distal location is configured to be disposed closer to the surgical site than the proximal location.

The first imaging module can comprise a movable electronic mask associated with the optical sensor assembly or the second imaging module can comprise a movable electronic mask associated with the second optical sensor assembly. In some embodiments, the optical sensor assembly comprises a single sensor comprising a single chip. In other embodiments, the optical sensor assembly comprises first and second sensors. The first redirection optics can include first and second prisms.

The stereo optical assembly of certain embodiments can be disposed on a surgical tool. In other embodiments, the stereo optical assembly can be disposed on a retractor configured to hold open a surgical incision and to provide access to the surgical site.

In certain aspects, a stereo optical assembly for disposing on a surgical device is disclosed. The assembly can be configured to provide stereo imaging of a surgical site within a field-of-view of the assembly. The assembly can include a proximal imaging module at a proximal location. The proximal imaging module can be configured to provide a first left-eye view and a first right-eye view of the surgical site. The assembly can also include a distal imaging module at a distal location. The distal imaging module can be configured to provide a second left-eye view and a second right-eye view of the surgical site. The distal location can be configured to be disposed closer to the surgical site than the proximal location. In addition, an effective separation distance between the first left-eye and right-eye views can be larger than an effective separation distance between the second left-eye and right-eye views.

In various embodiments, the proximal imaging module has a first convergence angle, the distal imaging module has a second convergence angle, and the first convergence angle is substantially equal to the second convergence angle. In some embodiments, at least one of the effective separation distance between the first left-eye and right-eye views and the effective separation distance between the second left-eye and right-eye views can be defined by a plurality of prisms. In some embodiments, the effective separation distance between the first left-eye and right-eye views can be defined by a movable electronic mask associated with an optical sensor of the proximal imaging module or the effective separation distance between the second left-eye and right-eye views can be defined by a movable electronic mask associated with an optical sensor of the distal imaging module.

In certain aspects, an imaging module for disposing on a surgical device is disclosed. The imaging module can be configured to provide images of a surgical site within a field-of-view of the imaging module. The imaging module can include at least one optical sensor having at least one active detection area on a front face of the at least one optical sensor. The imaging module can also include first and second channels. The first channel can include first imaging optics configured to focus light from the surgical site onto the at least one active detection area to form left-eye view images of the surgical site on the at least one active detection area. The first imaging optics can comprise one or more lenses. The second channel can include second imaging optics configured to focus light from the surgical site onto the at least one active detection area to form right-eye view images of the surgical site on the at least one active detection area. The second imaging optics can include one or more lenses.

The imaging module can also include redirection optics between the first and second imaging optics and the at least one active detection area. The redirection optics can be configured to redirect light from the first and second imaging optics to the at least active detection area such that the at least one optical sensor can be oriented so as to reduce obstruction to the surgical site by the at least one optical sensor.

In some embodiments, the at least one optical sensor can comprise a single sensor comprising a single chip. In other embodiments, the at least one optical sensor can comprise first and second sensors. In addition, in some embodiments, the redirection optics can comprise first and second prisms.

The imaging module of certain embodiments can be disposed on a surgical tool. In other embodiments, the imaging module can be disposed on a retractor configured to hold open a surgical incision and to provide access to the surgical site.

In various aspects, a stereo camera system is provided. The stereo camera system can include a pair of image sensors comprising a left image sensor and a right image sensor. Each of the pair of image sensors can have an active detection area on a front face of the image sensor. The left image sensor can be offset along a first direction from the right image sensor. In addition, the front face of the left image sensor can be oriented such that a plane of the front face of the left image sensor is parallel to a plane of the front face of the right image sensor. The front face of the left image sensor can face the front face of the right image sensor. Each of the planes of the front faces can be oriented perpendicular to the first direction.

In various embodiments, the stereo camera system can include a pair of lens trains comprising a left lens train having a plurality of lens elements along a left optical path and a right lens train having a plurality of lens elements along a right optical path. The left optical path can be offset along the first direction from the right optical path. The stereo camera system can also include a pair of optical redirection elements comprising a left optical redirection element positioned along the left optical path and configured to redirect the left optical path to the front face of the left image sensor and a right optical redirection element positioned along the right optical path and configured to redirect the right optical path to the front face of the right image sensor.

In some embodiments of the stereo camera system, the left optical redirection element comprises a left prism and the right redirection element comprises a right prism. In some such embodiments, the left prism can be offset from the right prism along the first direction. The left prism can comprise a primary reflective face that is orthogonal to a primary reflective face of the right prism. In some embodiments, the left optical redirection element comprises a left mirror and the right redirection element comprises a right mirror.

In some embodiments, the left optical redirection element can be configured to redirect the left optical path 90 degrees and the right optical redirection element can be configured to redirect the right optical path 90 degrees. The redirected left optical path and the redirected right optical path can be anti-parallel to one another. In some embodiments, the left optical path and the right optical path can be parallel.

In various embodiments, the left image sensor can be a two-dimensional detector array and the right image sensor can also be a two-dimensional detector array. For example, the left image sensor can be a CCD detector array and the right image sensor can also be a CCD detector array.

In various aspects, a stereo camera system is provided. The stereo camera system can comprise a pair of image sensors comprising a left image sensor and a right image sensor. The stereo camera system can also comprise a pair of lens trains comprising a left lens train having a plurality of lens elements along a left optical path and a right lens train having a plurality of lens elements along a right optical path. The left optical path can be offset laterally from the right optical path. The stereo camera system can also comprise a pair of optical redirection elements comprising a left optical redirection element positioned along the left optical path and configured to redirect the left optical path to the front face of the left image sensor and a right optical redirection element positioned along the right optical path and configured to redirect the right optical path to the front face of the right image sensor.

Furthermore, certain embodiments also include a surgical visualization system comprising a plurality of camera systems. At least one of the plurality of camera systems can include a stereo camera system in accordance with certain embodiments as described herein. Various embodiments also include a retractor including a stereo camera system as described herein disposed thereon. In addition, some embodiments include a surgical tool including a stereo camera system as described herein disposed thereon.

In various aspects, a surgical visualization system display is disclosed. The surgical visualization system display can include at least one camera configured to acquire video images of a surgical tool. The at least one camera can be configured to be disposed on a surgical device. The surgical visualization system can also include an image processing system in communication with the at least one camera. The image processing system can comprise at least one physical processor. In certain embodiments, the image processing system can be configured to receive tracking information associated with the location of the surgical tool, and to adjust a focal length and/or orientation of the at least one of camera, based at least in part on the received tracking information.

In various embodiments, the image processing system can be configured to adjust a focal length and/or orientation of the at least one camera so as to maintain focus of the surgical tool with movement of the surgical tool. The at least one camera can comprise a plurality of cameras. The surgical device can comprise a retractor.

In some embodiments, the image processing system can be configured to adjust the focal length of the at least one camera, based at least in part on the received tracking information. In some embodiments, the image processing system can be configured to adjust the orientation of the at least one camera, based at least in part on the received tracking information.

The surgical visualization system display can further include a foot pedal, where actuation of the foot pedal can be configured to send a signal causing the image processing system to receive tracking information associated with the location of the surgical tool, and to adjust a focal length and/or orientation of the at least one camera, based at least in part on the received tracking information.

In certain aspects, a surgical visualization system display is disclosed. The surgical visualization system display can include at least one camera disposed on a surgical tool and configured to acquire video images of a surgical site. The surgical visualization system display can also include an image processing system in communication with the at least one camera. The image processing system can comprise at least one physical processor. The image processing system can be configured to receive tracking information associated with the location of the surgical tool, and to adjust a focal length and/or orientation of the at least one camera, based at least in part on the received tracking information.

In some embodiments, the image processing system can be configured to adjust the focal length of the at least one camera, based at least in part on the received tracking information. In some embodiments, the image processing system can be configured to adjust the orientation of the at least one camera, based at least in part on the received tracking information.

In another aspect, a medical apparatus comprising a surgical visualization system console; and a drive system disposed within the console and in communication with at least one surgical tool, wherein the drive system comprises at least one drive board configured to drive the at least one surgical tool. In some embodiments, the medical apparatus wherein the drive system comprises an ultrasonic driver board. In some embodiments, the medical apparatus wherein the drive system comprises a radiofrequency (RF) driver board. In some embodiments, the medical apparatus wherein the RF driver board is configured to support at least two modulation formats associated with at least two surgical tools, respectively. In some embodiments, the medical apparatus wherein the at least one surgical tool comprises an ultrasonic tissue aspirator, bipolar coagulation and cutting tool, bipolar forceps, or a combination thereof. In some embodiments, the medical apparatus comprising a foot pedal in communication with the drive system. In some embodiments, the medical apparatus wherein the foot pedal is configured to send a signal to the drive system indicative of a power level associated with the one or more surgical tools. In some embodiments, the medical apparatus wherein the power level is proportional to a degree to which the foot pedal is configured to be depressed.

In another aspect, a method of driving surgical tools, the method comprising receiving a signal from a foot pedal to drive a first surgical tool, wherein the signal includes information as to a degree to which the foot pedal is depressed; and driving power to the first surgical tool in proportion to the degree to which the foot pedal is depressed. In some embodiments, the method further comprising, driving power to a second surgical tool, wherein the second surgical tool has a modulation format different than that of the first surgical tool.

In certain aspects, a surgical visualization system display is disclosed. The surgical visualization system display can include a plurality of cameras, at least one disposed on a retractor. A first camera of the plurality can be configured to image fluorescence in a surgical site. A second camera of the plurality can be configured to produce a non-fluorescence image of said surgical site. The first and second cameras can have different spectral responses. For example, in some embodiments, one of the first and second cameras is sensitive to infrared and the other is not.

In another aspect, a surgical visualization system configured to receive images from one or more cameras, the surgical visualization system comprising a display, electronics configured to receive and process image signals from the one or more cameras, an input connector configured to fluidly connect with a source of pneumatic pressure, and one or more pneumatic outputs configured to fluidly connect to the input connector. In some embodiments, surgical visualization system further comprising a hydraulic pressure circuit having one or more valves, wherein at least one of the one or more pneumatic outputs is configured to operate one or more of the valves of the hydraulic pressure circuit. In some embodiments, surgical visualization system wherein the hydraulic pressure circuit is fluidly connected to one or more surgical tools and is configured to operate the one or more surgical tools using hydraulic pressure. In some embodiments, surgical visualization system wherein at least one of the one or more valves is an elastomeric proportional valve. In some embodiments, surgical visualization system wherein at least one of the one or more pneumatic outputs is a solenoid. In some embodiments, surgical visualization system wherein at least one of the one or more pneumatic outputs is a piston. In some embodiments, surgical visualization system wherein at least one of the pneumatic outputs is a pneumatic actuator. In some embodiments, surgical visualization system further comprising one or more valves positioned on fluid lines between the source of pneumatic pressure and the one or more pneumatic outputs. In some embodiments, surgical visualization system further comprising a hydraulic cassette assembly. In some embodiments, surgical visualization system wherein at least one of the one or more pneumatic outputs is configured to operate a cassette lifter configured to raise and/or lower the hydraulic cassette assembly. In some embodiments, surgical visualization system wherein one or more of the pneumatic outputs are configured to operate as a tube ejector for a peristaltic pump.

In another aspect, a surgical tool comprising a proximal handle portion, a distal handle portion connected to the proximal handle portion and rotatable with respect to the proximal handle portion about an axis of rotation, a base portion connected to the distal handle portion and fixed thereto in a direction parallel to the axis of rotation, a top portion connected to the distal handle portion and movable with respect to the distal handle portion in the direction parallel to the axis of rotation, the top portion having a cutting edge on a distal end of the top portion configured to operate with a cutting portion on the base portion to cut bone or tissue, a proximal actuation chamber within the proximal handle portion, a piston connected to the top portion and fixed thereto in the direction parallel to the axis of rotation; and an actuation element positioned at least partially within the proximal actuations chamber and configured to exert an axial force on the piston in the direction parallel to the axis of rotation. In some embodiments, the surgical tool further comprising a distal actuation chamber within the distal handle portion. In some embodiments, the surgical tool further comprising a biasing element positioned within one or more of the proximal handle portion and the distal handle portion and configured to bias the piston in a direction parallel to the axis of rotation and away from a distal end of the base portion. In some embodiments, the surgical tool wherein the actuation element is a bag or balloon configured to be inflated by a source of physiological saline. In some embodiments, the surgical tool further comprising a return valve configured to introduce physiological saline to the tool to compress the actuation element.

In another aspect, a surgical tool comprising; a hydraulic impeller assembly comprising a turbine housing defining a blade cavity, a flow director positioned at least partially within the turbine housing, an impeller having a plurality of impeller blades, the impeller positioned at least partially within the blade cavity, an output shaft rotatably connected to the impeller and configured to transfer a torque from the impeller to a drill, and one or more ports in a wall of the blade cavity providing fluid communication between an interior of the blade cavity and an exterior of the blade cavity; a hydraulic fluid input port; a pneumatic fluid input port; and a controller configured to control a proportion of pneumatic and hydraulic fluids input into the blade cavity. In some embodiments, the surgical tool further comprising a fluid output port line configured to facilitate fluid communication between at least one of the one or more ports and a hydraulic pressure source. In some embodiments, the surgical tool further comprising a vacuum source configured to extract fluid from the blade cavity through the one or more ports in the wall of the blade cavity. In some embodiments, the surgical tool wherein the vacuum source is an external pump. In some embodiments, the surgical tool wherein the vacuum source is a bypass channel in the turbine housing in fluid communication with the blade cavity via the one or more ports, wherein a low pressure fluid is passed through the bypass channel to draw fluid out from the blade cavity via the Venturi effect. In some embodiments, the surgical tool wherein the low pressure fluid is a gas. In some embodiments, the surgical tool wherein at least a portion of the fluid extracted from the blade cavity is physiological saline. In some embodiments, the surgical tool wherein the hydraulic impeller assembly is configured to receive both pressurized hydraulic fluid and pressurized pneumatic fluid to rotate the impeller. In some embodiments, the surgical tool wherein the controller is configured to increase the proportion of hydraulic fluid input to the blade cavity when higher torque is desired and to increase the proportion of pneumatic fluid input to the blade cavity when a higher rotational speed is desired.

In another aspect, a medical apparatus comprising a surgical device, at least one camera disposed on the surgical device, and a hydraulic system configured to deliver fluid to the at least one camera to remove obstructions therefrom, wherein said hydraulic system comprises a pulsing valve connected to a high pressure source of said fluid configured to provide pulses of fluid. In some embodiments, the medical apparatus wherein said pulsing valve comprises a pop off valve configured to open when a pressure threshold is reached to provide increased pressure beyond the threshold value resulting in a pulse of liquid from the pulsing valve. In some embodiments, the medical apparatus wherein said at least one camera comprises a plurality of cameras and said pulsing valve is disposed in said hydraulic system such that the fluid is delivered to each of the plurality of cameras at the same time. In some embodiments, the medical apparatus wherein said pulsing valve is disposed in a line that splits into different fluid outlets to clean different cameras, said pulsing valve disposed upstream of said split. In some embodiments, the medical apparatus wherein said hydraulic system is further configured to deliver pressurized air to the at least one camera after said fluid is delivered. In some embodiments, the medical apparatus wherein said surgical device comprises a retractor.

In another aspect, a medical apparatus comprising a surgical device, at least one camera disposed on the surgical device, and a hydraulic system configured to deliver air to the at least one camera, wherein said hydraulic system comprises a pulsing valve connected to a high pressure source of air to provide pulses of air. In some embodiments, the medical apparatus wherein said pulsing valve comprises a pop off valve configured to open when a pressure threshold is reached to provide increased pressure beyond the threshold value resulting in a pulse of air from the pulsing valve.

In another aspect, a medical apparatus comprising a surgical device, at least one camera disposed on the surgical device, said at least one camera having camera optics, and a hydraulic system configured to deliver fluid and air to the camera optics of said at least one camera to remove obstructions therefrom, wherein said hydraulic system comprises a three way valve connected to a supply of said fluid and a supply of high pressure air, said three way valve configured to selectively shut off said supply of fluid and to provide instead pressurized air thereby reducing inadvertent leakage of fluid onto the camera optics. In some embodiments, the medical apparatus wherein said hydraulic system is configured to deliver fluid pulses and air pulses to said at least one camera. In some embodiments, the medical apparatus further comprising a pop off valve, wherein said three way valve is disposed downstream of said pop off valve. In some embodiments, the medical apparatus wherein said surgical device comprises a retractor.

In another aspect, a medical apparatus comprising a surgical device, at least one camera disposed on the surgical device, said at least one camera having camera optics, and a hydraulic system comprising a valve connected to a high pressure source of fluid and configured to deliver fluid to the camera optics of said at least one camera to remove obstructions therefrom, wherein said hydraulic system is configured to open said valve periodically based on a pre-programmed schedule or a schedule selected by a user.

In another aspect, a medical apparatus comprising a surgical device, at least one camera disposed on the surgical device, said at least one camera having camera optics, and a hydraulic system comprising a valve connected to a high pressure source of fluid and configured to deliver fluid to the camera optics of said at least one camera to remove obstructions therefrom, wherein said hydraulic system is configured to deliver fluid when an obstruction reducing the amount of light entering the camera is detected. In some embodiments, the medical apparatus wherein said at least one camera produces an image signal and said apparatus is configured to monitor said image signal to determine when visibility is compromised and thereby trigger delivery of said fluid to clean the camera optics. In some embodiments, the medical apparatus wherein camera intensity is monitored. In some embodiments, the medical apparatus wherein attenuation of red wavelength compared to green wavelength is monitored to determine whether blood is on the camera reducing the amount of light entering the camera.

In another aspect, a suction system for a surgical system, the suction system comprising: a suction cassette including: a cassette housing; and a plurality of ports facilitating fluid communication between an interior and an exterior of the cassette housing; a first suction line in fluid communication with the suction cassette and configured to be positioned in fluid communication with a surgical site; a second suction line in fluid communication with the suction cassette and configured to be positioned in fluid communication with the surgical site; and a storage tank in fluid communication with the suction cassette. In some embodiments, the suction system further comprising a connector in fluid communication with the suction cassette and with a vacuum source. In some embodiments, the suction system wherein the vacuum source maintains a pressure below ambient pressure within the storage tank. In some embodiments, the suction system wherein the first suction line is configured to operate as a high flow suction line to suction heavy bleeding. In some embodiments, the suction system wherein the second suction line is configured to operate as a low flow suction line to identify and coagulate low flow bleeding. In some embodiments, the suction system further comprising an intermediate storage tank positioned at least partially within the cassette housing and in fluid communication with one or more of the first suction line and the second suction line. In some embodiments, the suction system further comprising a pump positioned on a fluid line between the intermediate storage tank and the storage tank to pull material from the intermediate storage tank to the storage tank. In some embodiments, the suction system wherein the pump is a peristaltic pump.

A separate apparatus can include a translation system having an upper connecting member and a lower connecting member, the translation system designed to have a component attached to the translation system, wherein the component is configured to translate relative to the upper connecting member along at least a first axis and a second axis, a pitch-yaw adjustment system designed to attach to the component, the pitch-yaw adjustment system designed to rotate the component about a joint around an axis parallel to the first axis and rotate the component about the joint around an axis parallel to the second axis, a first control member designed to attach to the translation system via one or more control member joints, wherein the first control member is physically coupled to both the translation system and the pitch-yaw adjustment system so as to provide control thereto.

In some embodiments, the component can be attached to the lower connecting member via an arm. In some embodiments, the first control member can be physically coupled to the translation system such that the component can be translated along the first axis or second axis by translating the first control member in the direction parallel to the first axis or second axis respectively. In some embodiments, the first control member can be designed to connect to a component of the apparatus via a joint having three rotational degrees of freedom. In some embodiments, the first control member can be designed to connect to the translation system via the lower connecting member. In some embodiments, the translation system can also include a guide assembly designed to attach the upper connecting member to the lower connecting member, wherein the guide assembly can be positioned between the upper connecting member and the lower connecting member. In some embodiments, the first control member can be physically coupled to the pitch-yaw adjustment system such that the component can be rotated about the joint around the first axis or second axis by rotating the first control member about the control member joint around an axis parallel to the first axis or second axis respectively. In some embodiments, the pitch-yaw adjustment system can be designed such that rotation of the first control member about the control member joint can result in about a one-to-one rotation of the component about the joint. In some embodiments, the pitch-yaw adjustment system can be designed such that rotation of the first control member about the control member joint can result in greater than a one-to-one rotation of the component about the joint. In some embodiments, the pitch-yaw adjustment system can be designed such that rotation of the first control member about the control member joint can result in less than a one-to-one rotation of the component about the joint.

BRIEF DESCRIPTION OF THE DRAWINGS

FIG. 4B-4E shows tubular inserts partitioned into separate segments as seen in the cross-section orthogonal to the length of the insert.

FIG. 8A shows a schematic illustration of a surgical visualization system including a foot pedal.

FIG. 8B illustrates an embodiment of multiple foot pedals 10801 within a frame.

DETAILED DESCRIPTION OF THE PREFERRED EMBODIMENT

The following description is directed to certain embodiments for the purposes of describing the innovative aspects of this disclosure. However, a person having ordinary skill in the art will readily recognize that the teachings herein can be applied in a multitude of different ways. Thus, the teachings are not intended to be limited to the embodiments depicted solely in the figures. and described herein, but instead have wide applicability as will be readily apparent to one having ordinary skill in the art.

Cameras on Retractors

Figure 1A:
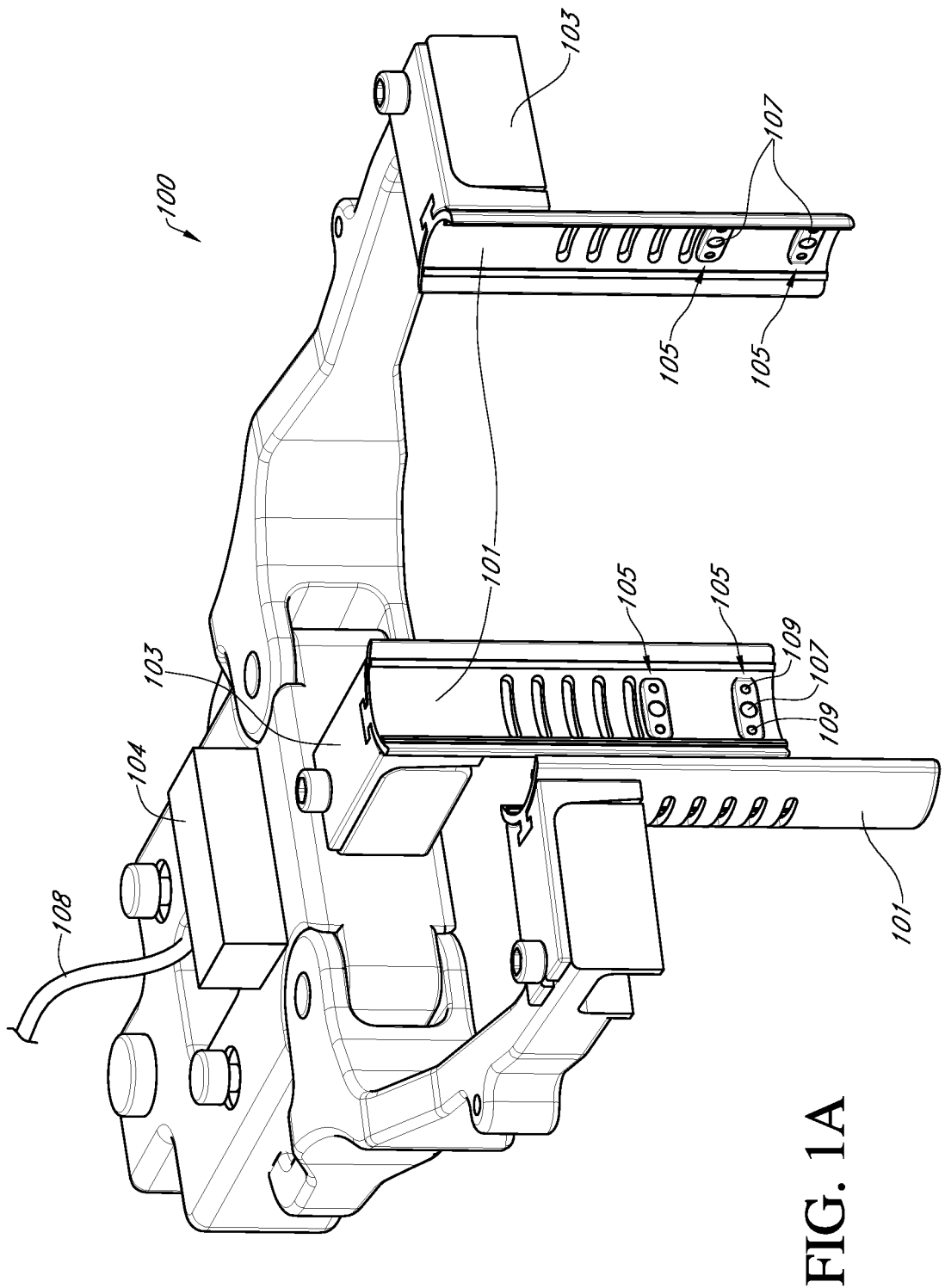
FIGS. 1A-C show an embodiment of a surgical retractor device having an integrated imaging assembly.
Figure 1B:
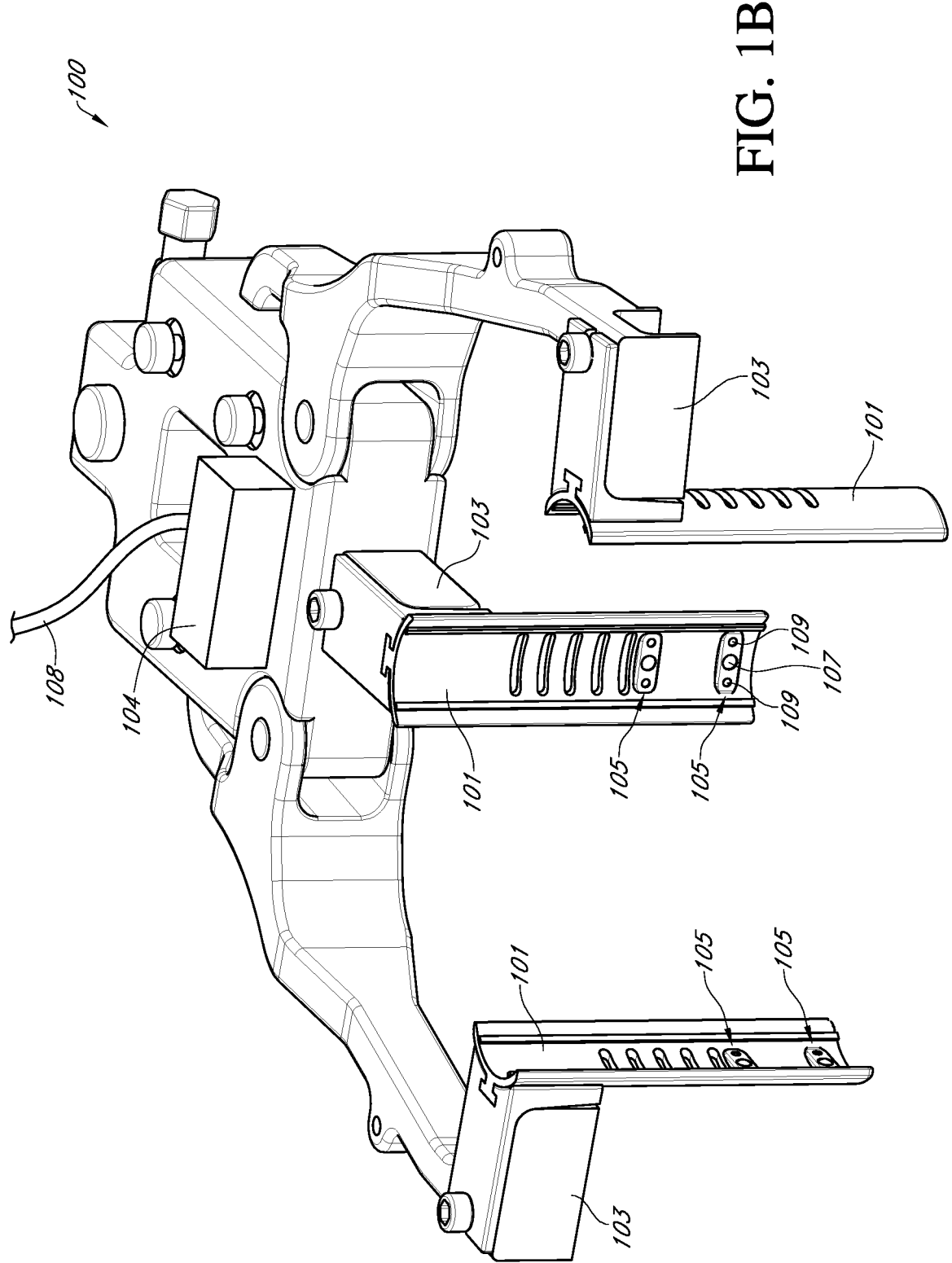
Figure 1C:
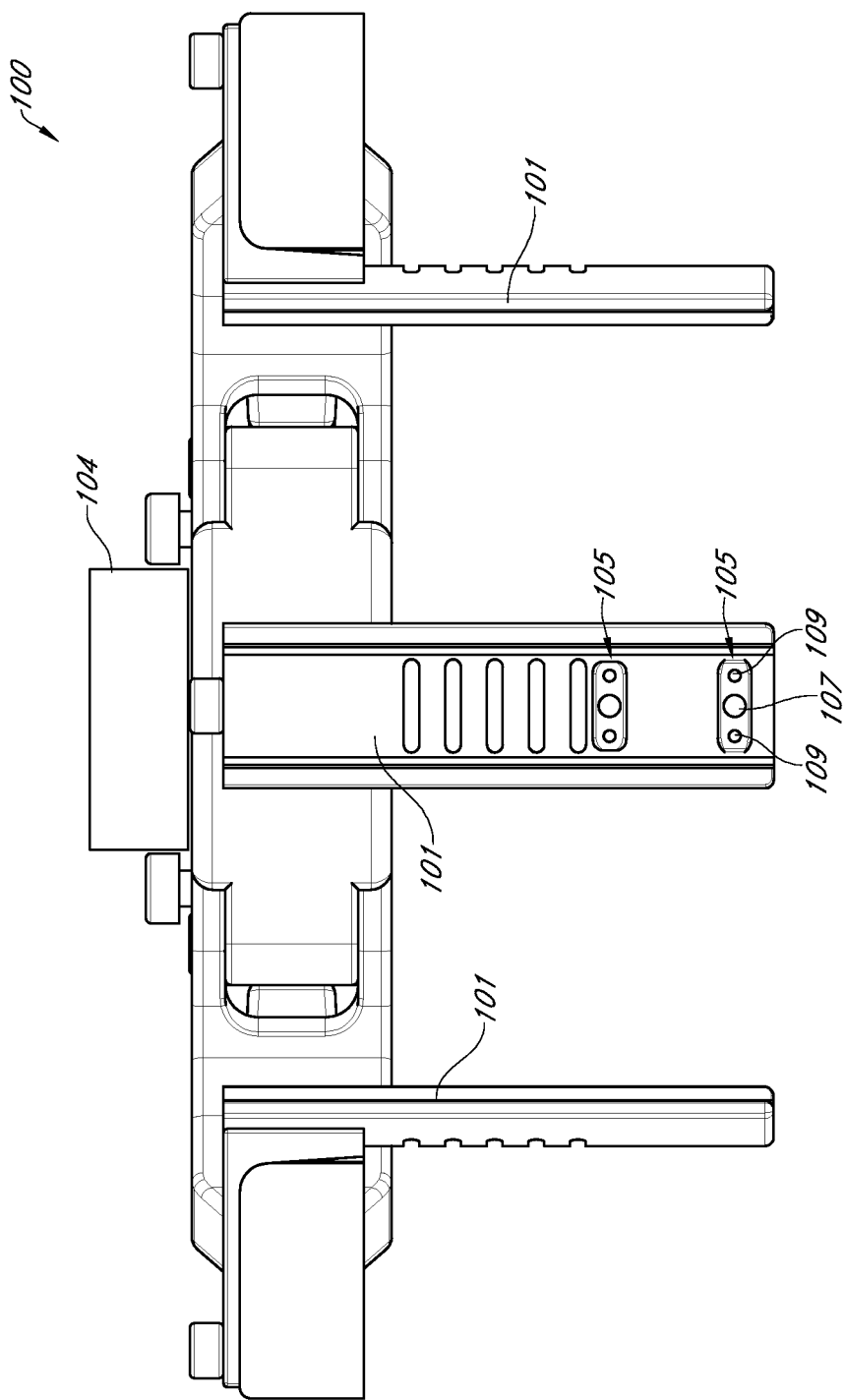

FIGS. 1A-C show one embodiment a surgical retractor device that includes an integrated imaging assembly. In some embodiments, the imaging assembly includes a plurality of integrated cameras. The retractor 100 includes three blades 101, however, more or less may be included depending on the design. Each of the blades may be attached to an articulable arm 103 that allows for the position of the blades to be adjusted during the operation. For example, following a small incision, the three blades 101 can be arranged in a closed position where each are positioned close to one another. In this closed configuration, the three blades can be introduced through the incision, and then expanded to provide for an operating pathway or working space. In other embodiments 4, 5, 6, 7, 8 or more blades, fingers, retractor members, or other barriers may be employed (or fewer members such as two blades, etc., or even a single member such as a single lumen of a tubular retractor may be used). In various embodiments, the surgical area may be at least 400 mm$^2$, for example, have an opening with an areas between 400 and 2100 mm$^2$. The working space may be an area centrally located between retractor blades (or within the lumen of a tubular retractor) that allows for surgical tools or other instruments to pass through. As shown, the retractor does not obstruct the center of the retractor (e.g., array of retractor blades, finger, members, etc., or lumen of a tubular retractor) and the open region formed by the retractor and permits unobstructed access to the center of the surgical site for ready access by the surgeon. Each of the blades 101 includes one or more integrated cameras, or cameras with combined stereo paths to one sensor or camera module 105. In various embodiments the number of camera modules and configurations can vary. In the illustrated embodiment, each camera module 105 includes a camera 107 and one or more, or two illumination sources 109 disposed on opposite sides of the camera 107. In various embodiments, the number of illumination sources per camera module may vary. In some embodiments, the illumination sources may not be disposed directly adjacent any particular camera. In some embodiments, the illumination sources can be omitted, and the camera module can rely on ambient supplementary or overhead light or light directed from a light source located elsewhere. In some embodiments, the orientation of an integrated camera 107 may be substantially fixed with respect to the retractor blade 101 or other surgical tool. In some embodiments, the camera 107 and/or the camera module 105 may be adjustable with respect to the retractor blade 101.

In the illustrated embodiment, the retractor blades 101 are substantially rigid. In various embodiments, the retractor blades may be malleable, and may have a wide range of different structural features such as width, tension, etc. For example, stronger, larger retractor blades may be desired for spinal and trans-oral surgery, while weaker, smaller retractor blades may be desired for neurosurgery. In some embodiments, the retractor can be configured such that different blades can be arranged as desired.

Each of the camera modules 105 are in electrical communication with an aggregator 104. The aggregator 104 is configured to receive input from each of the camera modules 105, and to connect to external components via electrical cable 108. For example, the hub or aggregator 104 may receive image data from each of the camera modules 105 and may transmit the image data to an image processing module (not shown). In the illustrated embodiment, the wiring connecting the camera modules 105 with the aggregator 104 is imbedded within the retractor blades 101 and articulating arms 103 and is not visible. In some embodiments, as described in more detail below, cables connecting the camera modules 105 with the aggregator 104 may be adhered (either permanently or non-permanently, e.g., releasably) to the exterior surface of the retractor 100. In the illustrated embodiment, the hub or aggregator 104 is affixed to an upper surface of the retractor 100. The aggregator may be positioned at any locations relative to the retractor 100, or may be disconnected from the retractor 100 altogether. The aggregator may contain camera interface electronics, tracker interface electronics and SERDES to produce a high speed serial cable supporting all cameras in use. In various embodiments, the retractor camera output is coupled to a console which causes video from the retractor camera to be presented on display.

Although the illustrated embodiment shows integrated camera modules 105, in various embodiments the camera modules 105 may be removably attached to the retractor blades 101. In some embodiments, the camera modules 105 can be disposed within pre-positioned receptacles on the retractor blades 101 or other surgical device. In some embodiments, the camera modules 105 can be disposed at a plurality or range of locations desired by the user on the retractor blades 101. In various embodiments, the orientation and position of the sensors can be adjusted by the user, e.g., physician, nurse, technician, or other clinician. In some embodiments, for example, the camera may be disposed on a track such that the camera can slide up and down the retractor, e.g., retractor blade. The height of the camera or camera within or above the surgical site may thereby be adjusted as desired. Other arrangements for laterally adjusting the position of the camera may be used. Additionally, in various embodiments, the cameras may be configured to have tip and/or tilt adjustment such that the attitude or orientation of the camera may be adjusted. The line of sight or optical axis of the cameras can thereby be adjusted to, for example, be directed more downward into the surgical site or be directed less into the surgical sight and more level or angled in different lateral directions. The camera modules 105 can include sensors or markers for, e.g., electromagnetic or optical tracking or use encoders, accelerometers, gyroscopes, or inertial measurement units (IMUS) or combinations thereof or any other orientation and/or position sensors, as described in more detail below. Tracking can provide location and/or orientation of the cameras. The images obtained by the cameras may be stitched together or tiled using image processing techniques. Tracking or otherwise knowing the relative locations of the sensor can assist in image processing and display formatting.

In various embodiments, pairs of cameras together provide information for creating a stereo effect or 3-dimensional (3D) image. Pairs of cameras, for example, may be included on each of the blades 101 of the retractor 100.

As illustrated, the retractor is configured to hold open tissue so as to produce an open region or cavity centrally located between the blades. Notably, in various embodiments, this open central region is unobstructed by the retractor. In particular, the central portions of the open region would be unobstructed by features of the retractor such that the surgeon would have clear access to the surgical site. The surgeon could thus more freely introduce and utilize his or her tools on locations within the surgical site. Additionally, this may enable the surgeon to use tools with both hands without the need to hold an endoscope.

Also as illustrated, the cameras are disposed on the blades of the retractor such that the cameras face inward toward the surgical site that would be held open by the retractor blades. The cameras in this example would be disposed about the central open region held open by the retractor blades so as to provide views from locations surrounding the surgical site. The camera thus would face objects within the surgical site such as structures on which tools would be used by the surgeon to operate.

In this particular example, the cameras on two of the blades face each other such that the leftmost blade and the cameras thereon would be in the field-of-view of the cameras on the rightmost blade and vice versa. The cameras on the leftmost blade may be anti-parallel to the cameras on the rightmost blade and have optical axes oriented at an angle, θ, of 180° with respect to each other. The cameras on the remaining blade may be directed orthogonally to the other two blades and thus have optical axes directed at an angle, θ, of 90° with respect to each other. Retractors with cameras can be reaffixed to a frame or mounting structure during a procedure and the cameras can reorient themselves with respect to relative position within an array of the cameras through their communication protocol with the aggregator and video switching unit.

In some embodiments, the field-of-views of the different cameras, and hence the images produced by the different cameras, may overlap. Image processing may be employed to yield increased resolution at the regions of overlap. Likewise, the number of sensors used may be increased to provide increased field-of-view and/or resolution. Likewise, cameras with overlapping images can be electronically magnified thereby making their images adjacent rather than overlapping.

A minimally invasive spine surgery can use a tubular retractor having a circular working space with a diameter of approximately 25 mm. The retractor contains blades, fingers, or at least one barrier such as e.g., a tube that holds tissue back to maintain open the surgical site. Multiple cameras located on the retractor at locations within the surgical field or in very close proximity thereto, e.g., within 75 mm of the surgical opening, can provide a useful viewpoint for the surgeon. The cameras may for example be located on the blades, fingers, tubular barrier, or other portion of the retractor close to the surgical field or within the patient and the surgical field. The cameras may include pairs of cameras arranged and/or oriented to provide stereo and thus 3D imaging or single CMOS camera chips with dual optics to provide stereo. The cameras may be located at various locations in relation to surgical devices, for example, the cameras can be located proximally and distally along or near a retractor, wherein the location of the cameras can be configured to facilitate both the progression of surgery and an enhanced view or view selection of an area of interest.

Tubular Retractor

Figure 2A:
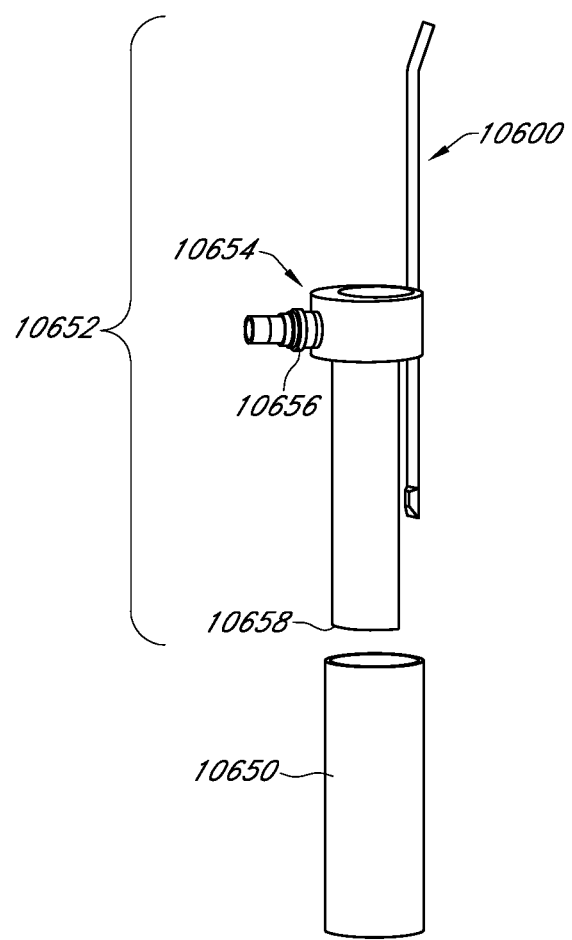
FIG. 2A is a schematic illustration of a tubular retractor and an imaging insert including an illumination assembly and a camera module.

FIG. 2A is a schematic illustration of a tubular retractor and an imaging insert including an illumination assembly and a camera module. A tubular retractor 10650 is sized and configured to receive an insert 10652 therein, which includes an illumination assembly 10654 and a camera module 10600. In the illustrated embodiment, the camera module 10600 is slidably received within the insert 10652, allowing for the camera module 10600 to be raised and lowered (i.e. advanced distally or retracted proximally) with respect to the insert 10652. The illumination assembly 10654 in the illustrated embodiment takes a curvilinear shape, forming a C-shape as seen in plan view (for example, from the top in FIG. 2A). An optical fiber input port 10656 is configured to receive an optical fiber line such as an optical fiber bundle which delivers light to the illumination assembly. Interior light guides or fibers carry received light from the input port 10656 to output ends disposed at the distal end 10658 of the illumination assembly 10654. In use, light output from the distal end of the illumination assembly 10658 can illuminate the field of view to be imaged by the camera module 10600.

Figure 2B:
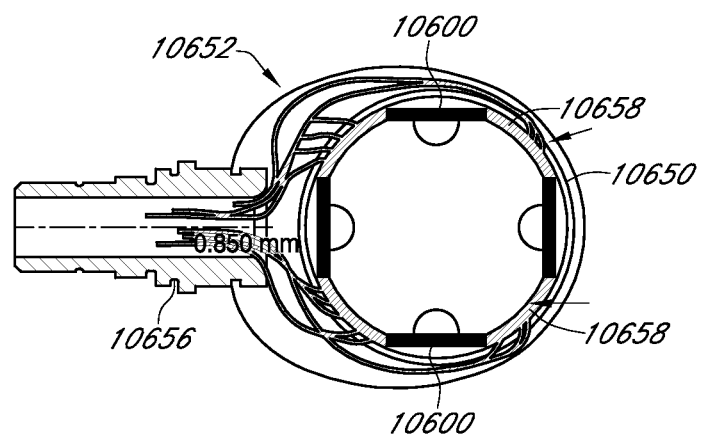
FIG. 2B is a schematic cross-section of a retractor having an imaging insert received therein.

In the embodiment of FIG. 2A, a single camera module 10600 is disposed within the insert 10652. However, in other embodiments, more camera modules 10600 can be coupled with the insert 10652. For example, as illustrated in FIG. 2B, a retractor 10650 has received therein an insert 10652 which includes an illumination assembly 10654 and four camera modules 10600. As seen in cross-section, four outputs 10658 of the illumination assembly are interspersed between adjacent camera modules 10600.

Figure 3A:
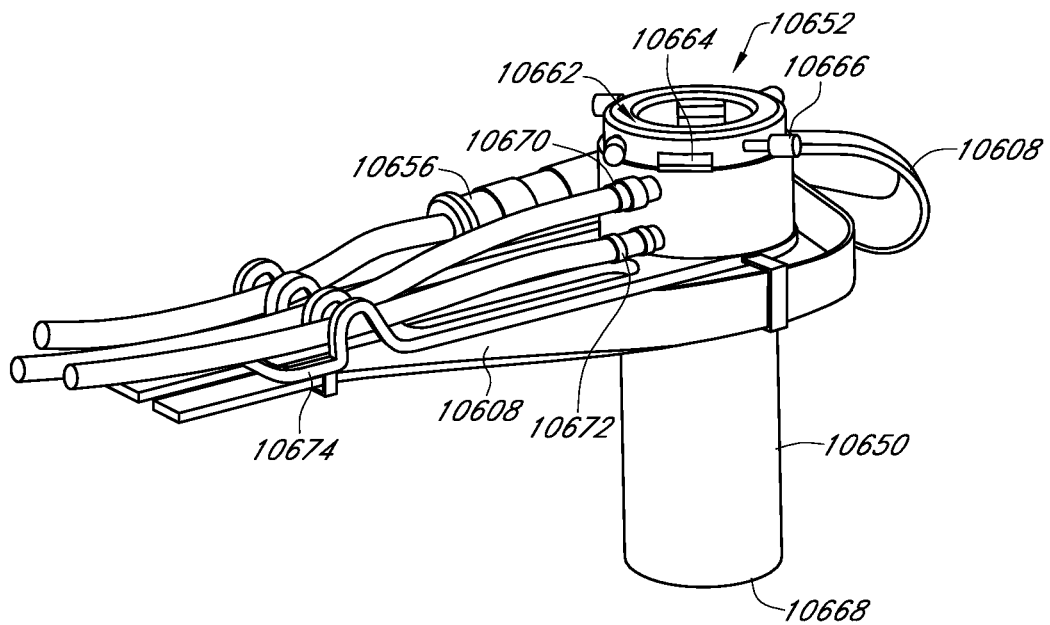
FIGS. 3A-E are schematic illustrations of a tubular retractor assembly with imaging insert received therein.
Figure 3B:
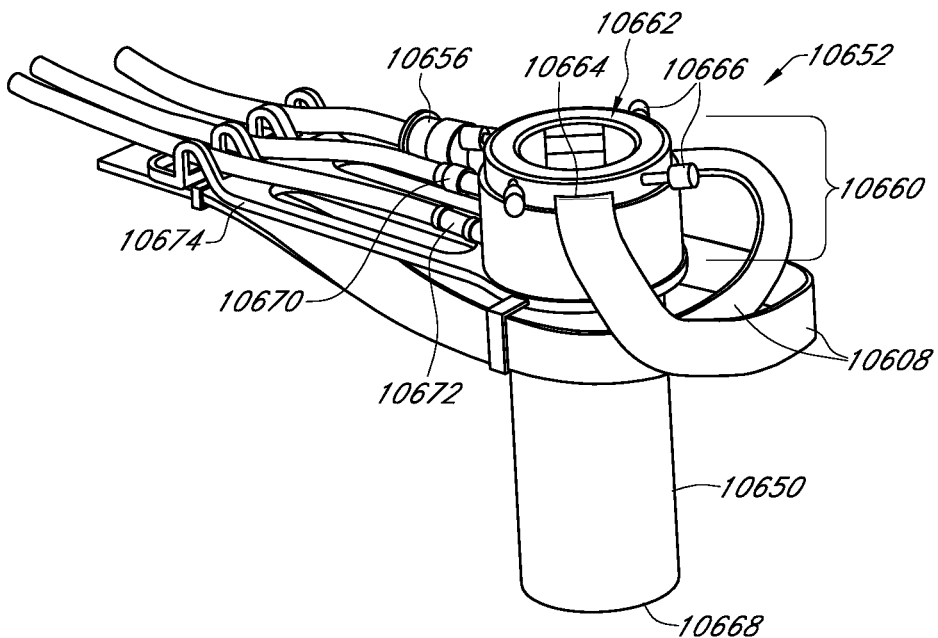
Figure 3C:
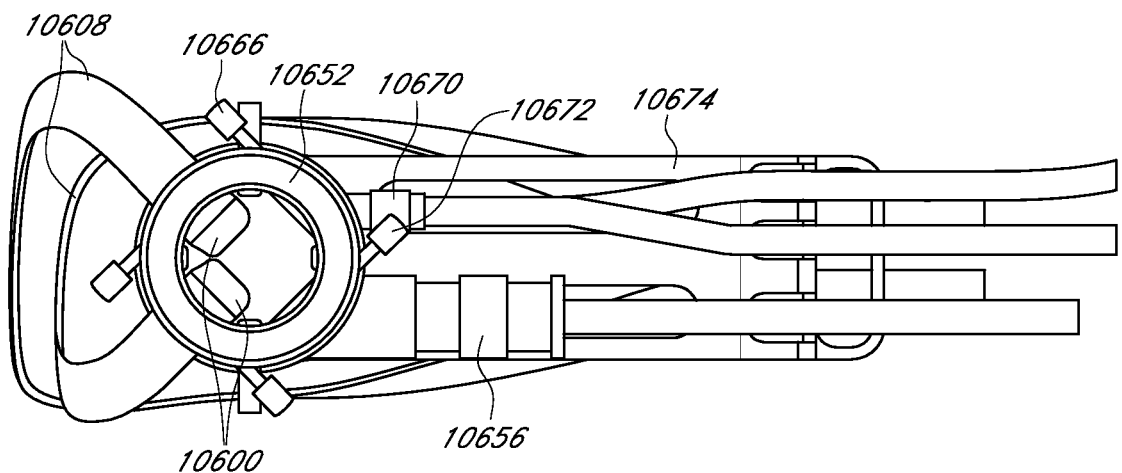
Figure 3D:
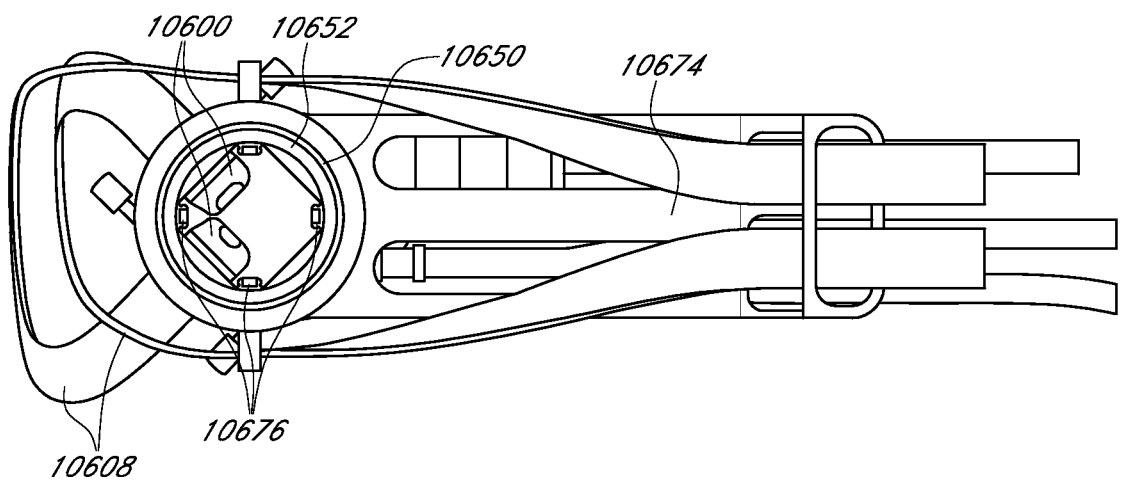
Figure 3E:
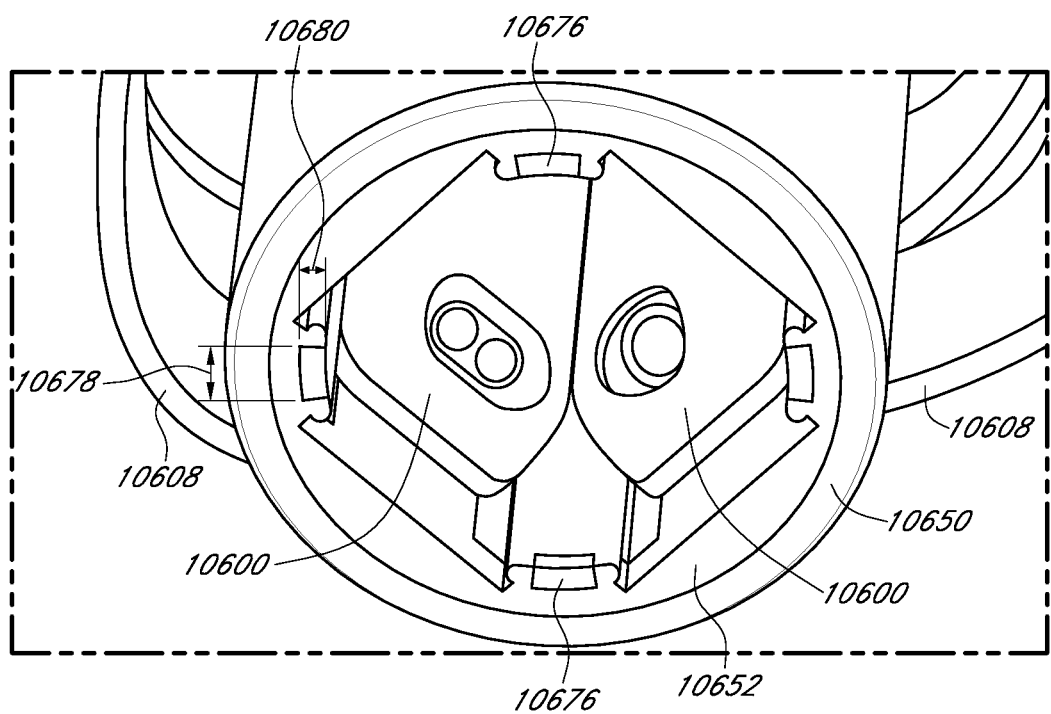

FIGS. 3A-D are schematic illustrations of a tubular retractor assembly with an imaging insert received therein. FIGS. 3A-B show side perspective views with FIGS. 3C-D showing top and bottom views, respectively. FIG. 3E shows an enlarged detail view of the distal end of the tubular retractor assembly with imaging insert received therein. The insert 10652 is received within tubular retractor 10650, with a proximal head 10660 of the insert 10652 resting above the tubular retractor 16050. The insert comprises a restraint configured to prohibit the insert from passing completely into the working channel of the retractor. The proximal head 10660 can be wider than the distal portion of the insert 10652 to thereby restrain the insert 10652 from passing completely into the tubular retractor 10650. In some embodiments, when the proximal head 10660 abuts the top of the tubular retractor 10650, the distal end of the insert 10652 is substantially aligned with a distal end of the tubular retractor 10650 (see FIG. 3E). In some embodiments, other restraints can be used. For example, in some embodiments the restraint can include one or more protrusions from the proximal end of the insert, rather than an entire proximal head portion. In some embodiments, the restraint can include a ridge on the insert corresponding to a groove in the retractor, wherein the groove is configured to receive the ridge and to allow the insert to be slidably engaged with the retractor, while limiting the relative positions of the two. In some embodiments, the restraint can similarly include a groove in the insert corresponding to a ridge on the retractor.

Figure 6A:
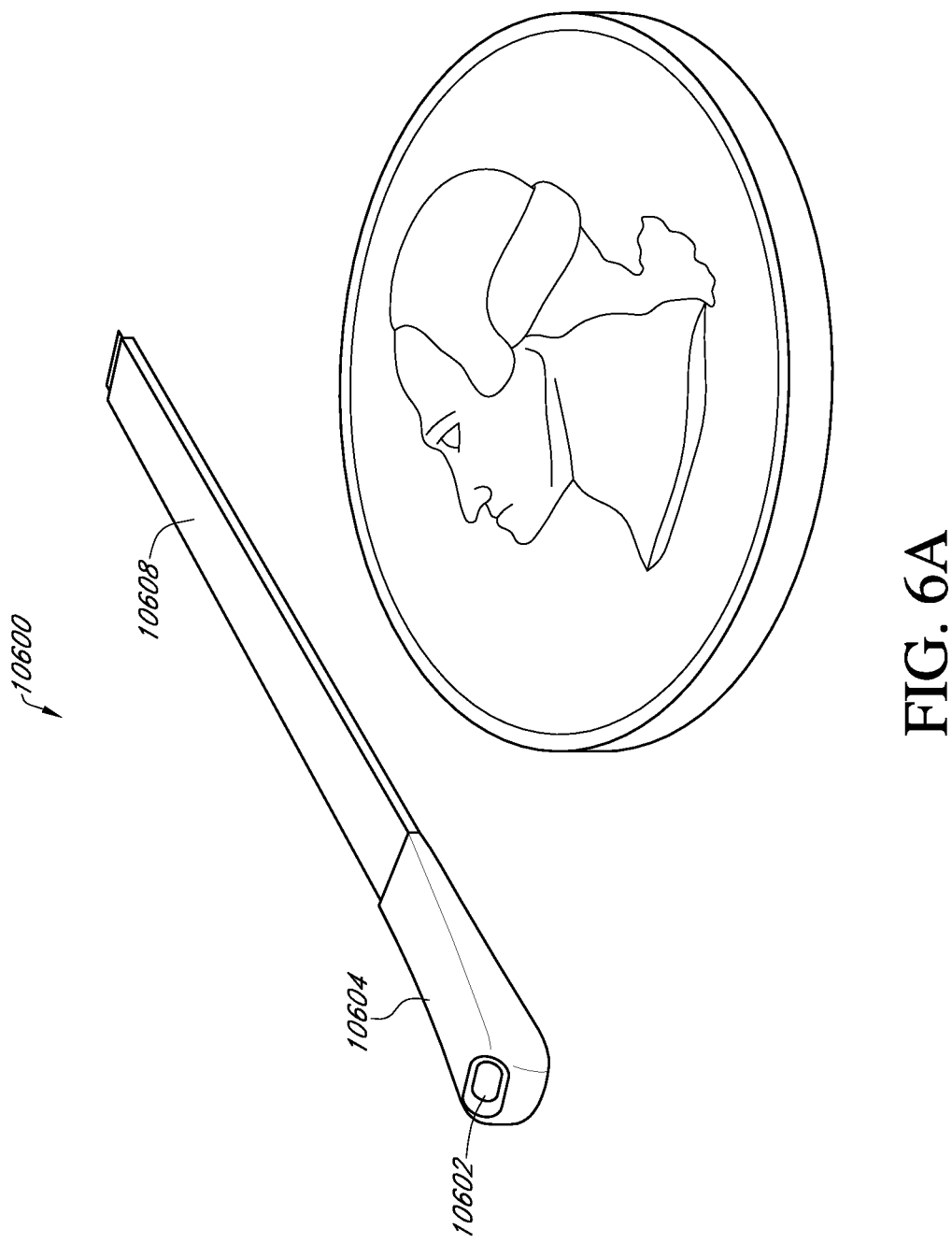
FIGS. 6A-6D are schematic illustrations of a camera module with flex cable, according to various embodiments.
Figure 6B:
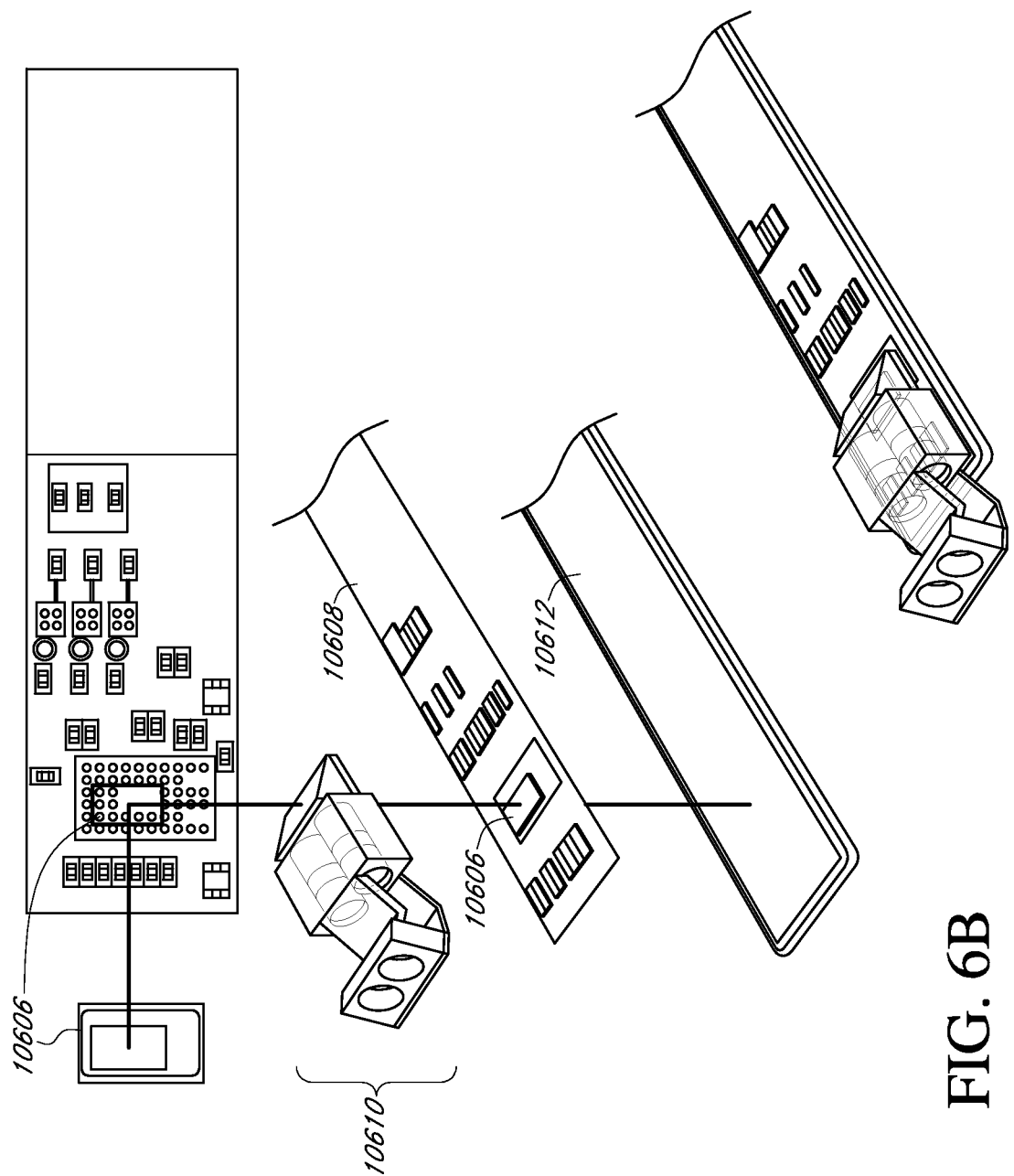
Figure 6C:
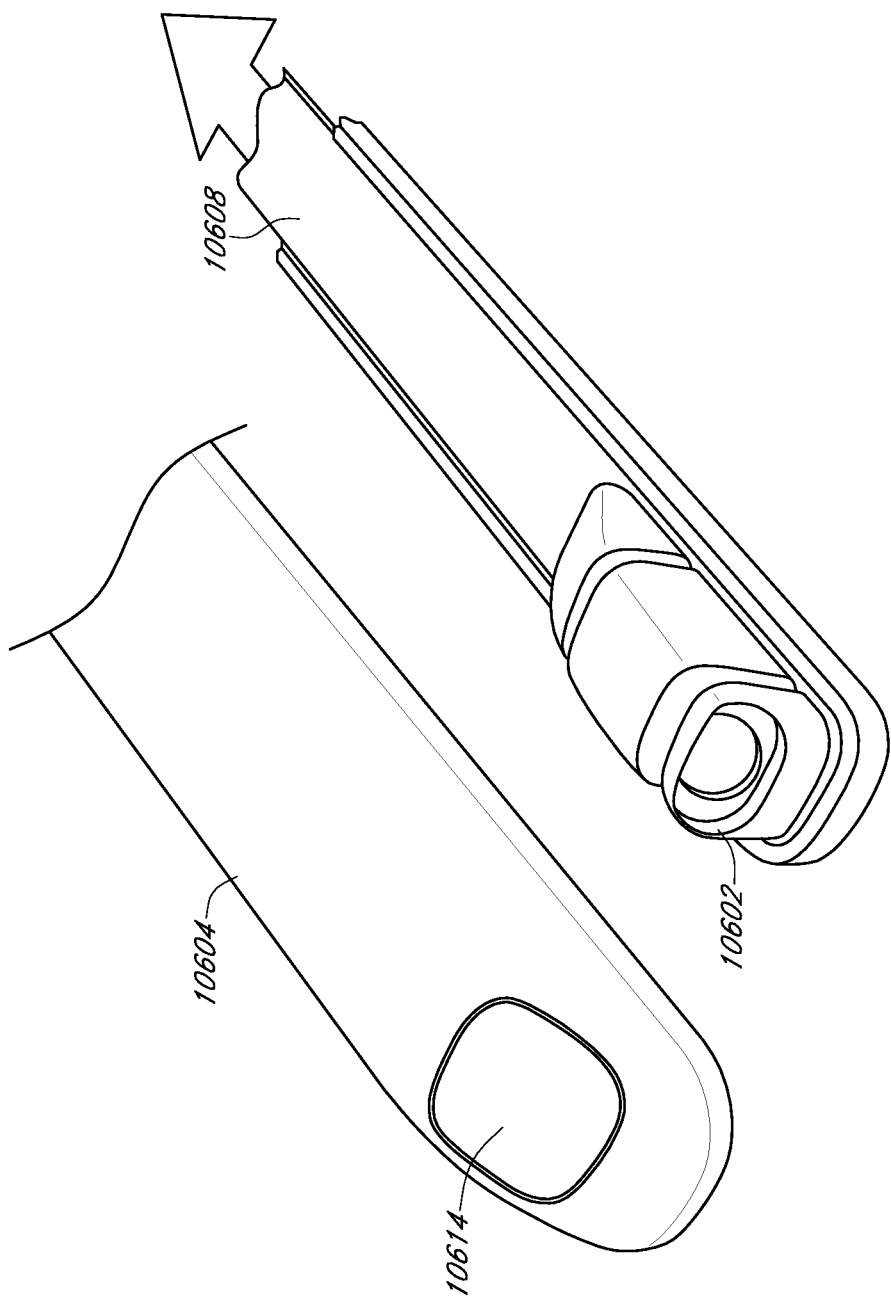

In various embodiments, the retractor may assume other shapes, and need not be tubular. For example, the retractor 16050 may be rectangular, triangular, elliptical, or may have one or more openings on a side. An upper ring 10662 on the top of the proximal head 10660 includes a plurality of slots 10664 configured to receive flex cables 10608 therein. The flex cables are described in more detail herein. In the illustrated embodiment, two flex cables 10608 are provided, each directed to a different one of the slots 10664. Associated with each slot 10664 is a rotatable knob 10666 which, when actuated, causes the flex cable 10608 to be fed into or out of the insert 10652. With actuation of the rotary knob 1066, therefore, the associated flex cable 10608 can be raised or lowered within the insert 10652, nearer or further from the distal end 10668. In other embodiments, different actuation mechanisms may be used to lower or raise the flex cables. By lowering or raising the flex cables 10608, the cameras disposed on the distal ends thereof (as shown in FIGS. 6A-C, for example) are moved closer or further from the distal end 10668. In some embodiments, a restraining bar may be provided within the proximal head 10660 to ensure that upon raising the flex cable 10608 (i.e. proximally retracting the flex cable 10608), the flex cable 10608 does not bend towards the working space of the retractor.

A plurality of connectors are provided on the proximal head 10660 of the insert 10652, including an optical fiber input port 10656, a fluid port 10670, and an air port 10672. The fluid port 10670 and air port 10672 can provide fluid, such as saline, and air to the cameras disposed on the flex cables 10608 for cleansing, drying, etc., as described elsewhere herein. In some embodiments, the insert can additionally include a port for aspiration, for example for removal of blood, saline, or other fluids from the surgical site. A rack 10674 is provided that supports the cables attached to the ports 10652, 10670, and 10672 as well as the flex cables 10608. Within the interior of the insert 10652, a plurality of illumination fibers 10676 extend downward along the length of the insert 10652. The illumination fibers 10676 carry light from the optical fiber input port 10656 and emit the light out of the distal ends of the illumination fibers 10676, as shown in FIG. 3E. The shape and dimensions of the illumination fibers 10676 can be configured to provide appropriate illumination for imaging (e.g., directionality and uniformity), while also preserving working space within the retractor. As shown, the illumination fibers 10676 can have a substantially rectangular cross-section, such that the width 10678 of the illumination fibers 10676, which extend along the circumference of the insert 10652, is longer than the depth 10680, which extends radially inward from the insert 10652. In some embodiments, the ratio of the width to the depth can be between about 1.25 and 5, between about 1.5 and 4, or between about 2 and 3. In some embodiments, the cross-sectional shape of the illumination fibers 10676 can be curved, for example semi-annular. Light passing along the illumination fibers 10676 propagates along their lengths until being emitted from the distal end. In use, the emitted light illuminates a surgical site. In some embodiments, an optical element (e.g., prism, mirror, lens, etc.) can be appended to the distal end of the illumination fiber 10676 to shape or divert the beam of light emitted from the illumination fiber 10676.

Figure 4A:
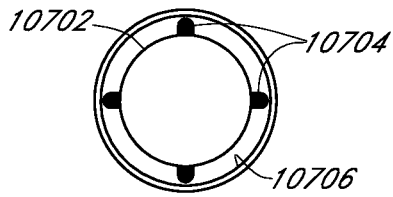
FIG. 4A shows a cross-section of a tubular insert comprising a hollow right circular cylinder having guides on the outer surface of the insert that contact the inner surface of the retractor tube.

In some embodiments, an insert comprises an upper support configured to rest above a retractor. The proximal head of the insert 10660 shown in FIG. 3B, for example, comprises such an upper support. The support is configured to receive camera modules within, thereby guiding the camera modules within the interior of the retractor. The retractor and the insert can define an interior working space, through which tools can be inserted towards a surgical site. In some embodiments, the insert can be substantially tubular. Optionally, the outer surface 10702 of the insert can include guides 10704 such as shown in FIG. 4A on the outer surface of the insert which contacts the inner surface 10706 of the retractor tube. The guides 10704 can provide for some space between the insert and the inner wall 10706 of the retractor tube. In some embodiments, the guides 10704 are configured to engage with features such as complementary shaped features on the inner surface 10706 of the (e.g. tubular) retractor, in some cases allowing for aligned insertion of the insert with respect to the retractor. For example, the outer wall 10702 of the tubular insert can include ridges configured to mate with corresponding grooves on the inner surface 10706 of the retractor, or vice versa. In some embodiments, the outer surface 10702 of the tubular insert can be configured to substantially correspond to the inner surface 10706 of the tubular retractor.

Figure 4B:
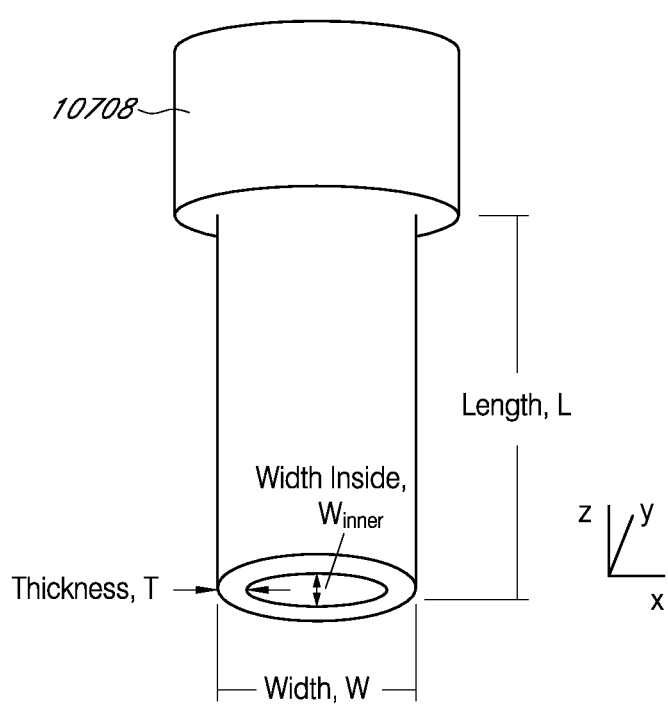
FIG. 4B shows a tubular insert in the shape of a hollow right circular cylinder as and an upper support configured to rest above a retractor.

The tubular insert can be characterized by a length and a width. For example, in the case of a tubular insert in the shape of a hollow cylinder such as a hollow right circular cylinder as shown in FIG. 4B, the length, L, is the length of the cylinder, and the width, W is the diameter of the outer surface of the cylinder. In this embodiment, the width, W, is measured at the distal end. Also, the insert comprises an upper support 10708 configured to rest above a retractor. In this case, the length, L, is measured from the distal end of the upper support 10708 where the insert is configured to enter into the retractor. In other embodiments, the tubular insert may assume other shapes, and need not be right circular cylindrical. For example, the tubular insert as seen from a cross-section orthogonal to the length (and z-axis) may be annular, elliptical, rectangular, or other shape. The cross-section may be semiannular forming half of an annulus or other fractional parts of an annulus, such as ⅓, ¼, ⅔s etc. Similarly, the cross-section may form parts of an ellipse, rectangular, or other shape.

Figure 4C:
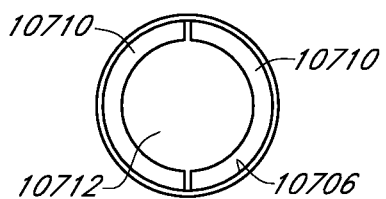
Figure 4D:
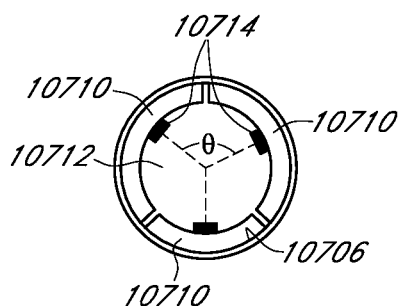

Likewise, in some embodiments, the tubular insert as seen from the cross-section orthogonal to the length thereof (and to the z-axis) may be partitioned into separate components. For example, as illustrated in FIG. 4C, two semi-annular pieces 10710 may be disposed adjacent to one another or abut one another to form the substantially tubular insert. In some embodiments, such as shown in FIG. 4D, three or more separate pieces 10710 may be positioned adjacently to provide the substantially tubular shape. In some embodiments, such separate pieces can be retained together by a support structure such as the upper support 10708 shown in FIG. 4B. In other embodiments, the separate pieces may be inserted separately into the retractor. In some embodiments, each separate piece may be configured to mate with retention features on the retractor, to maintain the separate insert piece in place.

Figure 4E:
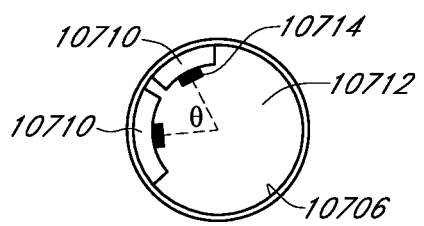

Similarly, in some embodiments, the insert may be semi-annular corresponding to only a portion of the inner surface 10706 of the tubular retractor. For example, one or two of the separate pieces 10710 may be excluded from the insert shown in FIG. 4D. Similarly, one of the separate pieces 10710 may be excluded from the insert shown in FIG. 4C. FIG. 4E shows an example embodiment of an insert having two separate pieces 10710 that cover less than ½ of the inner surface 10706 of the tubular retractor. As illustrated by FIG. 4E, the two portions 10710 can have different sizes, e.g., arc lengths, as shown in the cross-section orthogonal to the length of the insert (and z axis), which is depicted. Thus, the insert need not cover substantially all the inner surface 10706 of the tubular retractor. In some embodiments, the outer surface 10702 of the insert corresponds only to less than ⅞ of the perimeter of the inner surface 10706 of the retractor, in some embodiments less than ¾, less than ⅔, less than ½, or less than ⅓ of the perimeter of the inner surface of the retractor. However, in some embodiments, the insert corresponds to at least ⅓ of the perimeter of the inner surface 10706 of the retractor, in some embodiments corresponding to at least ½ of the perimeter of the inner surface of the retractor, in some embodiments corresponding to at least ⅔, at least ¾, or at least ⅞ of the perimeter of the inner surface of the retractor. Combinations of these ranges as well as other ranges are also possible.

In some embodiments, the length of the insert may be greater than the width of the insert. In some embodiments, this width is measured at the distal end of the insert although in other embodiments the width may be measured at the middle of the length of the insert. In some embodiments, the insert includes an upper support such as 10708 that is wider than the distal end of the insert and the length is measured from the distal end of the support structure where the insert enters the retractor. In some embodiments, the length of the insert may be least 1.1, 1.2, 1.3, 1.4, 1.5, 1.6, 1.7, 1.8, or 1.9 the width. In some embodiments, the length of the insert may be least 2, 3, 4, 5, or more times the width. In various embodiments, however, the length is less than 6, 5, 4, 3, or 2 times the width thereof. The insert may be characterized by a central opening through which tools may be inserted. In some embodiments, the central opening has a width, $W_{inner}$, of at least ⅓ of the total width, W, of the insert. In some embodiments, the central opening can have a width of at least ⅔ of the total width, in some embodiments at least ¾ of the total width, in some embodiments at least ⅞ of the total width. In various embodiments, the central opening has a width less than ¹⁵⁄₁₆, ⅞, ¾, ⅔, or ½ the total width.

In some embodiments, the insert can comprise an upper head portion (such as the upper support 10708 shown in FIG. 4B) and a plurality of elongate support structures for supporting a plurality of cameras and at least one illumination source (represented by components 10714 in FIGS. 4C-4E). Such elongate support structures may correspond to the sections 10710 shown in FIGS. 4C-4E or may be disposed thereon. In some embodiments, the insert can comprise an upper head portion and a plurality of elongate support structures for supporting a plurality of illumination sources 10714 and at least one camera 10714. In some embodiments, access can be provided for tools through the center 10712 of the insert to the surgical site. In some embodiments, the illumination sources 10714 can comprise light guides or fibers. In some embodiments, at least one camera 10714 can be disposed at a distal end of an elongate support structure, and at least one camera 10714 can be disposed proximally to the distal end of an elongate support structure. In some embodiments, a plurality of cameras 10714 disposed on the support structures can face inwards towards the working space 10712. In some embodiments, a plurality of cameras 10714 disposed on the support structures can face one another. In some embodiments, two cameras 10714 disposed on the support structures are arranged at 180 or more degrees with respect to one another. As illustrated in FIG. 4D, the cameras point in directions having an angle θ of at least 180° with respect to each other or the normals or optical axes of the cameras are directed at an angle θ of at least 180° with respect to each other. In various embodiments, the lines of sight, optical axes, or normals of the cameras 10714 converge toward a common area. The angle need not be limited to 180 or more degrees. In some embodiments, two cameras 10714 disposed on the support structures are arranged at 90 or more degrees with respect to one another, that is, the cameras 10714 point in directions having an angle θ of at least 90° with respect to each other or the normals or optical axes of the cameras are directed at an angle θ of at least 90° with respect to each other. Again, as illustrated, the lines of sight, normals or optical axes, of the cameras 10714 converge toward a common area. In some embodiments, the two cameras 10714 are arranged at at least 45 degrees with respect to one another, in some embodiments at least 30 degrees with respect to one another.

In some embodiments, the plurality of cameras 10714 comprises at least three cameras, at least four cameras, at last five cameras, or more. In some embodiments, the plurality of illumination sources 10714 comprises at least three illumination sources, at least four illumination sources, at least five illumination sources, or more. In some embodiments, the plurality of cameras 10714 comprises at least two pairs of stereo cameras, at least three pairs of stereo cameras, at least four pairs of stereo cameras, or more. The multiple stereo pairs can be arrange at angles of at least 30°, 45°, 90°, 180° with respect to each other. In some embodiments, the plurality of elongate support structures comprises at least three elongate support structures, at least four elongate support structures, at least five elongate support structures, or more. In some embodiments, the elongate support structures are configured such that when the insert is received within the retractor, the average distance separating the outer surface 10702 of the elongate support structures and the inner surface of the retractor is less than 5 mm, less than 4 mm, less than 3 mm, less than 2 mm, less than 1 mm or less and can be touching or be at least 0.2 mm, at least 0.5 mm, at least 1 mm, at least 2 mm, at least 3 mm, at least 4 mm in various embodiments. In some embodiments, the elongate support structures are configured to guide the insertion of the insert into the retractor. In some embodiments, at least one of the plurality of cameras 10714 is configured to be longitudinally movable along the length of the elongate support structure. In some embodiments, at least one of the plurality of illumination sources 10714 is configured to be longitudinally movable along the length of the elongate support structure.

In some embodiments, an insert for a retractor provides rigid support for one or more camera modules 10714 and one or more light sources 10714, wherein the insert is configured to cover at least 25% of the sidewall of the retractor. In some embodiments, the insert is configured to cover at least 35% of the sidewall, in some embodiments at least 50%, at least 60%, at least 70%, at least 80%, at least 90%, or more (e.g. 100%). In some embodiments, the insert is configured to cover at most 90% of the sidewall, in some embodiments at most 80%, at most 70%, at most 60%, at most 50%, or less. In some embodiments, a plurality of such inserts together covers at least 50% of the sidewall of the retractor, in some embodiments at least 60%, at least 70%, at least 80%, or more but may be at most 90% of the sidewall, in some embodiments at most 80%, at most 70%, at most 60%, at most 50%, or less. In some embodiments, the insert can be spaced apart from the sidewall of the retractor, on average, by less than about 5 mm, less than about 4 mm, less than about 3 mm, less than about 2 mm, or less and can be touching or be, on average, at least 0.2 mm, at least 0.5 mm, at least 1 mm, at least 2 mm, at least 3 mm, at least 4 mm in various embodiments. In some embodiments, the insert can be spaced apart from the sidewall of the retractor by on average less than about 10% of the width, W, of the insert, by less than about 5% of the width of the insert, by less than about 3% of the width of the insert, or less but can be spaced apart from the sidewall of the retractor by on average at least about 1% of the width, W, of the insert, at least about 3% of the width of the insert, at least about 5% of the width of the insert. In some embodiments the insert is generally disposed against and touches the inner surface 10706 of the retractor. In some embodiments, the plurality of inserts can together provide a central access 10712 for tools through the retractor to a surgical site.

Accordingly, in some embodiments, an insert for a retractor provides rigid support for one or more camera modules and/or one or more light sources 10714, wherein the insert has a width, W greater than its thickness, T. In some embodiments, the sidewall 10706 of the insert can be substantially arcuate or curved. In some embodiments, the sidewall 10706 of the insert is flat, linear, and/or planar. The cross-section of the insert, orthogonal to the length (and z axis as shown) can be substantially rectangular. In some embodiments, the width, W, can be at least twice the thickness, T, in some embodiments at least three times, at least four times, at least five times, or more and may be ten times or less, five times or less, four times or less, etc. In some embodiments, multiple inserts are configured to be simultaneously disposed within the retractor, the inserts together providing a central access 10712 for tools through the retractor to a surgical site. In some embodiments, a system comprises a retractor having inner sidewalls 10706, and a conformal insert having a shape corresponding to the inner sidewalls of the retractor. In some embodiments, the conformal insert has a shape corresponding to at least 25% of the inner sidewalls 10706 of the retractor. In some embodiments, the conformal insert has a shape corresponding to at least 30%, at least 40%, at least 50%, at least 75%, or more of the inner sidewalls 10706 of the retractor. In some embodiments, the conformal insert is spaced apart from the inner sidewalls 10706 of the retractor by on average less than about 5 mm, less than about 4 mm, less than about 3 mm, less than about 2 mm, or less. In some embodiments, the conformal insert is spaced apart from the inner sidewalls 10706 of the retractor by on average less than about 10% of the width of the insert, by less than about 5%, less than about 3%, or less.

Additionally, in some embodiments, an insert comprises a top head portion 10708 and a plurality of rigid elongate support structures for supporting proximal and distal cameras 10714 thereon and at least one illumination source 10714. In some embodiments, the length, L, of the support structures that is configured to extend into the retractor is greater than the width, W. In some embodiments, the length of the support structures is at least twice the width, at least three times the width, at least four times the width, or more.

Additionally, in some embodiments, an insert comprises a top head portion 10708 and a plurality of rigid elongate support structures configured to receive a camera 10714 and at least one illumination source 10714. In some embodiments, the length, L, of the support structures that is configured to extend into the retractor is greater than the width, W. In some embodiments, the length of the support structures is at least twice the width, at least three times the width, at least four times the width, or more.

Camera Modules with Flex Cable

FIGS. 6A-6D are schematic illustrations of a camera module with a flex cable, according to one embodiment. The camera module 10600 includes a camera 10602 disposed at the distal end, enclosed within housing 10604. As shown in FIG. 6B, the camera 10602 includes a sensor 10606 disposed on flex cable 10608. Optics 10610 are arranged over the sensor 10606. The flex cable 10608 is disposed on a stiffener 10612, which can be made of, for example, stainless steel or other sufficiently rigid material to support the flex cable 10608, optics 10610, sensor 10606, etc. In some embodiments, the flex cable 10608 may be overlaid with silicone or other protective material and/or potting material. As shown in FIG. 6C, housing 10604 includes a window 10614 through which the image can be taken via optics 10610 and sensor 10606. In various embodiments, the window 10614 comprises a sapphire window. In various embodiments, the housing may comprise a thin wall. In some embodiments, the housing may be made of electroformed thin wall stainless steel, and may be laser welded to the stiffener. As described in more detail below, the entire camera module 10600 can be moved proximally or distally to obtain the desired view for imaging.

Figure 6D:
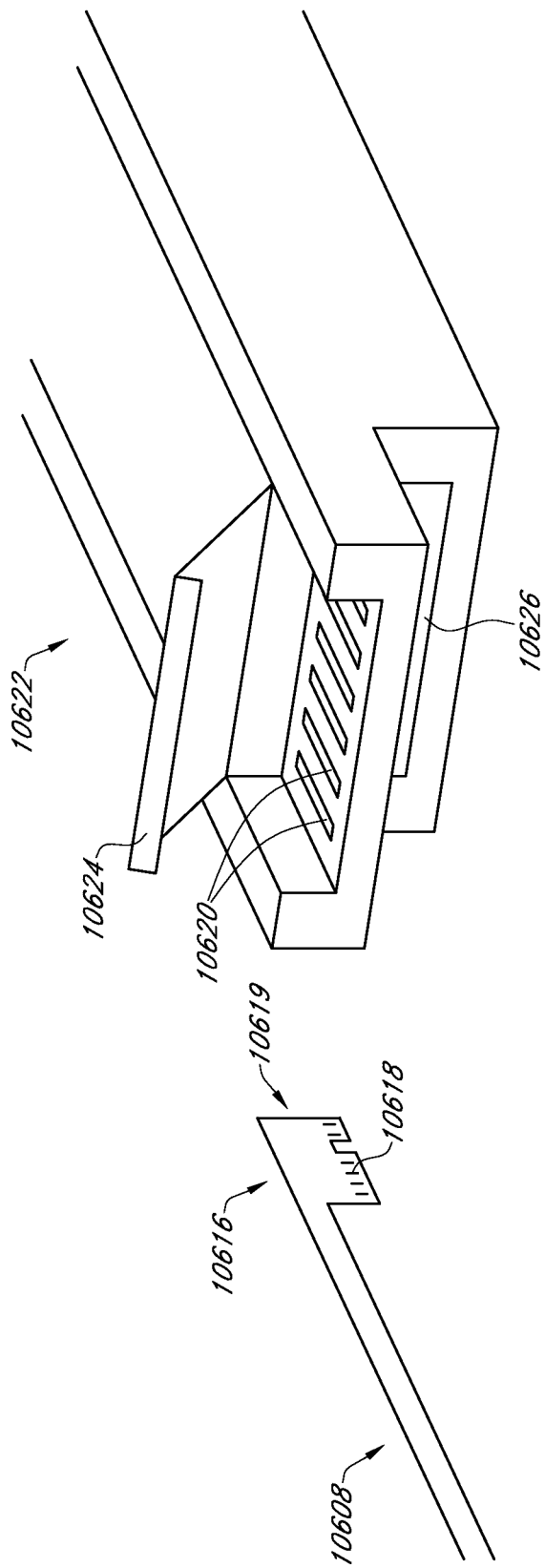

FIG. 6D illustrates the proximal end 10616 of the flex cable 10608, which includes a plurality of electrical leads 10618 on a tab 10619 extending perpendicularly from the longitudinal axis of the flex cable 10608. As a result, the L-shaped distal end 10616 can be received within vertical slots 10620 of the aggregator 10622. When received within the vertical slots 10620, electrical connection is made between the flex cable 10608 and the aggregator 10622. A lid 10624 can be disposed over the vertical slits 10620 to protect the upward facing electrical connections. An open channel 10626 in the aggregator 10622 can be configured to receive fluidics lines, fiber optic cables, or other components. In the illustrated embodiment, the open channel 10626 is disposed beneath the electrical connector slits 10620. However, in other embodiments the open channel may be arranged next to or above the electrical connector slits.

In some embodiments, the cameras on the retractor blades or flexible cable can be tilted, for example, upward or downwards or sideways or combinations thereof. The cameras can be tilted to achieve different orientations of the camera. For example, in some embodiments, the cameras can be tilted with the use of hydraulic balloon, diaphragm, or bellows actuated pistons thereby orienting the camera in different positions relative to the retractor blade. The tilt of the camera can be changed prior to or during a surgical procedure. For example, the cameras can be positioned on a stage and the stage can be tilted with the use of hydraulic balloon, diaphragm or bellows actuated pistons thereby orienting the camera in different positions relative to the retractor blade. In some embodiments, the cameras on the retractor blades can be situated on a track that allows the camera to move vertically (and/or laterally) on the retractor blade thereby changing the position of the camera. Such a vertical position can be set prior to surgery or during surgery. The positioning may be performed manually or by using an actuator, such as a motor or other actuator.

In some embodiments, the camera module position and orientation with respect to the retractor can be controlled, for example, remotely controlled. The camera may be manipulated to tilt or move vertically or horizontally with respect to the retractor. Electrical, manual mechanical, or other means can control and/or drive the position or orientation of the camera. In some embodiments, the camera movement can be provided by an electro mechanical device such as a piezo or other actuator. In some embodiments, the camera movement can be provided by one or more Micro-Electro-Mechanical System (MEMS) actuators. In some embodiments, however, MEMS devices may encounter limitations with regard to autoclaving and exposure to water.

Figure 7A:
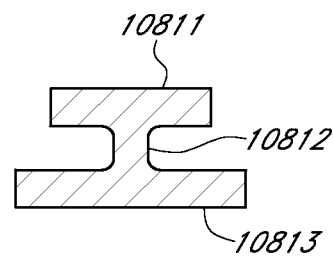
FIG. 7A illustrates a cross-sectional view of an embodiment of a flexible mount for a camera on a retractor.

In various embodiments, the camera modules can be positioned using a movable mechanical device or system that is manually controlled. FIG. 7A illustrates a cross-sectional view of an embodiment of a flexible joint or hinge 10812 having a camera platform 10811 and a retractor connector surface 10811. The flexible joint can be a flexible revolute joint or hinge that allows the camera to move relative to the rigid structure of the retractor and/or retractor mounted connection surface 10813. In various embodiments, the flexural revolute joint can provide one degree of freedom such as pitch variation. The flexural element can promote correct alignment, may have reduced or no stiction, and may be inexpensive and compact. In some embodiments, the camera platform 10811 can have attached push-pull cables, rods or other members 10814. The push-pull rods or members 10814 can allow for movement of the camera 10811 relative to the retractor blades 10813. The movement of the camera can result from tension (or pressure) forces exerted on a portion of the camera platform 10811 which creates flexing of the flexible joint 10812. Once the tension (or pressure) is released, the flexible joint allows the camera platform 10811 and camera thereon to return to the unflexed position.

Figure 7B:
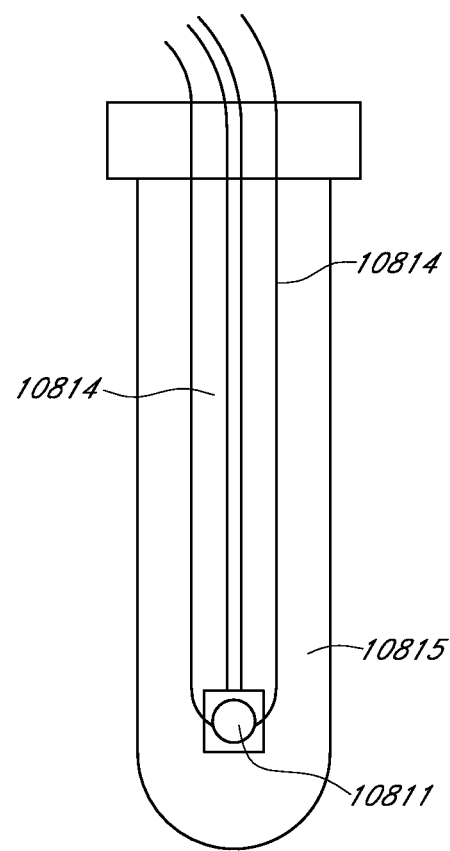
FIG. 7B illustrates an embodiment of the retractor blade, camera, and movement cable system for moving a camera with respect to a retractor blade.

As illustrated in FIG. 7B, in some embodiments, the cables 10814 (or rods or others members) are connected to a knob or crank 10816 positioned at a proximal or top end of the retractor or retractor blade 10815. Movement of the knob 10816 creates the force used to actuate the push-pull cables, rods, or members 10814 and provides the movement and locking mechanisms for the cables 10814. One set of push-pull cables, rods, or members 10814 can be provided on each side of the camera platform 10811 to allow movement about a vertical axis of the joint. Such a configuration can allow for one degree of freedom movement of the camera and camera platform 10811. In some embodiments, additional push-pull cables, rods, or members 10814 can be provided to support movement of the camera 10811 in additional directions. For example, a second set of push-pull cables, rods, or members 10814 can be attached to the top and bottom portions of the camera platform 10811. Actuation of these cables 10814 can provide movement of the camera platform 10811 about the horizontal axis. In some embodiments, a flexural gimbal having two degrees of freedom, such as pitch and yaw, may be used. In some embodiments, the hinge, pivot, or joint can be a ball joint or a jeweled pivot. In some embodiments, the linear motion of the push-pull cable, rod, or member (e.g., the pull motion on a flexible joint) can drive a wedge to create angular motion of the camera with respect to the retractor element 10815. In some embodiments, instead of or in addition to a push-pull cable, rod or member, a pull cable, rod or member for pulling (or pushing) can be used with a joint such as a flexural revolute joint that has a flexural spring return.

As described above, in some embodiments, the movement is provided with electrical actuators. Instead of manually turning a knob or crank, for example, a motor or other electro-mechanical actuator could be used to drive the motion.

Additionally, in some embodiments, the camera can be actuated pneumatically or hydraulically. Pressurized air or saline can allow for remote actuation of the camera. Bellows or diaphragms may be used to provide the force necessary to rotate or tilt the camera with respect to the retractor blade. The pneumatic or hydraulic actuation requires no motors and has greater compatibility with EM tracking devices as described herein. In some embodiments that do not employ a MEMS actuation device, autoclaving can be employed and water damage issues are alleviated.

Foot Pedal and Frame

FIG. 8A is a schematic illustration of a surgical visualization system including a foot pedal. In some embodiments, a foot pedal 10801 may be provided for use with the console 10001. The foot pedal 10801 can be positioned adjacent to the console 10001 and within the reach of the foot of a medical professional 10029, 10031 during use. In some embodiments, the foot pedal 10801 can communicate with the console 10001 through a connection provided by, for example, a foot pedal cable 10802. When the foot pedal 10801 is depressed, the foot pedal 10801 provides an output signal through the foot pedal cable 10802. The output signal can allow for control, movement, actuation, or other functionalities provided by the associated console mechanisms, various of which are described herein. The foot pedal 10801 and foot pedal cable 10802 can provide for communication with the console 10001 to allow for the medical professional to remotely control the various functions associated with the console 10001. In some embodiments, the cable 10802 can be excluded and communication between the foot pedal 10801 and console 10001 can be provide, for example, wirelessly.

The foot pedal 10801 can activate or control the functions associated with or connected to the console 10001. During surgery, a medical professional 10029, 10031 can depress or otherwise activate the foot pedal 10801. In some embodiments, such activation can provide for activation or communication with an associated hydraulic, mechanical, or electrical system. For example, the activation of the foot pedal 10801 by depressing the foot pedal 10801 can start a hydraulic circuit similar to one that can also control the tools or camera cleaning components as described herein. The foot pedal can be used to control the hydraulic system. In some embodiments, the foot pedal 10801 can be used to operate surgical devices such as a surgical retractor, camera, or tools such as, Kerrison, forceps, or any other tools as disclosed or described herein. Additionally, thereon some embodiments, the foot pedal can be used to control fluid and/or air pulses over the surface of the cameras or for use in the surgical area.

In some embodiments, the foot pedal 10801 can be a proportional foot pedal that allows for proportional control of the associated mechanism. For example, the speed or force applied by a tool can be proportional to the depression or force applied by the medical professional to the foot pedal 10801. Similarly, increasing depression of the foot pedal, for example, can close the tool by a proportional amount. Additionally, in some embodiments, surgical impedance feedback can be incorporated as described previously. Increased resistance felt by the surgical tool can be communicated to the operator by an increased resistance in the depression of the foot pedal. This allows the medical professional to receive a tactile response to the resistance of the tool even though the tool is operated by a remote foot pedal.

One or more foot pedals can be utilized to control one device. The multiple foot pedals can provide for control of different parameters of a device. In some embodiments, the one or more foot pedals can each operate or control different tools. One foot pedal can operate one device while a second foot pedal can control a second device. Therefore the medical professional can utilize two tools actuated by foot pedals and allowing his or her hands to be free to perform other functions. In various embodiments, one or more of these foot pedals may be proportional foot pedals and may provide tactile feedback.

As illustrated in FIG. 8B, in some embodiments, the multiple foot pedals 10801 can be located within the same frame 10803. The single frame 10803 housing the multiple foot pedals 10801 can provide for easy movement and positioning of the foot pedals in a close proximity to the medical professional without unnecessary crowding or reaching required by the surgeon. In various embodiments, one or more of these foot pedals may be a proportional foot pedal and may provide tactile feedback.

Driver Boards Inside the Console

In some embodiments, the console 10001 can contain driver boards for controlling various surgical tools. Some embodiments further comprise a foot pedal, which can send a signal to a driver board in the console 10001 upon user actuation of the foot pedal. Upon receiving a signal from the foot pedal, the driver board can control various parameters of the surgical tools, such as power. In some embodiments, the foot pedal is proportional, so that the degree to which the foot pedal is depressed correlates to the amount of power supplied to a surgical tool and/or the result, e.g., the amount of movement, the speed, etc. Thus, for example, if the foot pedal is depressed to its maximum displacement (e.g., to the floor) the driver board can cause the surgical tool to operate at maximum power. Continuing the example, if the foot pedal is depressed to half its maximum displacement, the driver board can cause the surgical tool to operate at half the maximum power.

In some embodiments, the console 10001 can contain an ultrasonic driver board for driving an ultrasonic tissue aspirator. The ultrasonic tissue aspirator can be used for various surgical procedures and operations, such as brain tumor debulking. Brain tumor debulking can be facilitated by various aspirator hand pieces, which can also be driven by the ultrasonic driver board inside the console 10001. The aspirator hand pieces can be reusable according to some embodiments. In some embodiments, ultrasonic power can be controlled via a proportional foot pedal. For example, depressing the foot pedal can send a signal to the ultrasonic driver board in the console 10001 to deliver power to the ultrasonic tissue aspirator in proportion to the degree to which the foot pedal is depressed.

In some embodiments, one foot pedal may control both the aspiration level and the ultrasonic power level of the ultrasonic tissue aspirator. In some embodiments, depressing the foot pedal may cause the aspiration level and the ultrasonic power level to increase simultaneously and proportionally. In other embodiments, the aspiration level and the ultrasound power level may not increase simultaneously and/or proportionally. For example, a first depression of the foot pedal (e.g., depressing the foot pedal to half its maximum displacement) may increase the aspiration level while the ultrasound power level remains constant. A second depression of the foot pedal (e.g., depressing the foot pedal from half its maximum displacement to its full maximum displacement) may increase both the aspiration level and the ultrasound level proportionally. In other embodiments, the sequence may be reversed. Thus, a first depression of the foot pedal may increase the aspiration level and the ultrasound power level proportionally, and a second depression of the foot pedal may increase the aspiration power level while the ultrasound power level remains constant. In various embodiments, software may be provided which can be programmed to control the relation between the aspiration level and the ultrasound power level that is output when the foot pedal is depressed.

In some embodiments, the ultrasonic driver board may introduce noise, which may disturb the video output signal from the cameras on the retractors. In order to minimize noise introduced to the video camera output signal by the ultrasonic driver board, the ultrasonic driver board can be shielded and separated from the other electronic components in the console, such as the flex cables from the cameras on the retractors. Additionally, the surgical visualization system may include a filter configured to filter out the unwanted components of the video from the cameras. Because the noise introduced by the ultrasonic driver boards may be at a particular frequency, a notch filter can be used, the notch being at a dominant frequency of the noise (e.g., at 23 kHz and/or 36 kHz). This notch filter may be included with electronics for the surgical visualization system such as electronics on the console and may be in electronics on the console arm such as the distal end of the console arm, e.g., in the CIB. The notch filter may comprise one or more digital or analog filters. In some embodiments, the notch filter is included in a processor. In some embodiments, the notch filter is included with amplifier circuitry.

In some instances, a phase-locked loop can be employed to remove noise introduced by the ultrasonic driver board. In particular, the phase-locked loop can be used to synchronize a version of the output signal from the ultrasonic driver board with the output video signal of the cameras, such that the noise contribution to the video signal resulting from the ultrasonic driver board can be removed or at least reduced. In various embodiments, for example, the ultrasonic driver board generates an oscillating signal at a particular frequency (e.g., at 23 kHz and/or 36 kHz) as well as potentially some harmonics. This oscillating signal can introduce noise having similar frequency components into the video signal produced by the camera. In an effort to cancel out this noise, an output signal of the ultrasonic driver board at this frequency (and possibly including the harmonics) can be compared to the video output signal from the cameras, or a facsimile thereof using the phase-locked loop. The phase-locked loop can then lock onto the frequency and phase of the two signals. The phase-locked loop would then be used to produce an output similar to the ultrasonic driver board signal but with a frequency and phase that matches the output video signal of the cameras. This phase-locked signal can then be subtracted from the video signal output by the cameras so that noise in the video introduced by the ultrasonic driver board can be removed or at least reduced. In some embodiments, an adaptive filter can be used to provide the correct amplitude of the noise to be subtracted out of the video signal. The ultrasonic driver board, in some embodiments, drives an ultrasonic tissue aspirator, which can be coordinated with a precision suction system. The precision suction system can be used for various surgical operations. For example, the suction system can be used near fragile veins with precise control of very low vacuum levels. The suction system can also be used near ruptured aneurysms where high vacuum levels can be used for suctioning blood. Suctioned blood and tissue can be transferred to disposable canisters according to some embodiments. In addition, the suction system can be used with conventional medical devices, such as reusable and disposable cannulas. The suction system can also be coordinated with the ultrasonic tissue aspirator.

In some embodiments, the power and/or vacuum level of the precision suction system can be controlled via a proportional foot pedal. Some embodiments include a proportional foot pedal for the precision suction system, and a separate proportional foot pedal for the ultrasonic tissue aspirator. In other embodiments, one proportional foot pedal can be used to control both the ultrasonic tissue aspirator or other tools and the precision suction system. In these embodiments, an auditory command, a gesture, a touch input, or the like can be used to select the surgical tool controlled by the proportional foot pedal.

Some embodiments of the console include a radiofrequency (RF) driver board in the console 10001. The RF driver board can be configured to drive bipolar radiofrequency (RF) coagulation and cutting tools as well as bipolar forceps. In some embodiments, the coagulation and cutting tools are disposable. In order to reduce charring and sticking, in some embodiments the bipolar forceps can be irrigated with pressurized saline from the console 10001. Saline irrigation can further be utilized to clean the bipolar forceps as well as other surgical tools.

A proportional foot pedal can be used to control the bipolar RF coagulation and cutting tools and the bipolar forceps. For example, depressing the proportional foot pedal can send a signal to the RF driver board causing the RF tools to operate with more or less power, in proportion to the degree to which the foot pedal is depressed. Some embodiments include a proportional foot pedal in communication with the RF driver board and a separate proportional foot pedal in communication with the ultrasonic driver board. Other embodiments include one foot pedal in communication with both the RF driver board and the ultrasonic driver board.

According to some embodiments, the RF driver board can support multiple modulation formats. Thus, one RF driver system included in the console can support multiple RF surgical tools and their respective modulation formats. The RF driver board, may for example, comprise a processor and/or other electronics configured to provide signals with the desired formatting. Amplifiers may be used as well to provide the desired formatting. In various embodiments, a format is selected and the processor or electronics adjusts so as to output the suitable format. The format selected may vary for different surgical tools, tool types, manufacturer's etc. Selection may be provide by the surgeon, a technician, a nurse, or another medical professional. In some embodiments, the selection may be provided by RFID, EEPROM or other coding associated with the tool such that the presence or connection of the tool activates selection of the proper format. The electronics in the RF driver reconfigures the output to be consistent with the selected format. Thus, despite different modulation formats for different RF surgical tools, only one RF driver system, which may be included in the console, may be used to drive the RF surgical tools.

As discussed above, in various embodiments, footpedals may be used to provide control, such as proportional control of electronics, hydraulics, tools, suction, and other functions or combinations of functions. Foot pedals are beneficial because control can be provided without employing the hands, which can be used for other aspect of the surgery. In certain embodiments, however, other types of controls other than foot pedals may be used. In some embodiments, the RF driver board may introduce noise, which may disturb the video output signal from the cameras on the retractors. In order to reduce of minimize noise introduced to the video camera output signal by the ultrasonic driver board, the ultrasonic driver board can be shielded and separated from the other electronic components in the console, such as the flex cables from the cameras on the retractors. Additionally, the surgical visualization system may include a filter configured to filter out the unwanted components of the video from the cameras. Because the noise introduced by the RF driver board may be at a particular frequency, a notch filter can be used, the notch being at a dominant frequency of the noise. For example, in some embodiments, the RF driver board may introduce to the video camera output signal a noise frequency of about 300-500 kHz with a modulation scheme of approximately 30 kHz and other harmonics that may be introduced by, for example, changes in the impedance of the tissue surgical site. Therefore, in these embodiments, the notch filter may be configured to filter out from the video camera output signal the dominant frequency, which may be about 500 kHz. In some embodiments, the noise introduced by the RF driver board may be at relatively high frequencies, such as 400 kHz to 3.5 MHz. Therefore, in some embodiments the surgical visualization system can include a low pass filter to remove these relatively high frequency noise signals from the video camera output signal.

This notch filter or low pass filter may be included with electronics for the surgical visualization system such as electronics in the console and may be electronics in the console arm such as the distal end of the console arm, e.g., in the CIB. The notch filter or low pass filter may comprise one or more digital or analog filters. In some embodiments, the notch filter or low pass filter is included in a processor. In some embodiments the notch filter or low pass filter is included with amplifier circuitry.

In some instances, a phase-locked loop can be employed to remove noise introduced by the RF driver board. In particular, the phase-locked loop can be used to synchronize a version of the output signal from the RF driver board with the output video signal of the cameras, such that the noise contribution to the video signal resulting from the RF driver board can be removed or at least reduced. In various embodiments, for example, the ultrasonic driver board generates a signal at a particular frequency (e.g., at 500 kHz) as well as potentially some harmonics. This signal can introduce noise having similar frequency components into the video signal produced by the camera. In an effort to cancel out this noise, an output signal of the RF driver board at this frequency (and possibly including the harmonics) can be compared to the video output signal from the cameras, or a facsimile thereof using the phase-locked loop. The phase-locked loop can then lock onto the frequency and phase of the two signals. The phase-locked loop would then be used to produce an output similar to the RF driver board signal but with a frequency and phase that matches the output video signal of the cameras. This phase-locked signal can then be subtracted from the video signal output by the cameras so that noise in the video introduced by the RF driver board can be removed or at least reduced. In some embodiments, an adaptive filter can be used to provide the correct amplitude of the noise to be subtracted out of the video signal. Paragraphs [0883]-[0898] and claims 111-115 from each of U.S. Prov. App. No. 61/880,808, U.S. Prov. App. No. 61/920,451, U.S. Prov. App. No. 61/921,051, U.S. Prov. App. No. 61/921,389, U.S. Prov. App. No. 61/922,068, and U.S. Prov. App. No. 61/923,188 are incorporated by reference herein.

Distal Proximal Camera with Prism

Figure 5A:
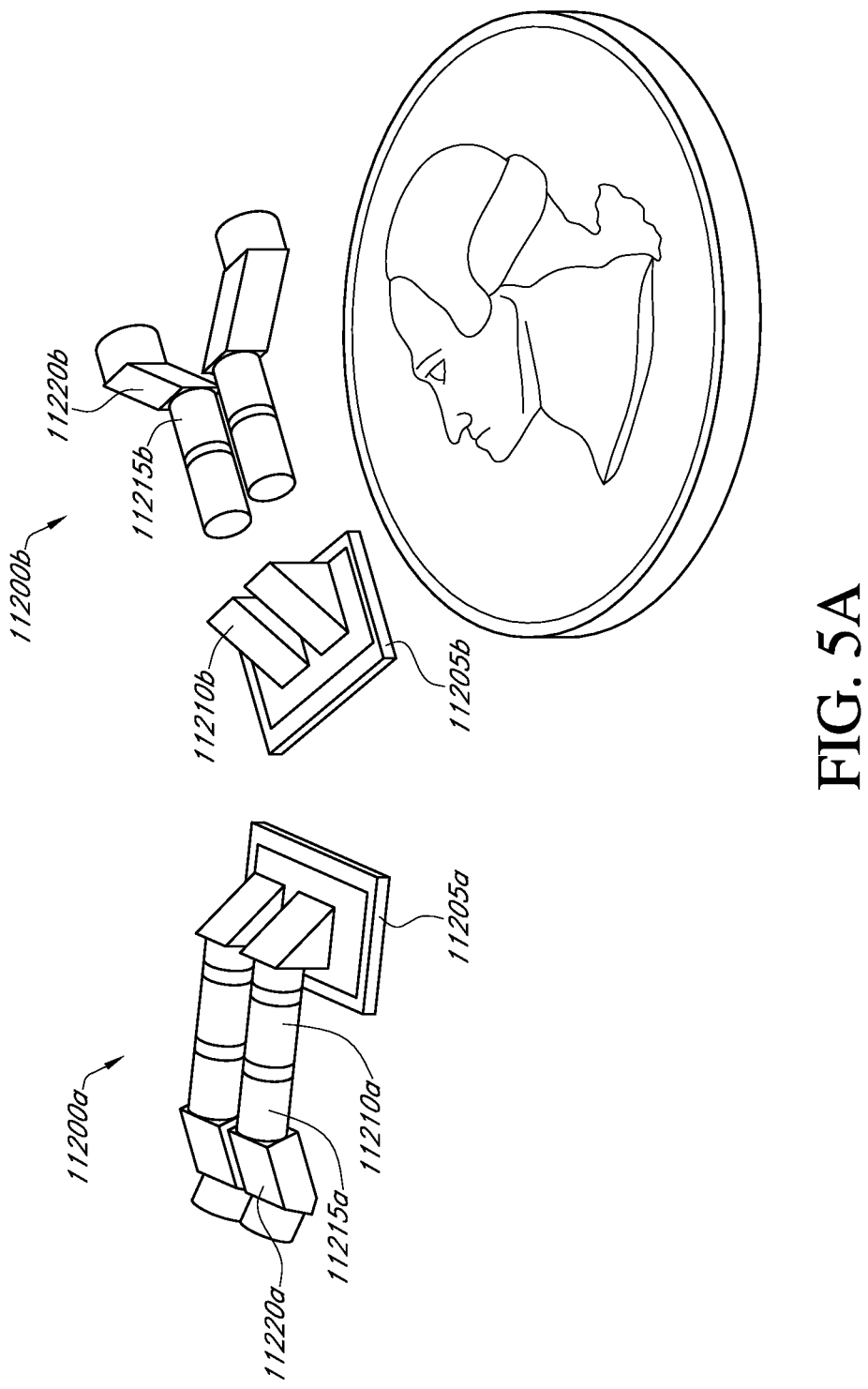
FIG. 5A illustrates example embodiments of stereo optical assemblies for proximal and distal cameras on the retractor.

As illustrated in FIG. 5A, in various embodiments the cameras located on the retractor can be configured to provide stereo imaging. A pair of lenses or lens trains may be included with a pair of optical sensors (or separate portions of a single optical sensor). The lenses form images on the image sensor(s). The pair of lens or lens trains and optical sensor(s) can mimic a pair of eyes providing stereo acquired depth perception.

In various embodiments, the cameras can additionally include one or more distal optical elements (e.g., a prism) configured to redirect an optical path or primary optical axis from being parallel with a mechanical axis (e.g., a longitudinal axis of a cable forming part of a camera module) to point inward relative to the mechanical axis. The inward pointing angle can be at least 0.1° and/or less than or equal to about 90°, at least about 15° and/or less than or equal to about 75°, or at least about 30° and/or less than or equal to about 45°. The optical subassembly can include one or more proximal optical elements (e.g., a prism) to fold the optical path of the optical assembly to be parallel with the mechanical axis (e.g., the longitudinal axis of the cable).

In various embodiments, the optical subassembly can include distal optical elements (e.g., prisms) to further separate stereo optical paths to approximate an interpupillary distance, which may in some embodiments, be similar to that provided by an operating room microscope. For example, for a close working distance (e.g., 10 mm, 15 mm, 20 mm, 25 mm) the adjacent right eye and left eye separation can be placed side by side with the lens trains side by side with front collection surface side by side. In some embodiment, a single image sensor can include masking to separate portions of the sensor for the respective lens trains. In various embodiments, a center-to-center distance between the front collection surface, for the respective left and right imaging optics, divided by the above working distances approximates the convergence physicians are familiar with such as while using such operating room microscopes. For larger working distances (e.g., approaching between about 75 mm and 100 mm), the center-to-center separation can be increased by using deviating prisms configured to separate the front collection surface and/or entrance pupils. See, for example, the stereo optical assemblies 11200*a*, 11200*b* can be used respectively as proximal and distal cameras mounted on a retractor.

With regard to masking the sensor, in some embodiments, portions of the image sensor can be electronically mapped (e.g., through electronics or image processing methods) as left and right sides of the image sensor for the respective left and right channels of the stereo camera optics. As discussed above, in some embodiments, a center-to-center distance between the left and right sides, divided by the working distance, can be adjusted to approximate the convergence accustomed to by a surgeon. In some embodiments, the parameters are selected to approximate the convergence typical operating room microscopes. The electronic masks can be used to create left- and right-eye views using circular electronic mask openings, square electronic mask openings, or some other shape for the electronic mask openings. In some embodiments, the electronic mask openings can be movable along an axis of the sensor (e.g., a vertical or horizontal axis) to control convergence. The distance between the electronic mask openings can be controlled by a user through user interface elements on the display, such as a graphical user interface. The size of the masks (e.g., a diameter), can be electronically fixed in a non-transitory storage medium (e.g., an EPROM), and may be fixed or adjustable. The distance between the electronic mask openings can be configured according to one or more targeted or suitable effects such as, for example, alignment error correction, dead pixel masking, or the like.

FIG. 5A illustrates example embodiments of stereo optical assemblies 11200a, 11200b comprising lenses and prisms. The stereo optical assemblies 11200a, 11200b include image sensors 11205a, 11205b divided into a left-side and a right-side for producing corresponding left-side and right-side stereo images. The stereo optical assemblies 11200a, 11200b include first redirection optics 11210a, 11210b to fold the optical axis along a path that is substantially perpendicular to the plane of the image sensors 11205a, 11205b. The stereo optical assemblies 11200a, 11200b include imaging optics such as lens trains 11215a, 11215b comprising one or more optical elements configured to image a scene onto the image sensors 11205a, 11205b. These one or more optical elements may comprise one or more lenses, which may optically comprise one or more rod lenses. The stereo optical assemblies 11200a, 11200b include second redirection optics 11220a, 11220b configured to define or provide a convergence angle, a field of view, and/or a line of sight for the stereo optical assemblies 11200a, 11200b.

In some embodiments, the second redirection optics 11220a can be configured to redirect the left- and right-side optical axes from a path that is substantially parallel with a mechanical axis of the structure with which it is associated to an axis that is between about 10 degrees and about 75 degrees, between about 20 degrees and about 60 degrees, or between about 30 degrees and about 45 degrees from coaxial with that mechanical axis. In some embodiments, the second redirection optics 11220b can be configured to separate left and right optical paths to an approximate inter-pupilary distance to provide stereo imaging for three-dimensional viewing. In certain embodiments, the second redirection optics 11220b can be configured to separate optical paths to an approximate inter-pupilary distance of a typical operating room microscope. For relatively close working distances (e.g., about 10 mm, 15 mm, 20 mm, or 25 mm), the adjacent right-eye and left-eye separation on the image sensor, with an optical physical or electronic mask, can be sufficient for the inter-pupilary separation distance. For longer working distances (e.g., at least about 75 mm and/or less than or equal to about 100 mm), the second redirection optics 11220b can be used to change the effective separation of the left- and right-eye views. In such a case, the line of sight of the proximal cameras can be decreased to be between about 30 degrees and about 50 degrees for viewing into, as opposed to within, a surgical or anatomical site. Accordingly, camera optics providing a line of sight of between about 30 degrees and about 50 degrees may be used in such cases. In various embodiments, the left and right views in side-by-side arrangement and adjusting the spacing therebetween to provide the desired convergence can reduce keystone distortions that would be cause by alternatively tilting the pair of camera views with respect to each other to provide the desired convergence.

As discussed above, in some embodiments, the stereo optical assemblies 11200a, 11200b can be used respectively as proximal and distal cameras mounted on a retractor. The stereo optical assemblies 11200a, 11200b can be mounted at the same azimuthal angle with respect to the surgical site, e.g., both at 12 o'clock, 3 o'clock, 6 o'clock, 9 o'clock, or points in between. The stereo optical assemblies 11200a, 11200b can be configured to have their optical axes generally align with the gravity vector when mounted to a retractor. In some embodiments, the angles of the optical axes can be different from one another, or non-parallel.

Stereo Camera Design

Figure 5B:
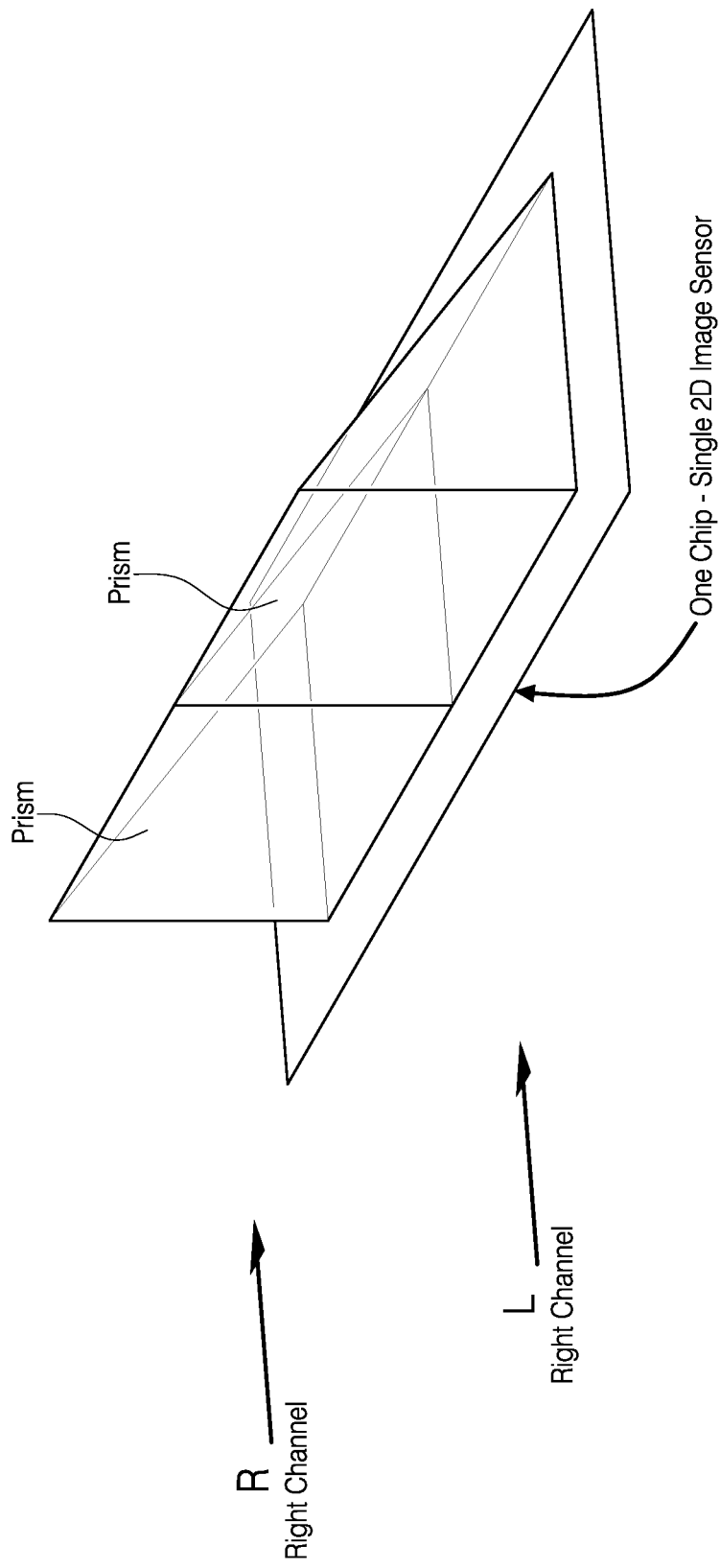
FIG. 5B illustrates an example two-dimensional image sensor with a pair of prisms and a single chip employed for stereo camera.

As discussed above, in various embodiments a single two-dimensional image sensor can be employed for a stereo camera. Separate optics, e.g., lens trains, for left (L) and right (R) channels can be directed to the single two-dimensional image sensor as shown in FIG. 5B. The two-dimensional image sensor may comprise, for example, a CCD or CMOS detector array. A pair of prisms or separate portions of a single prism may be employed to direct the beam from the lens train (not shown) for the respective left (L) and right (R) channels onto the single detector array.

Figure 5C:
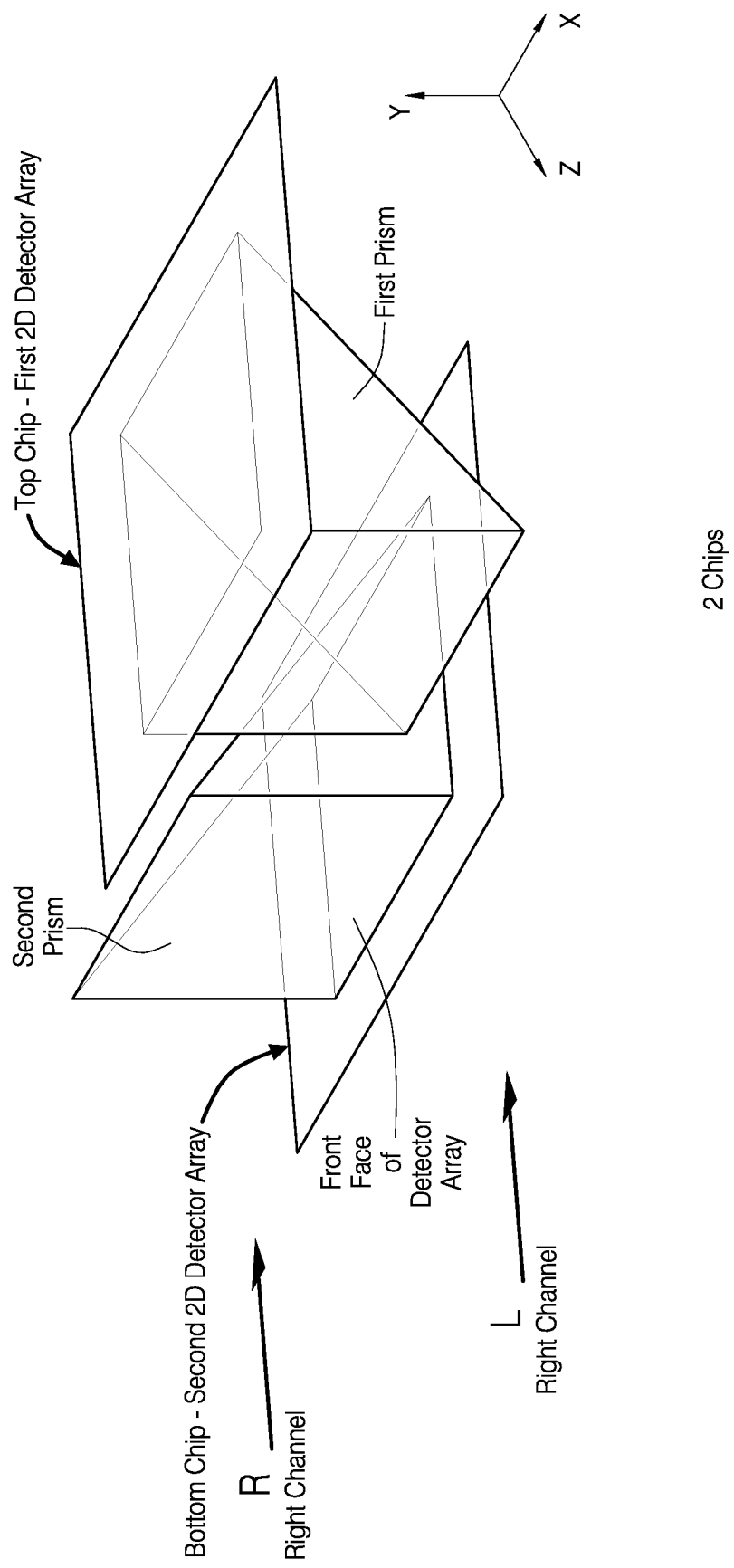
FIG. 5C illustrates an example two-dimensional image sensor with a pair of prisms and two chips employed for stereo camera.

Alternatively, more than a single chip can be employed. In particular, first and second two-dimensional detector arrays can be disposed to receive the left (L) and right (R) channels respectively as illustrated in FIG. 5C. In the embodiment shown, first and second prisms receive light from first and second lens trains (not shown) corresponding to the left and right channels, respectively of the stereo camera. The first and second prisms turn the light onto the front face of the respective first and second two-dimensional detector array (e.g., CCD or CMOS detector arrays). Light is thus received at the front face of the detectors for converting into an electrical signal and transforming an optical image into data to create an electrical image.

In the configuration shown, the first detector array is disposed above (e.g., in the +Y direction) and is offset laterally (e.g., in the X direction) with respect to the second detector array. Additionally, the active area of the chip for the first detector array faces (e.g., in the −Y direction) while the active area of the chip for the second detector array faces (e.g., in the +Y direction.)

Likewise, the first and second prisms are oriented oppositely as well as being disposed laterally with respect to each other. For example, the first prism is disposed in the X direction with respect to the second prism. Moreover, in the embodiment shown, the first and second prisms comprises right angle prisms, however, the first prism is flipped upside-down with respect to the second prism. Each of the first and second prisms have primary reflective faces that receive light from the lens train and direct the light to the active region of the 2D detector array chip. Because the second 2D array is below the prism while the first 2D array is above the prism, the reflective surface of the two prisms are orthogonal to each other. Accordingly, the reflective surface of the second prism reflects incoming light from the optics train downward (e.g., in the −Y direction) to the detector array thereunder. In contrast, the reflective surface of the first prism reflects incoming light from the optics train upward (e.g., in the +Y direction) to the detector array thereover.

Advantageously, this arrangement enables the two detector array chips to be in close proximity of each other providing a more compact design. Variations are possible. For example, the prisms need not be right angle prisms. For example, the primary reflective surface need not be at an angle of 45 degrees with respect to the front face of the 2D sensor arrays. Additionally, different types of prisms and/or reflective surfaces can be employed. Other variations are also possible.

In comparison to the embodiment shown in FIG. 5B, in some cases, the embodiments shown in FIG. 5C offers the ability obtain higher resolution. For example, the full set of available usable pixels for two separate higher resolution chips, one for each of the left and right channels, may be employed in the configuration shown in FIG. 5C. Conversely, for the configuration shown FIG. 5B the pixels of the single chip are shared by the two channels thereby reducing the resolution by half as half of the pixels are used for each of the left and right channels.

Example Camera/Sensor Designs

As discussed above with reference to FIGS. 5A and 5B, a single sensor may be employed to obtain left and right images of a stereo camera pair. The sensor may be partitioned into areas to receive light from left and right imaging optics that produces left and right images on the active area of the sensor. A mask can be employed to partition the active area of the sensor into these left and right areas for receiving the left and right images. In some embodiments, stereo optics with left and right lens trains image onto the single sensor that is coupled to a processor configured to collect left and right images from the sensor at far left and right edges of sensor and superimpose those images to form a stereo image with same convergence as eye. The mask can be moved to collect light from different parts of the sensor. In some embodiments, the mask can be moved dynamically to accommodate variable optical parameters of the camera optics, for example, variable focus and working distance, which coincides with varying divergence. The mask may be implemented via software and corresponds to which pixels of the sensor to exclude from image formation. Conversely, the software implemented mask determines what pixels are used to collect image data. Separate left and right open portions of the mask where light to form the image is collected can be spaced farther apart or closer together depending on the desired convergence angle, focus, work distance, etc.

In other designs, it may be possible to have a chip with two spaced apart active regions thereon corresponding to left and right image channels. A single chip in a single package can comprise semiconductor and be patterned such that two spaced apart regions of pixels may be created to receive light from left and right lens trains. The space may include in some embodiments electronics or dead space. The space between these regions may not be active areas for collecting and sensing light. The spacing may accommodate for example the space needed for the two (left and right) lens trains or other physical components. A single 45° turning prism or a pair of 45° turning prisms may be employed to redirect light from said lens trains onto the front face and active regions of the sensor.

Methods of Surgery

A surgeon makes an incision for access into the body and introduces tools initially into the body. As the tools progress into the surgical site, the surgeon may use certain embodiments of the cameras as disclosed herein on a retractor. In certain cases, the surgeon will use the proximal retractor cameras initially and the distal retractor cameras thereafter as the surgical tool(s) passes deeper into the surgical site, for example, passing through proximal regions of the opening in the body into more distal regions into the surgical site. The various cameras can be employed to guide advancement of the tool into the desired depth in the body and into the surgical site. Similarly, with removal of the instruments, this process may be reversed (for example, the distal camera may be used more after relying on the proximal camera).

Various embodiments of the system may additionally be configured to provide for the same convergence angle for each of the stereo cameras, for example, the stereo cameras on the retractor, including possibly both proximal and distal stereo cameras. Also, if a stereo camera is mounted on a surgical tool, such as for example, a Kerrison, this tool camera too may have the same convergence angle. Having a similar convergence angle from one stereo camera to another should provide a more comfortable viewing experience for the surgeon.

The convergence angle is determined by the separation of the left and right cameras of a stereo camera pair that make up the stereo camera. As discussed herein, these cameras obtain images of the object from different perspectives akin to the human's eyes separated by an interpupillary distance. The convergence angle is also determined by the distance to the object, for example, the working distance of the camera. In particular, the convergence angle depends on the ratio of the distance separating the left and right cameras and the working distance of the camera pair to the object.

The human brain and eye react to depth cues resulting at least in part from the convergence. Likewise images produced by stereo cameras having a convergence angle (based on interpupilary distance and working distance of the stereo camera pair), will provide depth cues to viewers of those images. As the surgeon may be transitioning between viewing images from the proximal and distal cameras on the retractor, and one or more cameras on surgical tools, the surgeon will receive depth cues from these different cameras. In various embodiments, the stereo cameras have the same convergence so as to avoid introducing changes among the depth cues as the surgeon moves from viewing video from one of the cameras to another and to yet another and back, for example.

In certain embodiments, stereo cameras may be configured to be adjusted to provide the same convergence angle. For example, the stereo camera or cameras on the retractor and/or surgical tool may be adjustable to provide the same convergence. As referred to above, these cameras may include proximal and/or distal cameras on the retractor.

As discussed above with reference to FIGS. 5A and 5B, a mask associated with the two-dimensional detector array may be adjusted to provide for the desired convergence angle. For example, a single sensor such as shown in FIGS. 5A and 5B may be employed to obtain left and right images of a stereo camera pair. The sensor may be partitioned into areas to receive light from left and right imaging optics that produces left and right images on the active area of the sensor. A mask can be employed to partition the active area of the sensor into these left and right areas for receiving the left and right images. In some embodiments, stereo optics with left and right lens trains image onto the single sensor that is coupled to a processor configured to collect left and right images from the sensor at far left and right edges of sensor. Using left and right displays, the left and right images are provided to left and right eyes of the surgeon or assistant, whose brain forms a third stereo image therefrom. The separation of the left and right areas that receive the left and right images establishes the interpupilary distant that together with the working distance controls the convergence angle. Accordingly, the mask can be moved to collect light from different parts of the sensor potentially increasing or decreasing this interpupillary distance. Moreover, in some embodiments, the mask can be moved dynamically (increasing or decreasing this separation) to accommodate variable optical parameters of the camera optics, for example, convergence, as well as variable focus and working distance. The mask may be implemented via software and corresponds to which pixels of the sensor to exclude from image formation. Conversely, the software implemented mask determines what pixels are used to collect image data. Accordingly, separate left and right open portions of the mask where light to form the image is collected can be spaced farther apart or closer together depending on the desired convergence angle.

Such a mask need not be limited to embodiments such as those disclosed in FIGS. 5A and 5B. Embodiments such as show in FIG. 5C, which employ two detector array chips, can also have one or more masks that can be moved to accommodate for different optical parameters including convergence, work distance, focal length, etc. One or both two dimensional detector arrays can have masks having open regions that are laterally translated to change the distance separating the locations where light is collected, thus changing, for example, the convergence angle. As discussed above, the mask may be implemented via software and corresponds to which pixels of the sensor to exclude from image formation. Conversely, the software implemented mask determines what pixels are used to collect image data. Separate left and right open portions of the mask where light to form the image on separate respective chips is collected can be spaced farther apart or closer together depending on the desired convergence angle. In some embodiments, a mask is disposed on one chip while the other chip does not have such a dynamically moveable mask. By moving the mask on the one chip, however, optical parameters such as convergence can be altered. For example, if the chip on the left has a dynamic mask, the open portions in the mask can be spaced farther apart or closer to the chip on the right depending on the desired convergence angle.

Accordingly, the mask can be adjusted, for example, one or more openings therein can be translated, to provide for the same convergence between stereo cameras on the retractor and/or surgical tool. For example, a mask on one or more stereo cameras (e.g., a stereo camera pair on a surgical tool, proximal and/or distal stereo cameras on a retractor, etc.) may be changed or reconfigured, for example, by moving one or more openings therein, to provide the same convergence angle. Consequently, using the reconfigurable mask with movable aperture(s), stereo camera pairs on retractors or surgical tools may be provided with a similar convergence. By maintaining the same convergence for the different cameras, the depth cues provided the surgeon can be maintain relatively constant despite viewing images from different stereo cameras (e.g., proximal retractor camera, distal retractor camera, surgical tool camera, etc.). As a result, a more comfortable viewing experience may be provided.

In certain embodiments, the stereo camera may additionally provide adjustable focus. One or more actuators may be included that are configured to translate one or more lenses in the camera optics that images the surgical site onto the two-dimensional detector array to change the focus of the camera. These actuators may be driven electrically in some embodiments although different types of actuators could be employed. These actuators can be included in the package that supports the camera and is disposed on the retractor. Advantageously, cameras on retractors (in contrast for example to endoscopes) have available space lateral to the imaging lenses (e.g., in the radial direction) in which such actuation devices can be located. The result may be that the lateral dimensions (e.g., in x and y) exceed the longitudinal dimensions (z), however, surgical access to the surgical site would not be impeded by utilization of the space surrounding the lenses in the lateral or radial directions.

In various embodiments, when the focus is changed using the actuator, the mask may be reconfigured or changed as discussed above. For example, one or more open region or aperture in the mask through which light is directed to the left and/or right channel can be shifted laterally to increase or decrease the convergence angle. In this manner, the convergence angle of the stereo camera with the adjustable focus disposed on the retractor or surgical tool can be altered to be the same. Constant convergence angle for different stereo cameras can be provided even if such cameras include an adjustable focus. Both the focus and the mask can be changed as needed to provide the desired focus and convergence angle.

Incorporating an adjustable focus enables a camera lens having a smaller depth of focus to be employed. Such a camera lens will have a larger numerical aperture and smaller F-number than a similar lens that produces a larger depth of focus. Some benefits of the larger aperture lens are increased light collection and resolution.

Adjustment of Camera Focal Len the and/or Orientation

In various embodiments, the cameras on the retractor provide focused images of a surgical tool tip. Furthermore, various embodiments include software that maintains focus on the surgical tool tip, even while the tool moves about the surgical site. In particular, when the tool moves in any direction (e.g., laterally, vertically, or a combination of both), the software can be configured to maintain the retractor cameras' focus (or other camera's focus) on the tool tip by changing a focal length and/or orientation of the cameras. In various embodiments, the position and/or movement of the tool tip can be determined through a tracking device on the surgical tool, e.g., on or at the tool tip.

When the tool tip moves about the surgical site, the distance between the cameras imaging the surgical tool tip and surgical tool tip changes, according to some embodiments. Furthermore, the distance between one camera and the tool tip, and the distance between another camera and the tool tip, can be different. For example, when the instrument tip moves about the surgical site laterally, it can move closer to one camera and farther away from another camera. As the tool tip moves the movement can cause the tool tip to become out of focus. In some embodiments, a foot pedal can be actuated (e.g., a foot pedal can be depressed), to enable adjustment of the focal distance and/or orientation of the cameras and thereby maintain focus of the target image. For example, actuation of a foot pedal can cause the retractor cameras to maintain focus on the surgical tool tip. Further, in order to account for the varying distances between each of the cameras and the tool tip, while maintaining focus of the tool tip, various embodiments can include software that changes the focus of the cameras as the tool tip changes position.

In addition, in the case where the cameras include electrically controlled transducers or actuators to vary their orientation, the software can be configured to change the orientation of the cameras (e.g., tip, tilt, etc.) using the actuators, as the tool tip moves vertically into or out of the surgical site. For example, if the tool tip moves deeper into the surgical site, the software can be configured to increase the angle of the cameras in a downstream direction (e.g., deeper into the surgical site). As another example, if the tool tip moves out of the surgical site, the software can be configured to increase the angle of the cameras in an upstream direction. In various embodiments, the software can be configured to change the orientation of the camera with movement of the surgical tool tip, such that the cameras' view follows movement of the tool tip. This software may for example cause a processor to drive the actuators that are configured to move the cameras.

In some embodiments, one or more cameras on the surgical tool can similarly be configured to have focal adjustment and orientation adjustment in order to maintain focus of the surgical site. In addition, tracking information can be received via a tracking device on the surgical tool. Based on this tracking information, when the surgical tool moves, the software can reposition the focal length and/or orientation of the tool camera(s) in order to maintain focus on the surgical site. Thus, the cameras can maintain focus on the surgical site while the surgical tool changes positions.

The images of the surgical tool and/or the surgical site can be displayed on a surgical visualization system display such as one or more surgeons display and/or assistants displays according to some embodiments. Those images can also be displayed on a graphical user interface according to some embodiments. In some embodiments, a graphical user interface is displayed on the surgical visualization display. In other embodiments, a separate display is provided for the graphical user interface. In either case, the images of the surgical tool and/or the surgical site can be displayed on the surgical visualization system display(s) as well as a graphical user interface(s). In some embodiments, the movement of the tool or tool location is used to control selection of the camera images that are displayed on the displays. Additionally, actuation of a foot pedal can cause the surgical tool cameras to maintain focus on the surgical site. In some embodiments, actuation of one foot pedal device can cause both the retractor cameras and the surgical tool cameras to maintain focus of their target.

Fluorescence Imaging

In various embodiments, images or information in addition to video from the cameras on the retractor can be presented via the display. For example, in some embodiments fluorescence information can be displayed. Cameras that image in different wavelengths, such as infrared, could image the surgical site or objects contained therein. In some embodiments, features could be made to fluoresce, for example, by injecting fluorescent chemical and illuminating the area with light the will induce fluorescence. Such a technique may be useful to identify and/or highlight the location and/or boundaries of specific features of interest such as tumors, etc. The fluorescence or other wavelength of interest may be detected by the cameras on the retractor or one or more other cameras. In some embodiments, images produced by fluorescence or other wavelengths of interest are superimposed on one or more images from cameras on the retractor or other camera(s). Filtering could be provided to remove unwanted wavelengths and possibly increase contrast. The filter can remove excitation illumination. In some embodiments emission image content, (e.g., fluorescing tissue) can be parsed and superimposed on image content that is not emitting (e.g., tissue that is not fluorescing), or vice versa. In various embodiments, such as where the fluorescing wavelength is not visible (e.g., for fluorescence in the infrared), an artificial color rendition of the fluorescing content can be used in place of the actual fluorescing color so as to enable the fluorescing tissue to be visible.

Kerrison

In various embodiments, the console can be equipped with a hydraulic and/or pneumatic system that can be employed to drive hydraulic and pneumatic tools.

Figure 9A:
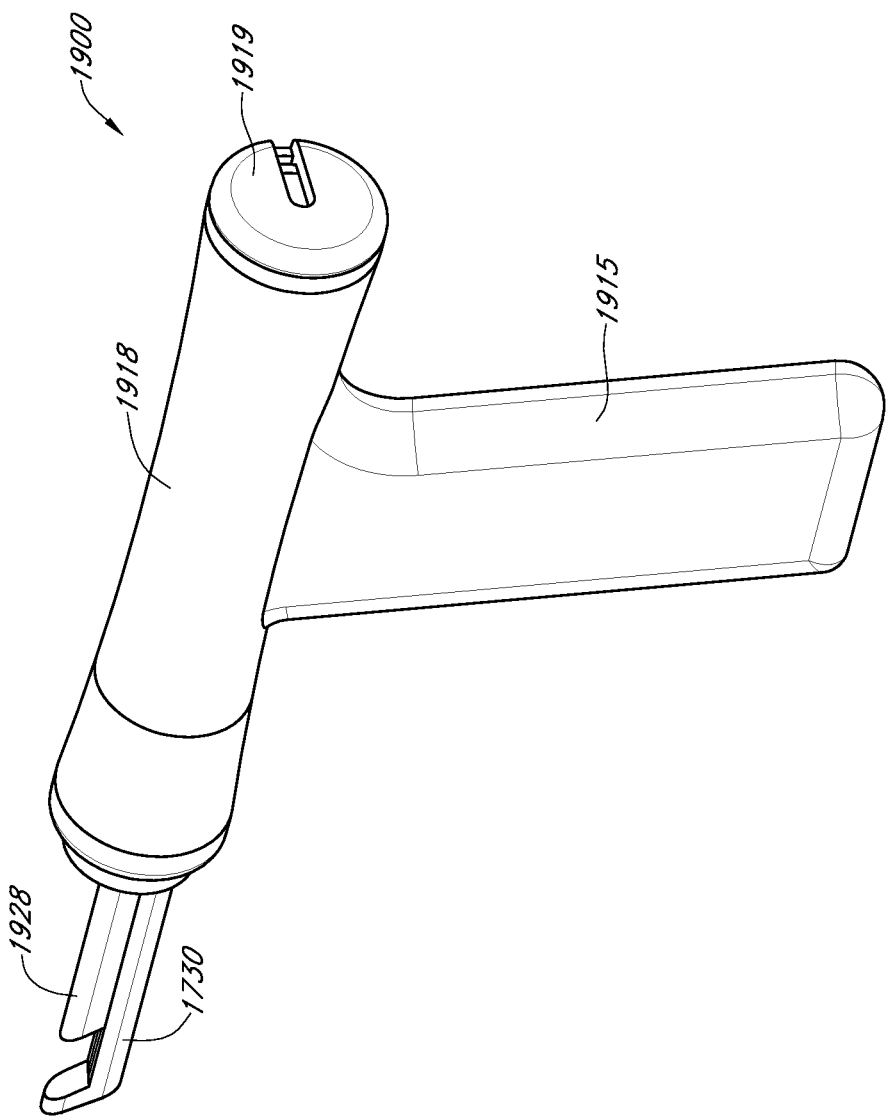
FIGS. 9A-9C are schematic illustrations of an embodiment of a pneumatically actuated tool.
Figure 9B:
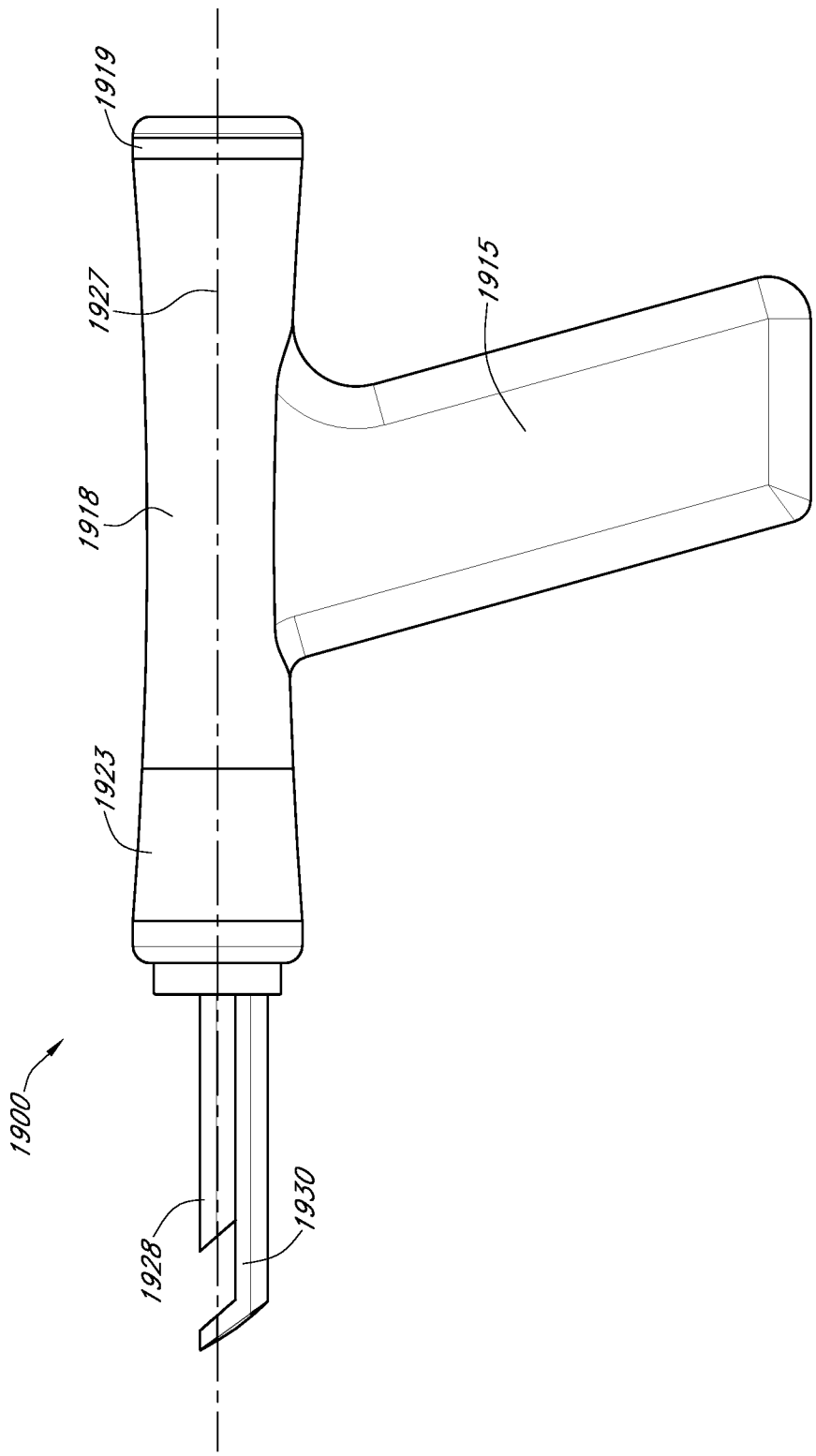
Figure 9C:
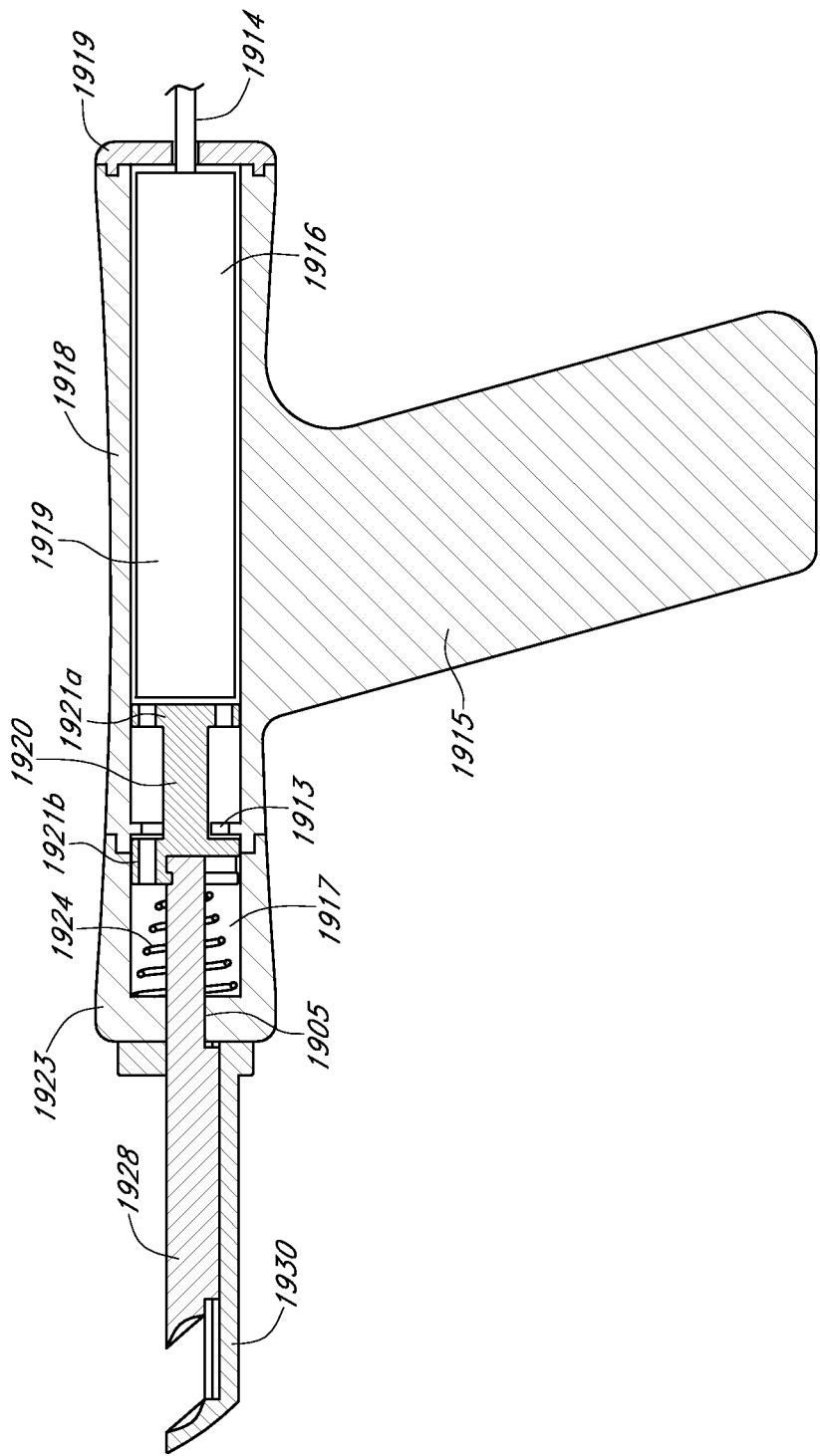

FIGS. 9A-C illustrate an embodiment of a Kerrison 1900 that can be operated hydraulically. The Kerrison 1900 can include a proximal handle portion 1918. The proximal handle portion 1918 can be attached or otherwise connected with a distal handle portion 1923. In some embodiments, the proximal handle portion 1918 includes a grip 1915 (e.g., a pistol grip or other ergonomic grip). The proximal handle portion 1918 can be configured to rotate about a handle axis 1927 (shown, e.g., in FIG. 9B9B) with respect to the distal handle portion 1923.

In some embodiments, the Kerrison 1900 includes a base 1930. The base 1930 can include a cutting portion at a distal end (e.g., the left end of FIG. 9B9B). The base 1930 can be fixed axially (e.g., parallel to the handle axis 1927) with respect to the distal handle portion 1923 and/or with respect to the proximal handle portion 1918. In some embodiments, the base 1930 and/or distal handle portion 1923 are rotatable about the handle axis 1927 with respect to the proximal handle portion 1918.

As shown in FIG. 9C, the proximal handle portion 1918 can define an actuation chamber 1919. In some embodiments, at least a portion of the actuation chamber 1919 along a length of the actuation chamber 1919 parallel to the handle axis 1927 has a substantially constant cross-section. In some embodiments, at least a portion of the actuation chamber 1919 has a circular cross-section.

In some embodiments, the distal handle portion 1923 defines a distal actuation chamber 1917. In some embodiments, the distal actuation chamber 1917 has a cross-section with substantially the same shape and/or size as a cross-section of at least a portion of the actuation chamber 1919.

The Kerrison 1900 can include a piston 1920. The piston 1920 can be operably coupled with and/or attached to a Kerrison top portion 1928. For example, the piston 1920 can be a unitary part with or attached/adhered/welded to the Kerrison top portion 1928. In some embodiments, the piston 1920 and top portion 1928 are connected via a releasable connection (e.g., a protrusion-slot connection). The piston 1920 can be fixed axially (e.g., parallel to the handle axis 1927) with respect to the top portion 1928. In some embodiments, the piston 1920 is fixed rotationally with respect to the top portion 1928 (e.g., rotation about the handle axis 1927).

The top portion 1928 can include a cutting edge on the distal end of the top portion 1928. The cutting edge of the top portion 1928 can be configured to operate with the cutting portion of the base 1930 to cut medical material (e.g., bone and/or other tissue). In some embodiments, the top portion 1928 is connected to the base 1930 via a track-protrusion engagement. For example, the top portion 1928 can include a protrusion configured to slidably engage with a track in the base 1930. Engagement between the track of the base 1930 and the protrusion of the top portion 1928 can limit the movement of the top portion 1928 with respect to the base 1930 to the axial direction (e.g., parallel to the handle axis 1927).

In some embodiments, the piston 1920 is configured to fit within the actuation chamber 1919 and/or within the distal actuation chamber 1917. For example, the piston 1920 can have a first guide portion 1921a configured to fit snugly within the actuation chamber 1919 (e.g., fit such that movement of the first guide portion 1921a within the actuation chamber is substantially limited to axial movement and rotational movement about the handle axis 1927). In some embodiments, the piston 1920 includes a second guide portion 1921b. The second guide portion 1921b can be configured to fit snugly within the distal actuation chamber 1917. Axial movement of the piston 1920 can be limited by interaction between a radially-inward projection 1913 of the proximal handle portion 1918. For example, proximal axial movement of the piston 1920 can be limited by interaction between the second guide portion 1921b and the radially-inward projection 1913. In some embodiments, distal axial movement of the piston 1920 is limited by interaction between the first guide portion 1921a and the radially-inward projection 1913.

The distal handle portion 1923 can include a distal opening 1905. The distal opening 1905 can be sized and/or shaped to accommodate passage of the top portion 1928 therethrough. In some embodiments, the top portion 1928 is sized and shaped to fit snugly within the distal opening 1905. For example, the top portion 1928 can have a non-circular cross-section sized to substantially match a cross-section shape of the distal opening 1905. In some embodiments, the top portion 1928 is rotationally locked to the distal handle portion 1923 via interaction between the distal opening 1905 and the top portion 1928. In some such embodiments, the grip 1915 can be rotated relative to the top portion 1928 and the base 1930. In some embodiments, sensors and/or optical devices (e.g., cameras, CMOS sensors, etc.) can be attached to the proximal handle portion 1918 such that the relative alignment of the sensors and/or optical devices with respect to the handle portion 1918 remains consistent independent of rotation of the top portion 1928 and base 1930 with respect to the handle portion 1918.

As illustrated in FIG. 9C, an actuation element 1916 can be positioned within the actuation chamber 1919. In some embodiments, the actuation element 1916 is an inflatable and/or disposable bag or balloon configured to be inflated/deflated with physiological saline. In some embodiments, the actuation element 1916 is a bellows (e.g., stainless steel metal bellows such as those manufactured by BellowsTech, Inc.). The actuation element 1916 can be configured to exert an axial force on the piston 1920 (e.g., a force upon the first guide portion 1921a) to move the piston 1920 in the distal axial direction. The Kerrison 1900 can include a biasing structure 1924 (e.g., a spring or other resilient structure) configured to bias the piston 1920 in the proximal axial direction. For example, the biasing structure 1924 can provide a return force to return the piston 1920 to push the piston 1920 in the proximal axial direction when the axial force from the actuation element 1916 is reduced and/or removed.

In some embodiments, the Kerrison 1900 includes a return valve (not shown) configured to introduce physiological saline so as to provide compression to the actuation element 1916. The return valve may, for example, allow injection of pressurized gas into the distal actuation chamber 1917 or in the region of the proximal actuation chamber 1919 forward the first guide portion 1921a. The fluid introduced via the return valve can be used to move the piston 1920 in the proximal direction. In some such embodiments, the Kerrison 1900 does not include a biasing structure 1924.

The actuation element 1916 can be fluidly connected to a conduit 1914 through which physiological saline can be input into and pulled out from the actuation element 1916. In some embodiments, hydraulic controls associated with the actuation element 1916 are operated via a foot pedal. Such embodiments can allow for greater dexterity for the user of the Kerrison 1900 by reducing the operating variables controlled by the Kerrison 1900 handle portions 1918, 1923. Elastomeric and/or proportional valves can be used to enhance the responsiveness of the Kerrison 1900 to operation of the foot pedal (see, e.g., FIGS. 43E-43F).

Additionally, with reference to FIGS. 9D-9G, the Kerrison can have a variety of cutting head configurations. For example, with reference to FIGS. 9E-9G, in any of the embodiments disclosed herein, the cutting head 1728 can have a circular shaped cross-section (as in FIG. 9E), the cutting head 1728 can have a C shaped cross-section (as in FIG. 9F) or a closed D shaped cross-section (as in FIG. 9G). Other shapes and designs are possible.

Figure 9D:
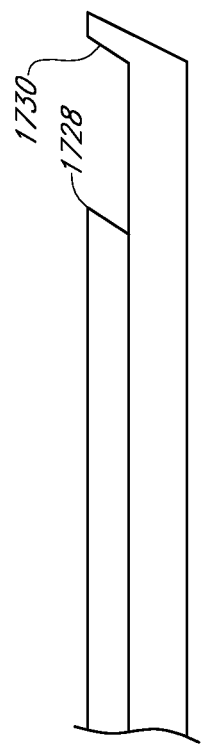
FIG. 9D is a schematic illustration of another embodiment of a hydraulically actuated surgical device.
Figure 9G:
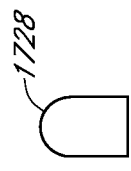
FIG. 9G is a schematic illustration of another embodiment of a cutting tip of the surgical device embodiment of FIG. 9D.
Figure 9F:
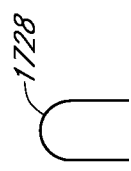
FIG. 9F is a schematic illustration of another embodiment of a cutting tip of the surgical device embodiment of FIG. 9D.
Figure 9E:
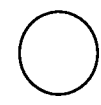
FIG. 9E is a schematic illustration of an embodiment of a cutting tip of the surgical device embodiment of FIG. 9D.

Additionally, in any of the Kerrison embodiments described herein, the fixed cutting surface 1730 can be generally vertically oriented. As shown in FIG. 9D, the fixed cutting surface 1730 can also be angulated (for example, angled at approximately 45 degrees, or from approximately 35 degrees or less to 55 degrees or more).

In the tool embodiments disclosed herein, including without limitation the Kerrison, the cutting surface or top surface of the tool can be bayonetted. The bayonetted structure of the tool can allow the tool to be inserted into the surgical area without interfering or obscuring the views of the surgical site or overhead views of the surgical field. The bayonet style tool can be utilized for the Kerrison, forceps, scissors, or other tools described herein. The bayonet configuration can be advantageous for small surgical sites or external viewing of the surgical site. The bayonet feature reduces the area obscured by the tool within the surgical site.

In any of the tool embodiments disclosed herein, including without limitation the Kerrison, the housing supporting or comprising the tool can be configured to have a port or lumen therein arranged to facilitate the removal of tissue and bone extracted from the surgical site. For example, the Kerrison can have a side port or opening located proximal of the cutting head 1728, though which cut tissue can be removed (e.g., pushed through port or opening as cutter withdraws and Kerrison returns to the default position). In some embodiments, a source of suction, or a source of saline and suction, can be supplied to the port. Additionally, the removal port or lumen of the housing can also support a mechanical removal mechanism, such as but not limited to a screw type auger (which can be hydraulically actuated, via for example a gear motor, gerotor, or vane motor 1512 discussed above), to facilitate removal of bone debris and extracted tissue from the surgical site. In some embodiments, the removed tissue can be extracted to a waste reservoir supported by or tethered to the housing of the tool. In another embodiment, the movable cutting head of the Kerrison can be a generally cylindrical tube that can be actuated (in the matter described above) to slidably move against the fixed cutting surface 1730. For example, said cylindrical tube can be slidable within an outer housing of the Kerrison when a force is exerted thereon via the expansion of the second inflatable element 1716, as discussed above.

Additionally, in any of the tool embodiments disclosed herein, including without limitation the Kerrison, the housing supporting or comprising the tool can be configured to have a suction port and a source of saline so that the tool and/or the surgical site can be flushed with saline and the saline and debris can removed via the suction line simultaneously or sequentially with the flushing. In some embodiments, the saline can be provided through the conduit used to provide saline to the second inflatable element, through the same or a different lumen of such conduit.

Additionally, the saline source or conduit and/or the suction source or conduit can be separate from the tool so that it can be independently positioned. In some embodiments, the saline source or conduit and/or the suction source or conduit can be tethered to the tool.

Any of the hydraulic system embodiments disclosed herein can be configured to incorporate or use any suitable surgical tools, including without limitation scissors, microscissors, forceps, micro-forceps, bipolar forceps, clip appliers including aneurysm clip appliers, rongeur, and, as described, Kerrison tools.

Turbine

Figure 10A:
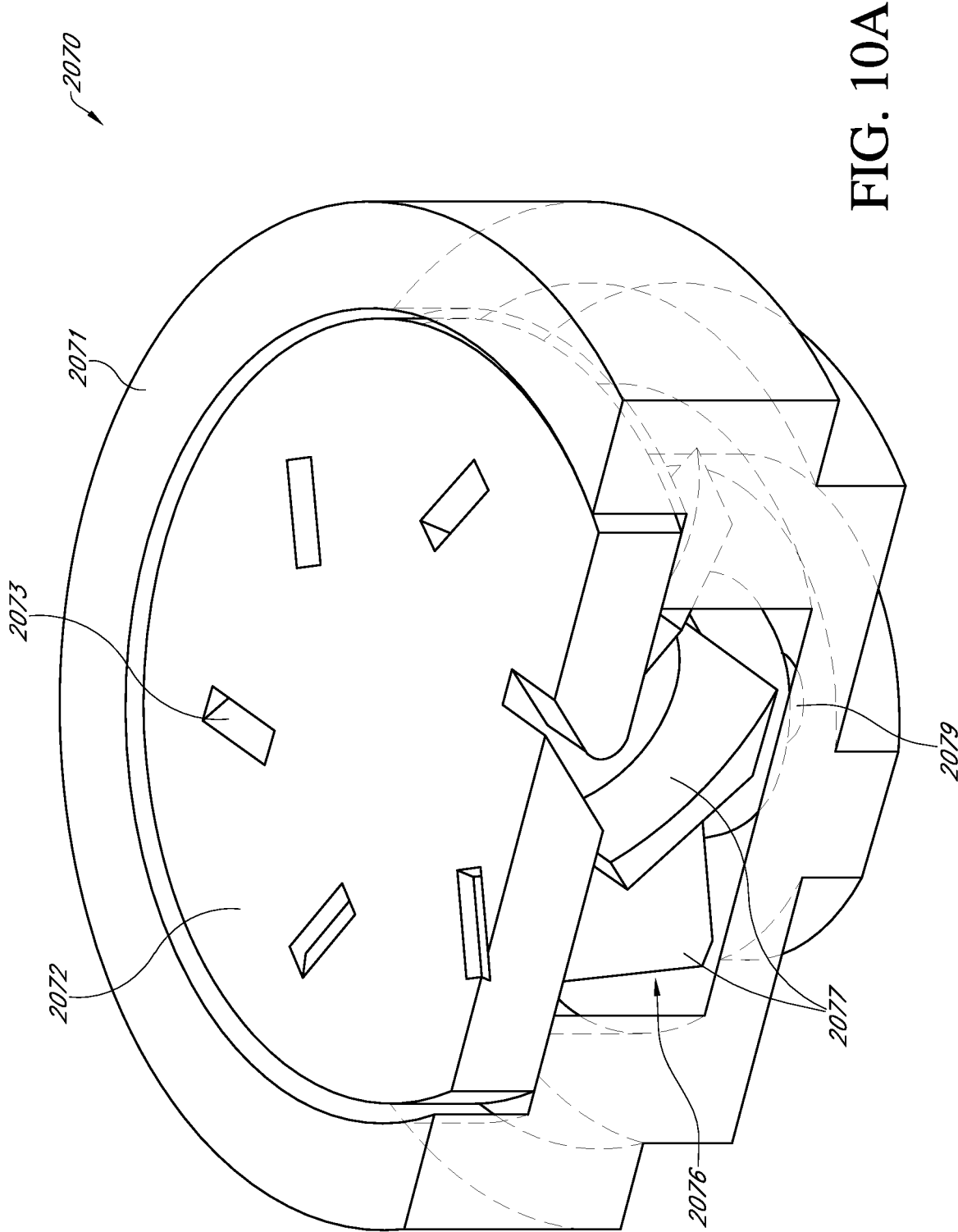
FIG. 10A shows a perspective cross-section of a hydraulic turbine.
Figure 10B:
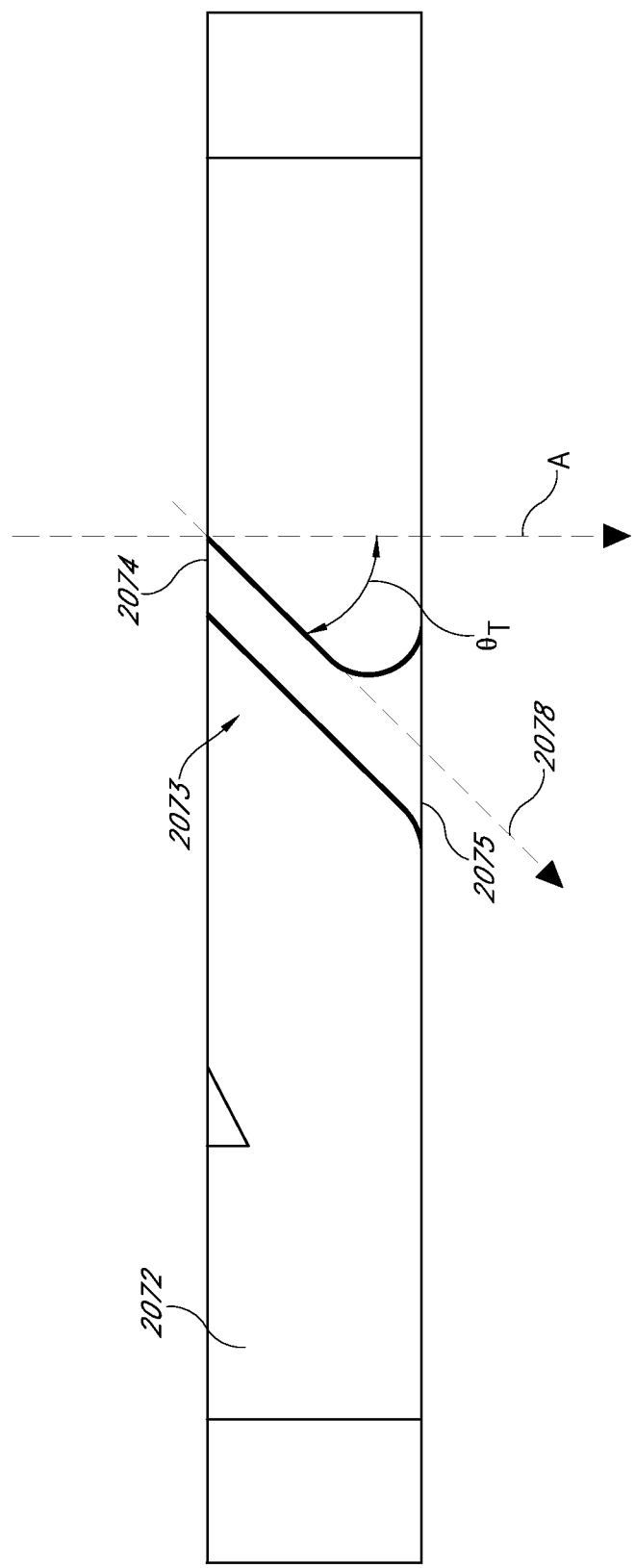
FIG. 10B shows a cross-section of a portion of the hydraulic turbine of FIG. 10A.

Another tool is a drill which can be driven by a hydraulic turbine. The tool can be driven by a hydraulic turbine. In some embodiments, as illustrated in FIGS. 10A and 10B, a hydraulic turbine 2070 includes a turbine housing 2071. In some cases, at least a portion of a nozzle frame 2072 is housed within the turbine housing 2071. In some embodiments, stator vanes can be used in conjunction with and/or in place of the nozzle frame 2072. The nozzle frame 2072 can include one or more turbine nozzles 2073. In some embodiments, the turbine nozzles 2073 are positioned in a circumferential array, as illustrated in FIG. 10A. Each of the turbine nozzles 2073 can have a nozzle inlet 2074 and a nozzle outlet 2075. In some embodiments, the nozzles 2073 have substantially constant cross-sectional areas from nozzle inlet 2074 to nozzle outlet 2075 (e.g., drill hole-type nozzles). For example, circular nozzles can be used.

The relative areas of the nozzle inlet 2074 and the nozzle outlet 2075 can vary. For example, the nozzle outlet 2075 can have an area that is greater than or equal to approximately 125% of the area of the nozzle inlet 2074 and/or less than or equal to about 600% of the area of the nozzle inlet 2074. In some embodiments, the area of the nozzle outlet 2075 is approximately 300% of the area of the nozzle inlet 2074.

As illustrated in FIG. 10B, the profile of the nozzle 2073 can widen between the nozzle inlet 2074 and the nozzle outlet 2075. The rate at which the turbine nozzle 2073 widens between the nozzle inlet 2074 and the nozzle outlet 2075 can vary. For example, the nozzle 2073 can flare out in the direction of the nozzle outlet 2075. In some embodiments, the profile of the nozzle 2073 narrows between the nozzle inlet 2074 and the nozzle outlet 2075. In some embodiments, the nozzles 2073 have substantially constant cross-sectional areas from nozzle inlet 2074 to nozzle outlet 2075 (e.g., drill hole-type nozzles). In some embodiments, the nozzle inlet 2074 can be tapered or flared in such that an opening into the nozzle inlets 2074 is wider or larger than a midsection of the nozzles 2073.

In some embodiments, physiological saline is directed through the nozzle frame 2072 toward an impeller 2076. The impeller 2076 can include a plurality of impeller blades 2077 around the outer periphery of the hub of the impeller 2076. The impeller blades 2077 can rotate within a blade cavity 2077a. (See FIG. 10C.) The impeller 2076 can be integral with or otherwise rotationally coupled with an output shaft 2079 for driving the tool 2082, which can be a drill or other rotational tool. The outer diameter of the hub of the impeller 2076 can be smaller than the outside diameter of the array of hydraulic nozzles 2073. For example, the outer diameter of the hub of the impeller 2076 can be greater than or equal to approximately 15% of the outer diameter of the hydraulic nozzles 2073 and/or less than or equal to approximately 75% of the outer diameter of the hydraulic nozzles 2073. In some cases, the outer diameter of the impeller 2076 can be greater than or equal to 0.5 inches and/or less than or equal to approximately 1.5 inches. Many variations sizes and relative sizes of the components of the hydraulic turbine 2070 and its subcomponents are possible.

In some cases, the impeller blades 2077 are oriented at an angle offset from the central axis of the impeller 2077. The hydraulic nozzles 2073 can be configured to turn the flow of physiological saline from an axial direction A to nozzle direction 2078 as the flow is passed through the nozzle frame 2072 toward the impeller 2076. The nozzle direction 2078 can be selected to be at an angle $\theta_T$ offset from axial A such that the nozzle direction 2078 is substantially perpendicular to the faces of the impeller blades 2077. The closer nozzle outlets are to the plane of the impeller blades 2077 and the more radially-directed the flow from the nozzles, the more torque can be imparted upon the impeller blades 2077. For example, the nozzle outlets can be positioned close to the impeller blades 2077 in the axial direction and can direct physiological saline at a highly-radial angle toward impeller blades 2077 whose surfaces are close to parallel to the rotation of axis of the impeller 2076.

In some cases, utilizing a plurality of circumferentially-distributed turbine nozzles 2073 to drive a plurality of impeller blades 2077 can increase the torque output of impeller 2076 as compared to a configuration wherein only one turbine nozzle 2073 is utilized. In some such configurations, the outer diameters of the nozzle frame 2072 and impeller 2076 can smaller than a single-nozzle configuration of equal output torque.

In some embodiments, the hydraulic turbine 2070 can be configured to operate at rotational speeds of 40,000 rpm to 60,000 rpm, though higher and lower rpm values may be possible. In some embodiments, the hydraulic turbine is configured to operate at rotational speeds of 100,000 rpm. The hydraulic turbine 2070 can be configured to operate at operating pressures between 70 psi and 190 psi, though greater and lesser operating pressures are possible. In some embodiments, the operating pressure of the hydraulic turbine 2070 is designed to be approximately 120 psi.

Figure 11:
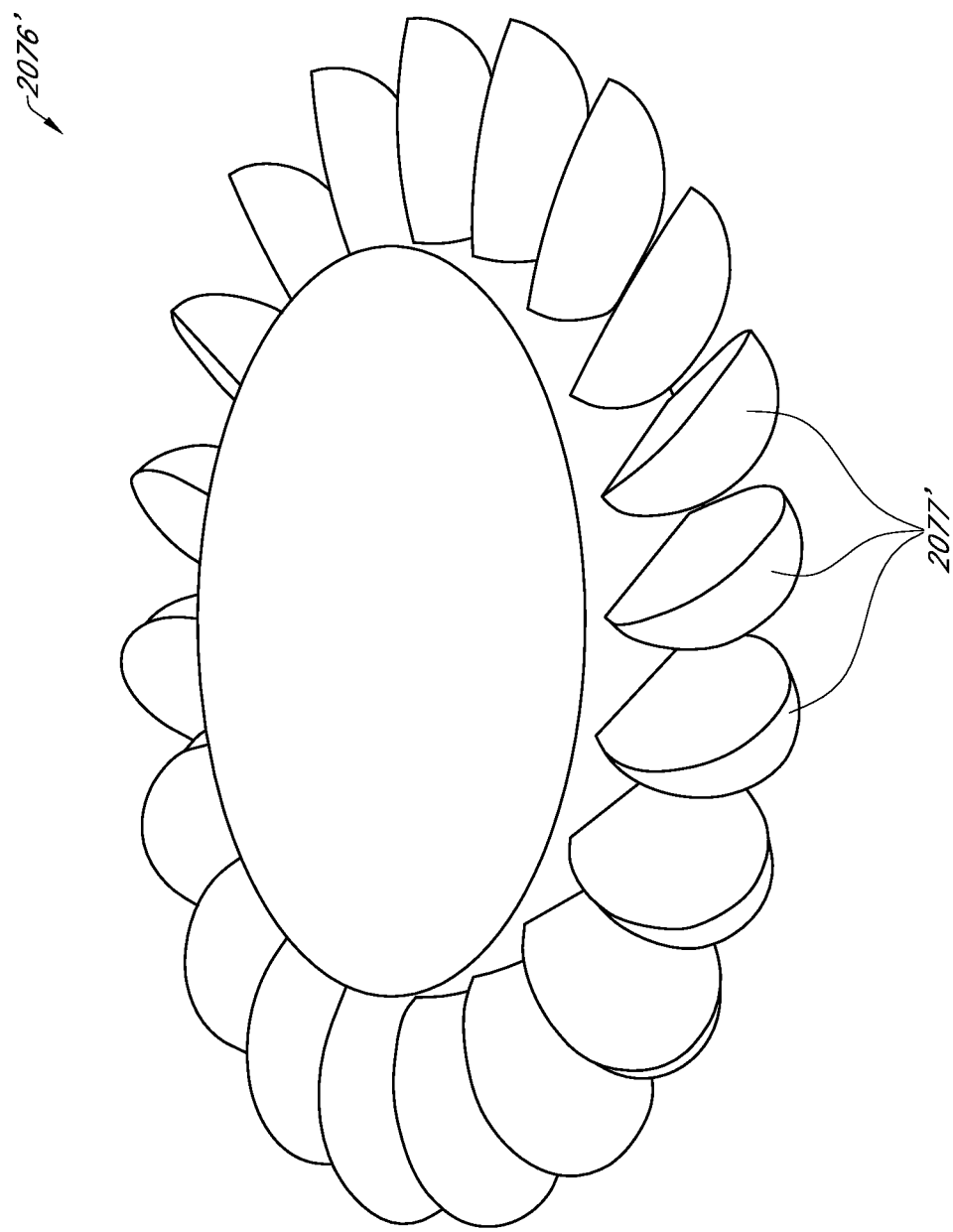
FIG. 11 shows one embodiment of an impeller.

As illustrated in FIG. 11, an impeller 2076' can be designed to have bucket-shaped impeller blades 2076'. The bucket-shaped impeller blades 2077' can be oriented at an angle of approximately 45° from the axial direction A. Many variations of the impeller blade 2077' angles are possible. Additionally, many different shapes of blades 2077 are possible, such as Pelton or Turgo shaped blades.

Figure 10C:
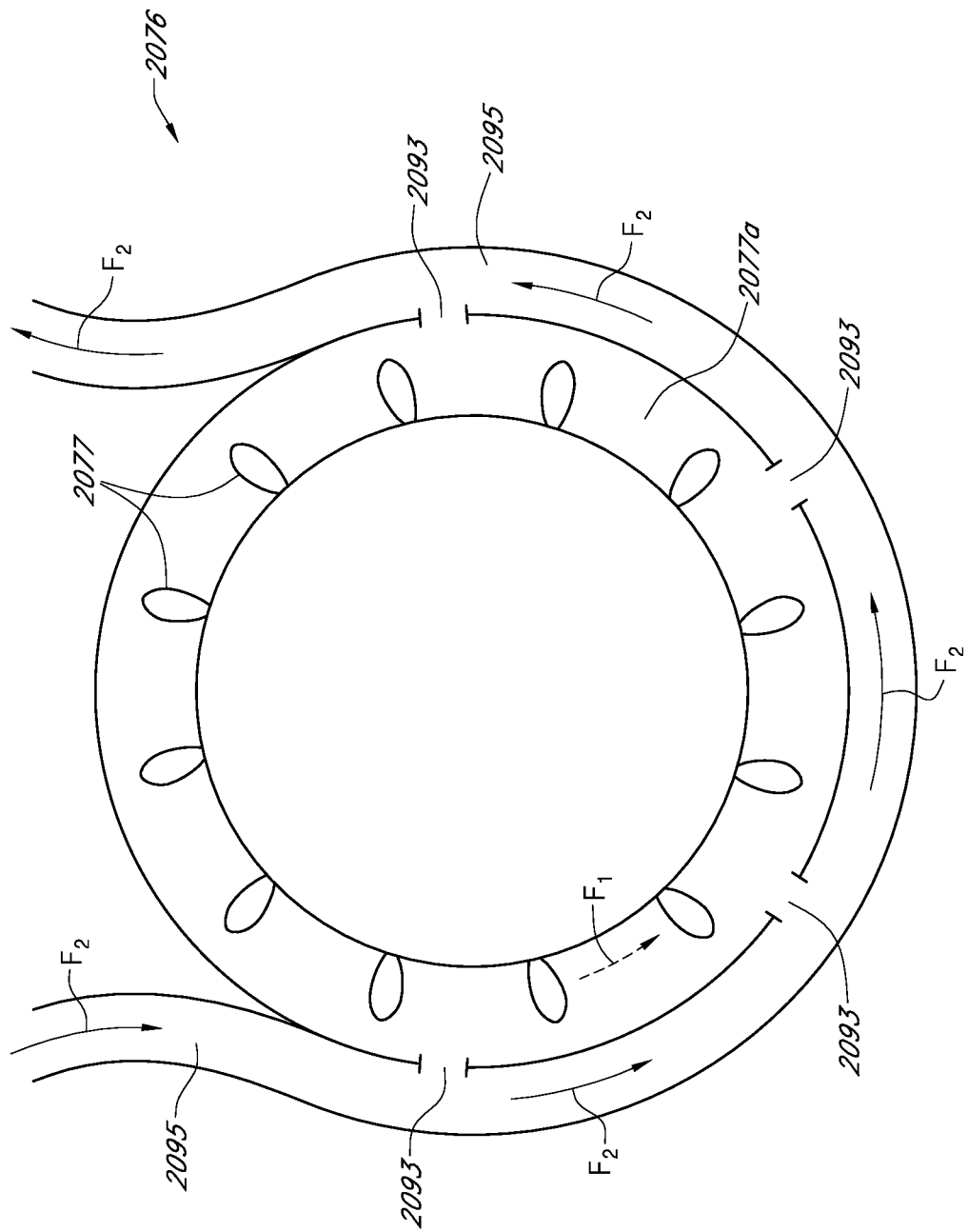
FIG. 10C shows a cross-section of a portion of the hydraulic turbine of FIG. 10A and a diverted fluid flow path.

As illustrated in FIG. 10C, the hydraulic turbine 2070 can be designed to collect the physiological saline that has already impacted the impeller blades 2077, 2077' (hereinafter 2077 for simplicity). For example, an exhaust angle can be calculated to represent the angle at which physiological saline reflects off of the impeller blades 2077 after impact with the impeller blades 2077. One or more vacuum ports 2093 can be positioned on or in the turbine housing 2071 to extract the fluid F1 that is reflected off of the impeller blades 2077 and redirect the fluid F1 into a bypass channel 2095. In some embodiments, the vacuum source can be an external pump (e.g., a peristaltic pump) or the vacuum can be the result of a Venturi effect created by the diversion of fluid. For example, in some embodiments, the vacuum source can be provided by diverted, high velocity fluid F2 directed to bypass the impeller 2076. In some embodiments, one or more ports 2093 in the hydraulic turbine housing 2071 (e.g., on the side of the housing closer to the impeller 2076 than to the nozzle frame 2072) can create fluid communication between the reflected fluid F1 in the blade cavity 2077A and the diverted high velocity fluid F2 in the bypass channel 2095. The pressure differential between the two fluid bodies (e.g., lower pressure in fluid F2 and higher pressure in fluid F1) will pull the reflected fluid F1 out of the housing 2071 and into the diverted fluid path 2095. Removal of the reflected fluid from the housing 2071 can increase the performance of the turbine 2070 by reducing the viscous drag on the impeller from undiverted fluid F1. For example, the viscous frictional losses that would be otherwise incurred from interaction between the reflected fluid F1 and the impeller 2076 and/or output shaft 2079 can be reduced. The diverted high velocity fluid F2 and scavenged reflected fluid F1 can be diverted back to the cassette 2020 for re-pressurization. In some embodiments, scavenging reflected fluid F1 and diverting it back to the cassette 2020 can reduce the amount of physiological saline required to operate the tools and/or other components of the system. In some embodiments, the housing 2071 can include one or more ports open to ambient. Such ports can be configured to receive pressurized air or other pneumatic gas. In some embodiments, the turbine 2070 is configured to operate as a dual hydro/pneumatic turbine configured to operate via hydraulic power and pneumatic power or a continual variance of hydraulic and pneumatic power. A controller or switch(s) can be used to vary the amount of hydraulic fluid or pneumatic air or gas are applied to the turbine. In some embodiments, the controller or switch(es) allow the user to increase pneumatic gas or air and decrease hydraulic or vice versa. The pneumatic gas or air and hydraulic fluid can be provided by output ports on the display console. Likewise, the controller and/or switch(es) may be on the controller or remotely located.

In some embodiments, multiple impellers 2076 (e.g., multiple turbine wheels) can be utilized in the same turbine housing 2071. In some such embodiments, the overall diameter of the turbine 2070 and/or some of its components can be reduced relative to a single-impeller turbine 2070 without sacrificing output torque.

Some instruments such as surgical tools use torque or mechanical force to translate manual input into tool actuation. For example, a Kerrison for bone removal generally includes a handle mechanically coupled to a head including a stationary portion and a movable portion. When a user squeezes the handle, the movable portion moves closer to the stationary portion in a cutting manner (e.g., in a shearing manner), for example to remove bone by trapping the removed bone between the stationary portion and the movable portion (e.g., within a channel between the stationary portion and the movable portion). Other examples of tools include an aneurysm clipper, a rongeur, forceps, scissors, and the like, although many other hand-operated tools are known to those skilled in the art. Referring again to the Kerrison, the pace and force of the squeezing translates to the pace and force of the cutting, and this phenomenon is also applicable to other hand-operated tools. This translation can be disadvantageous, for example varying based on each user, being too slow or too fast or having variable speed, lacking force or imparting too much force or having variable force, etc. Additionally, periodic use of such manually operated tools (e.g., during a lengthy operation or procedure) can lead to hand fatigue of the surgeon or user. Manual actuation leads to inadvertent movement of the tool tip.

The hydraulic system may also be used for other purpose such as cleaning optics and/or cooling light emitters for illuminating a surgical site.

Pops-Off Valve for Camera Cleaning/Cleaning Based on Detection of Blood

In some embodiments, a fluid reservoir can be fluidly connected to one or more fluid outlets (e.g., nozzles) configured to wash optical components (e.g., cameras, LEDs, and/or other components disposed in the surgical site that can be dirtied by blood, bodily fluids, or debris). The fluid reservoir can be fluidly connected to the fluid outlets via a hydraulic manifold in console. In some embodiments, one or more valves (e.g., proportional, elastomeric, and/or on/off valves) can be positioned in the fluid path between the fluid reservoir and the fluid outlets.

For example, a pulsing valve (e.g., a pop off valve) can be positioned in a fluid path between the fluid outlets and the fluid reservoir. In some embodiments, the pulsing valve is disposable. The pulsing valve is configured to open when a pressure threshold is reached. In various embodiments, the valve closes once the pressure returns to below the threshold. In some embodiments, the operation of the pulsing valve can produce a substantially square wave fluid pulse. The pulsing valve can be used to provide short duration liquid pulses to wash optics such as the camera optics. One benefit of such a pulse is the reduction of image distortion that would result in interruption of usable video stream provided to the surgeon. Such degradation of the video can be caused by flowing liquid across the camera for a noticeable period of time during which the image is distorted. In various embodiments, the pulsing or pop off valve can be located so as to wash all the cameras at the same time. The pulsing valve, for example, can be located upstream to where the line splits into different fluid outlets to clean different cameras.

To activate the pulsing valve, the pressure may be increased beyond the threshold for opening the pulsing valve. The pulsing valve may, for example, be connected to a high pressure source of fluid via a valve. The valve can be opened sufficiently to provide increased pressure beyond the threshold value resulting in a pulse of liquid from the pulsing valve. In certain embodiments the liquid pulses are produced periodically. For example, a processor may cause the valve to be opened periodically based on a schedule programmed into the processor or selected by the user via the processor. In some embodiments, liquid pulses are produced when blood or other obstruction is detected. The intensity level of the camera can be monitored to determine when visibility is compromised. In various cases, the color of the light reaching the camera can be analyzed to determine, for example, that blood is obstructing or impairing vision of the cameras and to thereby trigger pulse washing. The processor could be utilized to analyze the image signal and determine whether pulse washing is to be initiated. In some embodiments, attenuation of the red wavelength in comparison to other wavelengths such as green may indicate that blood is on the camera and reducing the amount of light entering the camera.

A three-way valve can also be employed. The three-way valve can operate to permit fluid from the fluid reservoir or gas such as pressurized gas from a pump to access the fluid outlets via the pulsing valve. The three-way valve can be configured to selectively shut off supply of fluid from the fluid reservoir and provide instead gas (e.g., pressurized gas from a pump). In some embodiments, shut off of fluid from the fluid reservoir to the fluid outlets can reduce the likelihood of "dribbling" or other inadvertent leakage of liquid from the fluid outlets onto the optical components. The pressurized air stream used to dry the camera optics can carry away any residual liquid that would otherwise dribble onto the camera at a later time. Depending on the design, the three-way valve can be positioned upstream or downstream of the pulsing valve. In some embodiments, positioning the three-way valve downstream of the pop off valve may further reduce dribbling.

In some embodiments, gas can be directed to the fluid outlets. For example, the pneumatic assembly can be configured to direct pressurized pneumatic gas (e.g., air) to the fluid outlets. The pneumatic gas can be supplied by a pump or other source of pressurized pneumatic gas. For example, an air pump can be positioned within the hydraulic manifold in the console or elsewhere in the hydraulic pressure circuit therein. In some embodiments, a pulsing valve is configured to open when a pressure threshold in the pneumatic gas is reached. The pulsing valve can produce a substantially square pneumatic gas wave. In some embodiments, the pressurized air output by the fluid outlets creates a squeegeeing effect wherein the pneumatic gas effectively squeegees the optical components to dry them.

Suction Cassette

Figure 12:
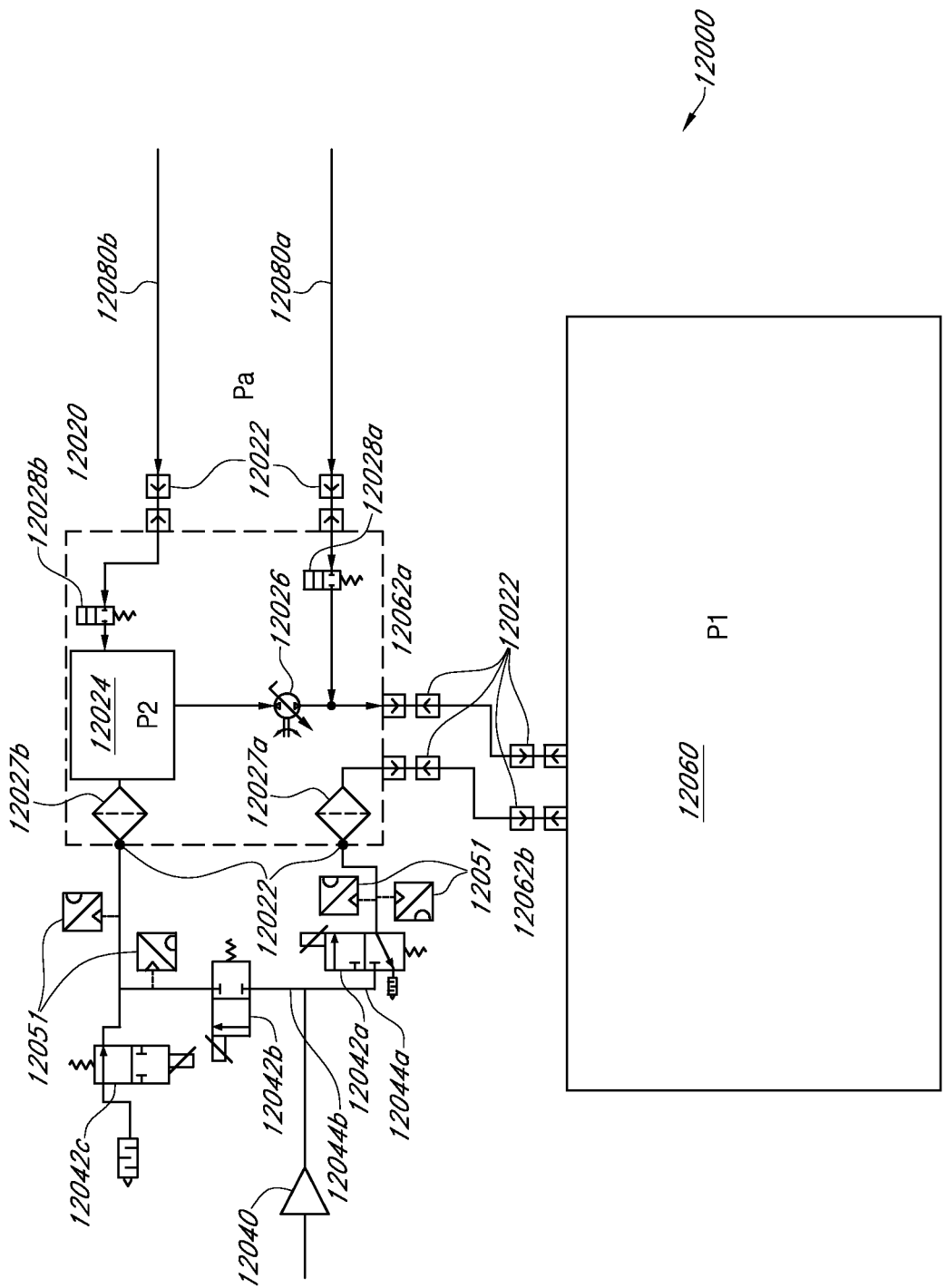
FIG. 12 is a schematic illustration of a medical suction system.

In some embodiments, a console can include a medical suction system. As illustrated in FIG. 12, for example, a medical suction system 12000 can include a suction cassette assembly 12020. In some embodiments, the suction cassette assembly 12020 and/or components thereof are disposable. The suction cassette assembly 12020 can include a plurality of ports 12022. The ports 12022 can be configured to facilitate fluid communication between fluid lines external to the suction cassette assembly 12020 and fluid lines internal to the suction cassette assembly 12020.

In some embodiments, the medical suction system 12000 includes a first suction line 12080a. The medical suction system 12000 can, in some embodiments, include a second suction line 12080b. The suction cassette assembly 12020 can be configured to utilize the first and second suction lines 12080a, 12080b simultaneously and/or in isolation.

As illustrated, the medical suction system 12000 can include a vacuum source 12040. In some embodiments, the vacuum source 12040 is a hospital vacuum source. In some embodiments, the vacuum source 12040 is a pump. Many variations are possible. In some embodiments, the vacuum source 12040 is fluidly connected to the suction cassette assembly 12020 via a first vacuum line 12044a. In some embodiments, a second vacuum line 12044b connects the vacuum source 12040 to the suction cassette 12020. The medical suction system 12000 can be configured to utilize the first and second vacuum lines 12044a, 12044b simultaneously and/or in isolation.

In some embodiments, the medical suction system 12000 includes a storage tank 12060. The storage tank 12060 can be configured to store blood and/or other tissue/fluids. In some embodiments, the storage tank 12060 is fluidly connected to a waste line (not shown) or other disposal line. The storage tank 12060 can be connected to the suction cassette assembly 12020 via a first storage line (e.g., storage inlet line 12062a). In some embodiments, the storage tank 12060 is connected to the suction cassette assembly 12020 via a second storage line (e.g., storage outlet line 12062b).

The suction cassette assembly 12020 can include an intermediate tank 12024. The intermediate tank 12024 can be housed at least partially within the suction cassette assembly 12020. In some embodiments, the intermediate storage tank 12024 is fluidly connected to the second suction line 12080b. The intermediate storage tank 12024 can be configured to store medical and/or bodily fluids/tissues (e.g., blood, saline, bone matter).

In some embodiments, the intermediate storage tank 12024 is fluidly connected to the storage tank 12060. In some embodiments, a pump 12026 (e.g., a peristaltic pump or other fluid pump) can be positioned on the fluid line between the intermediate storage tank 12024 and the storage tank 12060. The pump 12026 can be configured to pull material from the intermediate storage tank 12024 into the storage tank 12060. In some embodiments, the pump 12026 is configured to reduce the likelihood of fluid/bodily material transfer from the storage tank 12060 to the intermediate storage tank 12024. The pump 12026 can be configured to permit large portions of tissue (e.g., bone portions, muscle portions, and/or other tissue) to travel from the intermediate storage tank 12024 to the storage tank 12060. In some embodiments, the pump 12026 is positioned at least partially within the suction cassette assembly 12020.

The medical suction system 12000 can include one or more filters 12022. In some embodiments, the filters 12027a, 12027b are hydrophobic and/or anti-microbial. One or more of the filters 12022 can be positioned within the suction cassette assembly 12020. In some embodiments, a filter 12022 is positioned in the fluid line between the storage tank 12060 and the vacuum source 12040. Such a filter 12022 could be configured to reduce the likelihood that liquid and/or pathogens could pass from the storage tank 12060 to the vacuum source 12040. In some embodiments a filter 12022 can be positioned in the fluid line between the intermediate storage tank 12024 and the vacuum source 12040. Such a filter 12022 could be configured to reduce the likelihood that liquid and/or pathogens could pass from the intermediate storage tank 12024 to the vacuum source 12040.

In some embodiments, one or more valves are positioned on the vacuum lines 12044a, 12044b. For example, a first vacuum valve 12042a can be positioned on the first vacuum line 12044a. The first vacuum valve 12042a can be configured to selectively occlude the first vacuum line 12044a. A filter 12027a can be positioned in the first vacuum line 12044a. For example, the filter 12027a can be positioned at least partially within the suction cassette assembly 12020, as illustrated in FIG. 12. In some embodiments, the filter 12027a is an antimicrobial and/or hydrophobic filter. The filter 12027a can be configured to reduce the likelihood that blood or other material from the storage tank 12060 will pass into the first vacuum valve 12042a and/or into the vacuum source 12040.

A second vacuum valve 12042b can be positioned on the second vacuum line 12044b. In some embodiments, the second vacuum valve 12042b is configured to selectively occlude the second vacuum line 12044b. A filter 12027b can be positioned in the second vacuum line 12044b. For example, the filter 12027b can be positioned at least partially within the suction cassette assembly 12020. In some embodiments, the filter 12027b is an antimicrobial and/or hydrophobic filter. The filter 12027a can be configured to reduce the likelihood that blood or other materials from the intermediate storage tank 12024 will pass into the second vacuum valve 12042b and/or into the vacuum source 12040. In some embodiments, the intermediate storage tank 12024 includes a baffle (not shown) or other structure to reduce the likelihood of material ingress from the intermediate storage tank 12024 to the filter 12027b and/or to the second vacuum line 12044*b*. For example, the baffle help to block fluid from splashing directly from the second suction line 12080*b* to the second vacuum line 12044*b*.

In some embodiments, the medical suction system 12000 includes a third vacuum valve 12042*c*. The third vacuum valve 12042*c* can be positioned on the second vacuum line 12044*b*. In some embodiments, the third vacuum valve 12042*c* is fluidly connected to the second vacuum line 12044*b* between the intermediate storage tank 12024 and the second vacuum valve 12042*b*. The third vacuum valve 12042*c* can be used to moderate the pressure P2 within the intermediate storage tank 12024. For example, the third vacuum valve 12042*c* can be used to maintain the pressure P2 within the intermediate storage tank 12024 within a predetermined range (e.g., 0-550 mm Hg, 200-800 mm Hg, etc.). In some embodiments, one or more pneumatic indicators 12051 can be positioned on the vacuum lines 12044*a*, 12044*b*. The indicators 12051 can be configured to provide feedback on pneumatic parameters (e.g., pressure).

In some embodiments, the vacuum source 12040 is configured to decrease the pressure P1 within the storage tank 12060. For example, the first vacuum valve 12042*a* can be at least partially opened to allow for fluid communication between the vacuum source 12040 and the storage tank 12060. In some embodiments, the vacuum source 12040 is configured to maintain the pressure P1 within the storage tank 12060 below ambient pressure Pa. In some embodiments, the vacuum source 12040 maintains the pressure P1 within the storage tank 12060 at or near 600 mm Hg.

The medical suction system 12000 is configured to operate with a low flow suction input and/or with a high flow suction input. For example, the first suction line 12080*a* can be configured to operate as a high flow suction line. In some embodiments, the first suction line 12080*a* is used to produce high flow at a sight of interest to suction, for example, heavy bleeding. In some embodiments, the second suction line 12080*b* is configured to operate as a low flow suction line. For example, the second suction line 12080*b* can be used to identify and coagulate low flow bleeding on the surface of the brain without damaging the brain.

In some embodiments, valves 12028*a*, 12028*b* (e.g., proportional elastomeric valves) can be positioned on the suction lines 12080*a*, 12080*b*, respectively. For example, valves 12028*a*, 12028*b* can be used to open and/or close fluid communication between the first suction line 12080*a* and the storage tank 12060 and to open and/or close fluid communication between the second suction line 12008*b* and the intermediate storage tank 12024, respectively.

Pneumatic Drive System

Figure 13:
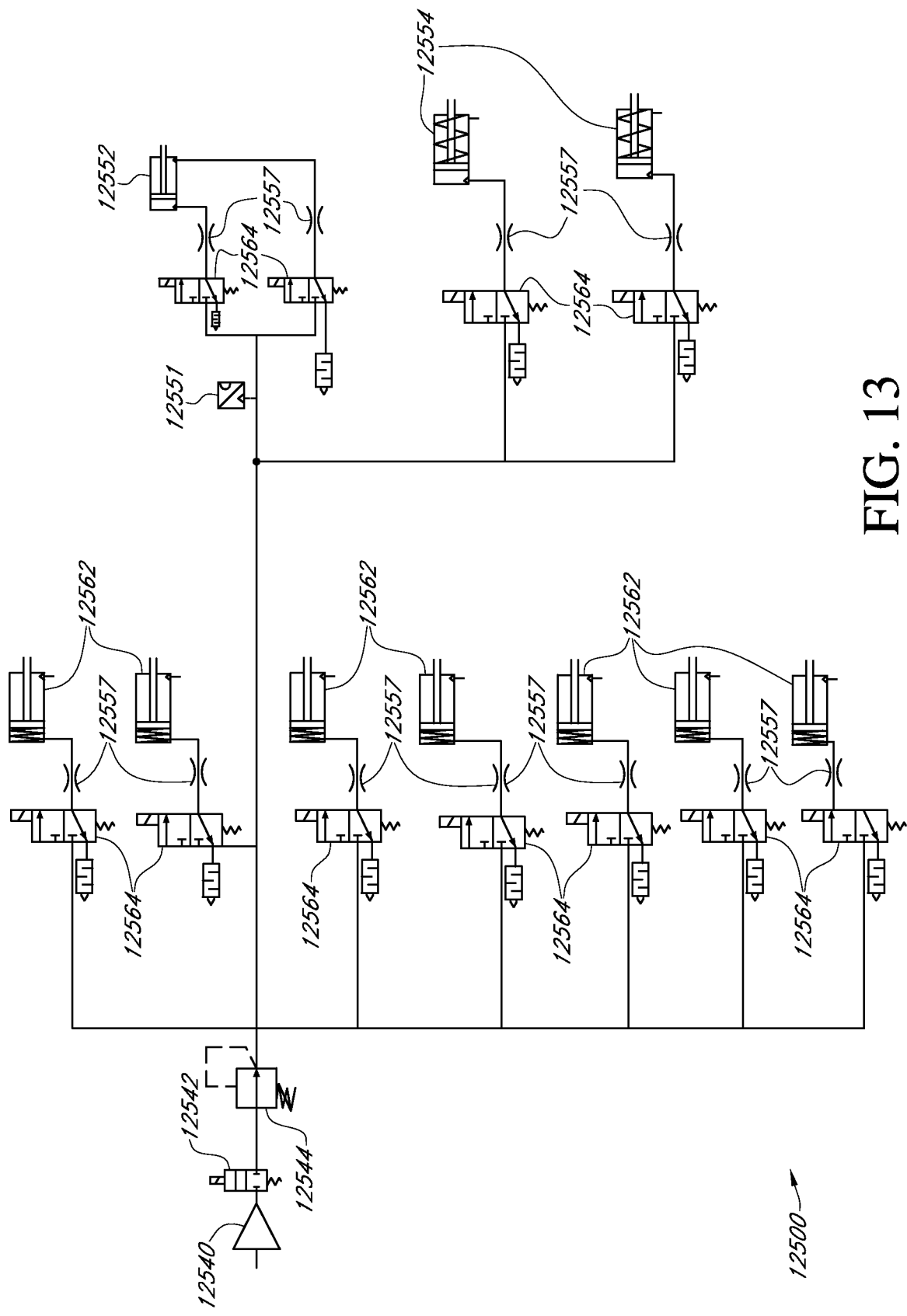
FIG. 13 is a schematic illustration of a pneumatic actuator circuit.

FIG. 13 illustrates a pneumatic drive system 12500. The pneumatic drive assembly can include a pneumatic pressure source 12540 (e.g., a hospital compressed gas system). In some embodiments, the pneumatic pressure source 12540 is fluidly connected to one or more pneumatic actuators 12552, 12554, 12562 (e.g., solenoids, pistons). One or more valves 12564 (e.g., elastomeric proportional and/or venting valves) can be positioned on the fluid lines between the pneumatic pressure source 12540 and the one or more pneumatic actuators 12552, 12562.

In some embodiments, the pneumatic actuators 12562 are configured to operate the valves of a hydraulic pressure circuit 3200 (and/or the valves of any of the embodiments of the hydraulic pressure circuits disclosed herein). In some embodiments, the actuator 12552 is configured to operate a cassette lifter. The pneumatic actuators 12554 can be configured to operate as tube ejectors for peristaltic pumps used, for example, in the hydraulic pressure circuits disclosed herein.

As illustrated in FIG. 13, the pneumatic drive system 12500 can include a safety valve 12542 and/or a pressure regulator 12544 (e.g., a 75 psi pressure regulator) positioned on the fluid line between the pneumatic pressure source 12540 and the actuators 12562, 12552, 12554. One or more pneumatic indicators 12551 can be positioned on the fluid lines of the pneumatic drive system 12500. In some embodiments, one or more restrictions 12557 can be applied to the fluid lines between the valves 12564 and the actuators 12552, 12554, 12562.

Apparatus for Moving a Component

Figure 14A:
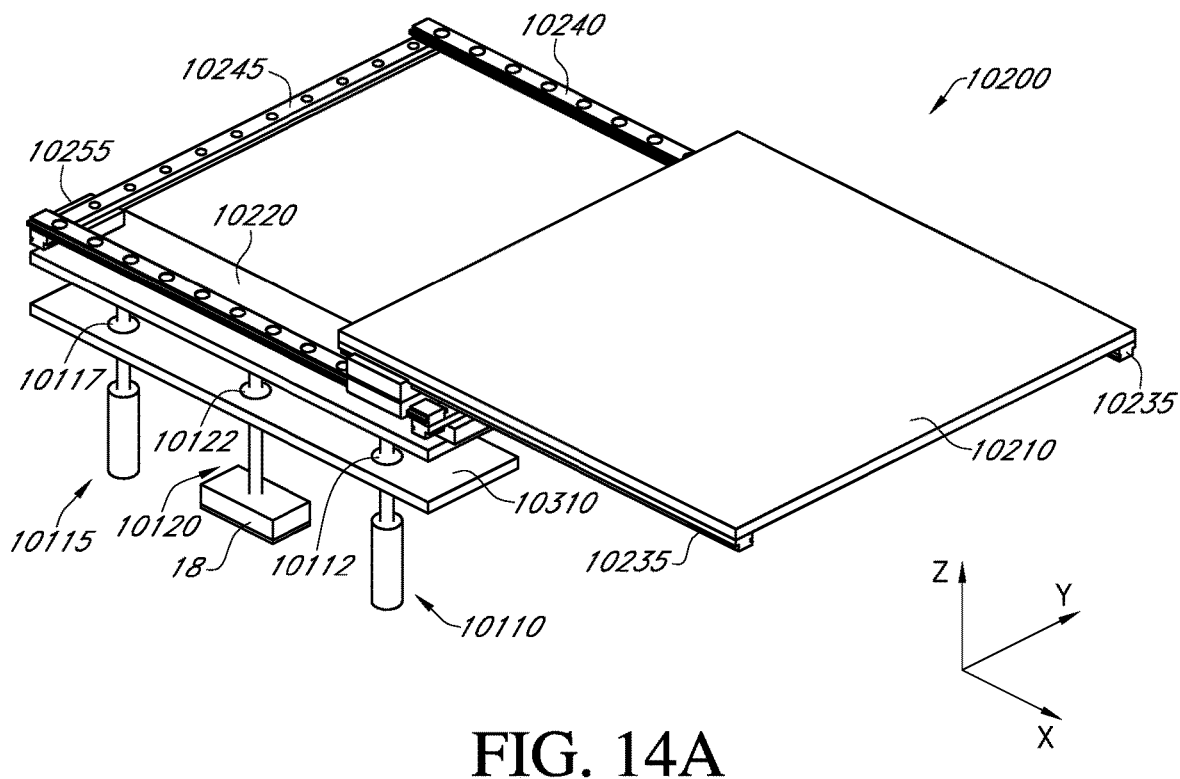
FIG. 14A is a perspective view of an embodiment of an apparatus having a translation system and a pitch-yaw adjustment system.
Figure 14B:
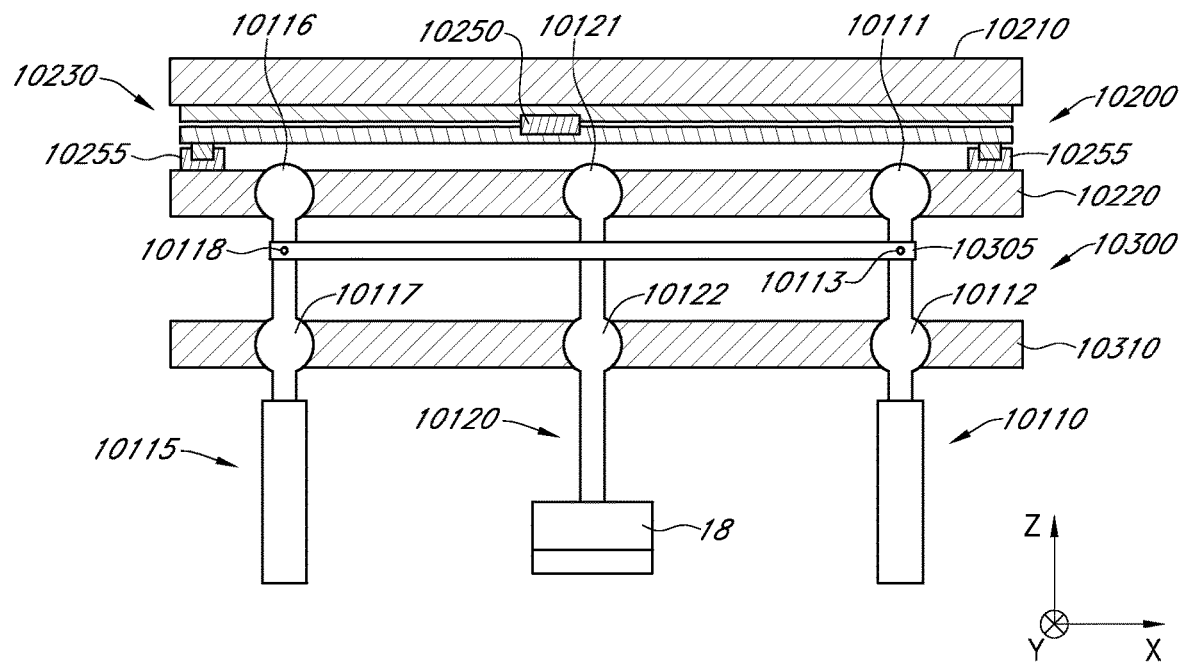
FIG. 14B is a partial section view of the apparatus of FIG. 14A.
Figure 15:
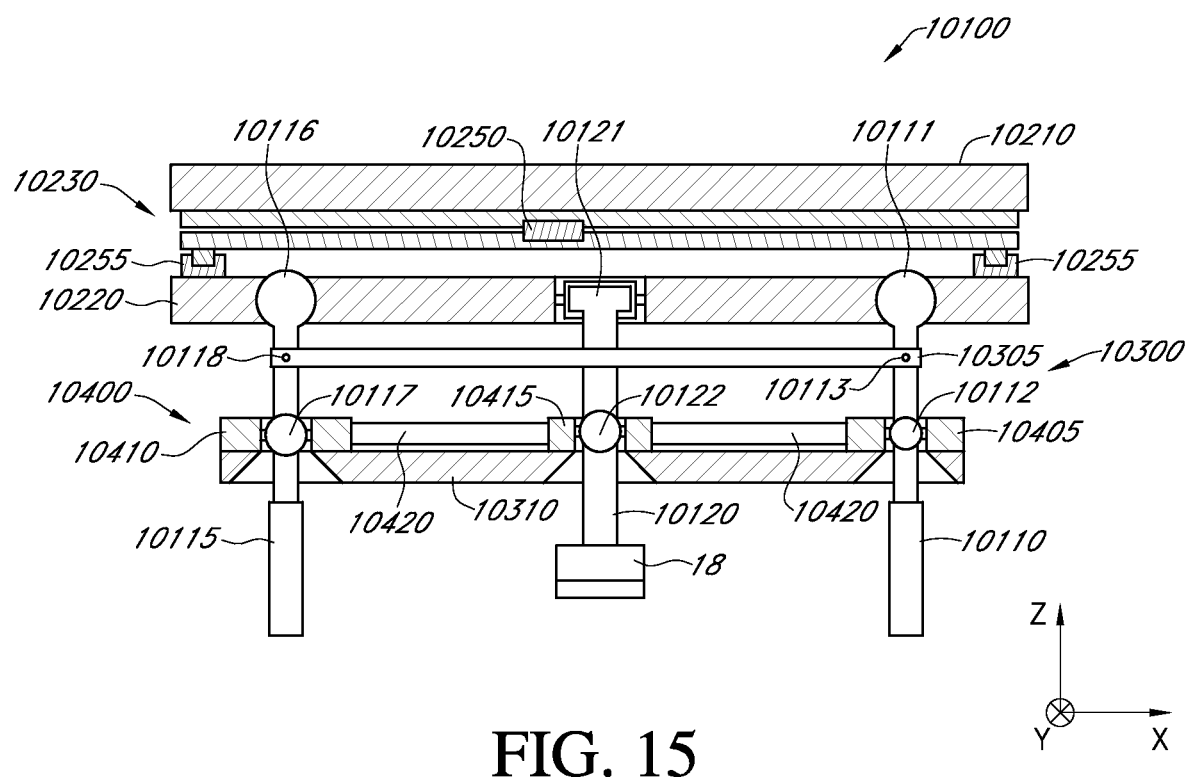
FIG. 15 is a partial section view of an embodiment of an apparatus having a translation system, a pitch-yaw adjustment system, and a z-distance adjustment system.

FIGS. 14A-19B illustrate embodiments of an apparatus 10100 that can be configured to allow a user to control the movement of one or more components 18. With reference to FIG. 14A-15, a translation system 10200 can have an upper connecting member 10210, a lower connecting member 10220, and a guide assembly 10230 located therebetween. The upper connecting member 10210 and the lower connecting member 10220 can be attached to the guide assembly 10230. The guide assembly 10230 can be designed to allow the lower connecting member 10220 to translate with respect to the upper connecting member 10210. The lower connecting member 10220 can be attached to control members 10110, 10115 and component arm 10120.

As illustrated in FIG. 14A, the guide assembly 10230 can include multiple guides in the form of tracks, rails, or similar structures. In the illustrated embodiment, the guides come in pairs. This can advantageously increase the stability of the translation system 10200. In other embodiments, the guides can be single members or multiple (e.g., greater than two) members. In some embodiments, the guide assembly 10230 can include an upper guide 10235, an x-axis intermediate guide 10240, and a y-axis intermediate guide 10245. Additionally, in some embodiments, the guide assembly 10230 can include a lower guide (not shown). The x-axis intermediate guide 10240 is oriented along the x-axis thereby allowing translation along the x-axis and the y-axis intermediate guide 10245 is oriented along the y-axis thereby allowing translation along the y-axis. The upper guide 10235 can be directly attached to the upper connecting member 10210, such as a bottom surface, and oriented along the x-axis. In some embodiments, the lower guide can be directly attached to the lower connecting member 10220, such as on a top surface, and oriented along the y-axis. The illustrated configuration can be used to allow the translation system 10200 to translate along the x-y plane. As should be apparent to one of ordinary skill in the art, the guide assembly 10230 can include additional guides along other axes or curvilinear guides. Furthermore, in some embodiments, multiple intermediate guides along the same axis can be used to advantageously increase the range of motion along that axis (e.g., via telescoping) without increasing the length of the guides along that axis. This can be especially beneficial in instances where a compact form factor is desired.

The guide assembly 10230 can include multiple guide connectors 10250, 10255 which can be used to connect the multiple components of the guide assembly 10230 together. In the illustrated embodiment, the guide connectors come in pairs although in other embodiments, single guide connectors or multiple (e.g., greater than two) guide connectors can be used. These guide connectors 10250, 10255 can be designed to translate along the path of the guides. As such, in embodiments using tracks or rails as guides, the connectors 10250, 10255 can be slidably translatable along the tracks or rails and can include mechanisms such as rollers, ball bearings, or the like. During operation of the illustrated embodiment, the guide assembly 10230 can be translated relative to the upper connecting member 10210 via sliding across both the upper guide 10235 and the x-axis intermediate guide 10240. The lower connecting member 10220 can thus translate relative to upper connecting member 10210 along the x-axis. The lower connecting member 10220 can be translated relative to the guide assembly 10230 by sliding across the y-axis intermediate guide 10245.

With continued reference to FIG. 14A, as illustrated in the embodiment contained therein, the upper connecting member 10210 can be larger than the lower connecting member 10220. The range of translation along the x-axis can be greater than the range of translation along the y-axis. In the illustrated embodiment, the range of translation along the x-axis is approximately ±175 mm and the range of translation along the y-axis is approximately ±87.5 mm. Additionally, in some embodiments, the lower connecting member 10220 does not extend beyond the upper connecting member 10210 along the y-axis. In other embodiments, the lower connecting member 10220 can extend beyond the upper connecting member 10210 along the y-axis if desired for an extended range of motion.

The lower connection member 10220 can be translated relative to the upper connection member 10210 by translating the control members 10110, 10115. As described above, in various embodiments, the joints 10111, 10116 can be any joint that lacks translational degrees of freedom along at least the x-axis and the y-axis. As such, a user of the translation system 10200 can move one control member such as control members 10110, 10115 in the desired direction to translate the lower connection member 10220 and ultimately the component 18 which can be attached thereto. Because movement of the component 18 is linked directly to the user's physical movement of the control member 10110, 10115, dexterous users can find this type of mechanism more user-friendly and precise. Furthermore, in embodiments where the joints 10111, 10116 lack translation degrees of freedom along at least the x-axis and the y-axis, the other control member, such as control members 10110 or 10115, also translate along with the lower connection member 10220. As such, a user can control translation using any control member attached to the lower connection member 10220.

In some embodiments, the guide connectors 10550, 10555 can be designed to have a threshold friction such that the lower connection member 10220 can only translate upon a threshold force being applied to the lower connection member 10220. Requiring a threshold force to be applied prior to movement can reduce the likelihood of unintentional movement of the translation system 10200 is reduced. In some embodiments, alternative control mechanisms can be used in conjunction with, or in lieu of, the control members 10110, 10115.

With reference to FIGS. 14A-B and 16A-D, as shown in the illustrated embodiment, the apparatus 10100 includes a pitch-yaw adjustment system 10300. The pitch-yaw adjustment system 10300 can include member 10310 which can connect two or more control members 10110, 10115. As described in part above, the member 10310 can be connected to the two or more control members 10110, 10115 and the component arm 10120 via joints 10112, 10117, 10122 having two or more rotational degrees of freedom, such as a ball-and-socket joint. As should be apparent to one of ordinary skill in the art, other types of joints having a greater or fewer rotational degrees of freedom can be used.

The member 10310 can be configured to link the motion of multiple control members 10110, 10115 and the component arm 10120. For example, in the illustrated embodiment, when adjusting the yaw of one control member 10110, the yaw of the other control member 10115 and component arm 10120 correspondingly adjusts via mechanical movement. In much the same way, in the illustrated embodiment, when adjusting the pitch of one control member 10110, the pitch of the other control member 10115 and component arm 10120 also correspondingly adjusts. This provides the advantage of allowing a user of the pitch-yaw adjustment system 10300 to adjust pitch or yaw of the component arm 10120, and ultimately the component 18, using only one of potentially multiple control members such as control members 10110 or 10115 in the illustrated embodiment. A user may advantageously choose whichever control member 10110, 10115 is most convenient to use at the time an adjustment is necessary. Additionally, this may facilitate use by multiple users. For example, during a medical procedure, a medical professional on one side may use one control member 10110. If a second medical professional or assistant needs to make an adjustment, the second medical professional or assistant may use the other control member 10115 if more readily accessible.

Figure 16A:
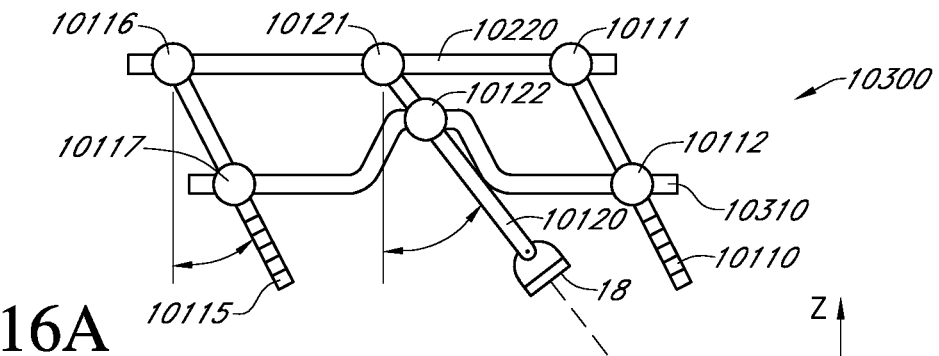
FIG. 16A is a front view of an embodiment of a pitch-yaw adjustment system having greater than a one-to-one adjustment ratio.
Figure 16B:
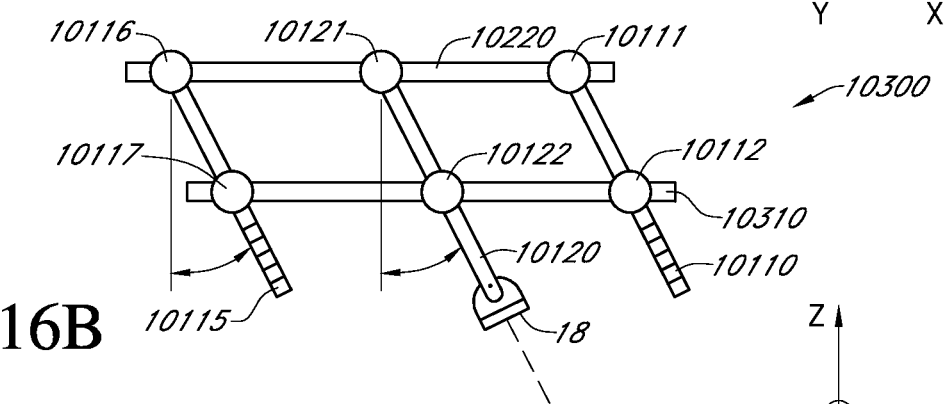
FIG. 16B is a front view of an embodiment of a pitch-yaw adjustment system having a one-to-one adjustment ratio.
Figure 16C:
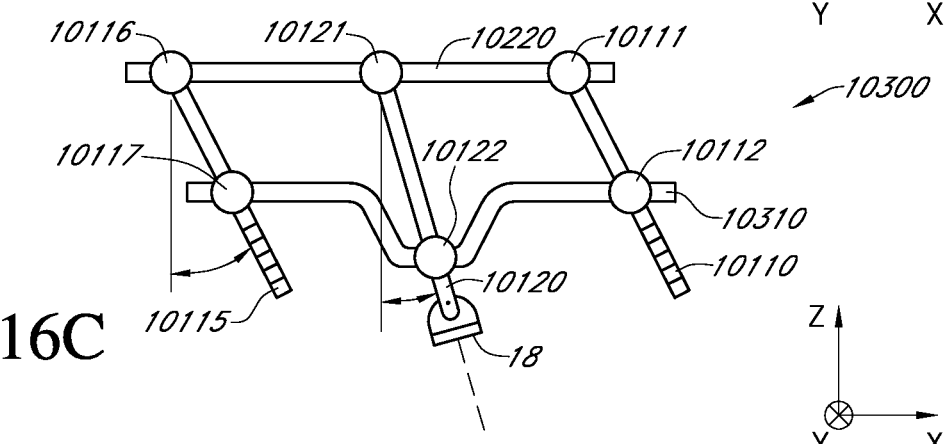
FIG. 16C is a front view of an embodiment of a pitch-yaw adjustment system having less than a one-to-one adjustment ratio.
Figure 16D:
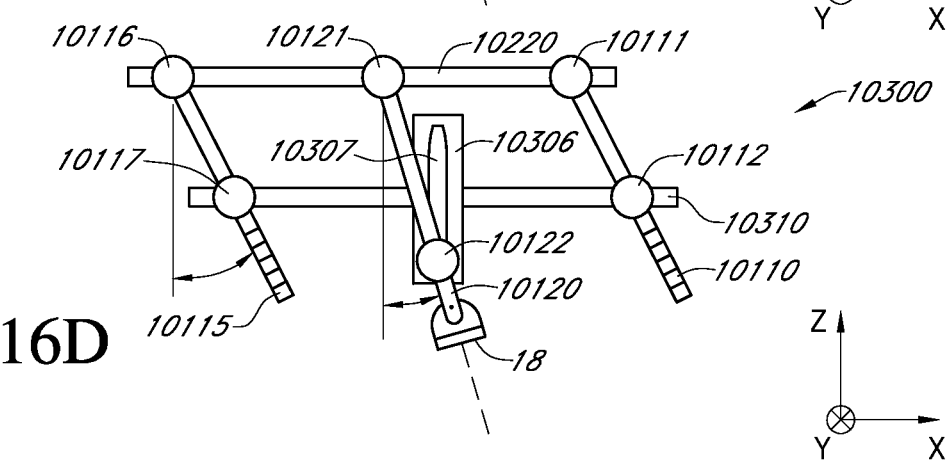
FIG. 16D is a front view of an embodiment of a pitch-yaw adjustment system having a variable adjustment ratio.

In some embodiments, the member 10310 can be attached to the control members 10110, 10115 and the component arm 10120 such that adjustment of yaw and/or pitch of the control members 10110, 10115 can result in more than or less than a one-to-one adjustment in the yaw or pitch of the component arm 10120. For example, as illustrated in FIG. 16A, the distance between the joints 10111, 10112 of the first control member 10110 and the distance between the joints 10116, 10117 of the second control member 10115 is greater than the distance between the joints 10121, 10122 of the component arm 10120. This can result in greater than a one-to-one adjustment in the yaw of the component arm 10120. The member 10310 shown in FIGS. 16B and 16C can result in a one-to-one and less than one-to-one adjustment in the yaw of the component arm 10120 respectively. For example, as illustrated in FIG. 16C, the distance between the joints 10111, 10112 of the first control member 10110 and the distance between the joints 10116, 10117 of the second control member 10115 is less than the distance between the joints 10121, 10122 of the component arm 10120. In some embodiments, the pitch-yaw adjustment system 10300 can be adjustable such that the user may choose whether to use a one-to-one adjustment ratio, greater than a one-to-one ratio, or less than a one-to-one ratio. For example, as illustrated in FIG. 16D, the member 10310 can include a plate 10306 having a slot 10307 in which the joint 10122 of the component arm 10120 can be adjusted vertically to adjust the joint connection points thereby adjusting the ratio. Other types of adjustment mechanisms can be used such as multiple apertures vertically arranged as well as other mechanisms known in the art.

In some embodiments, a link member 10305 can also be used. The link member 10305 can be designed to attach to the control members 10110 and 10115 to provide greater structural rigidity. For example, link member 10305 can be connected to control members 10110 and 10115 using joints having fewer degrees of freedom. For example, the link member 10305 can be attached to control member 10110 at joint 10113 and attached to control member 10115 at joint 10118. In some embodiments, the joint can have a single degree of rotational freedom such as a pin-and-aperture design. By limiting the degrees of freedom, the control members 10110 and 10115 can be more likely to remain co-planar when rotating in pitch and/or yaw thereby reducing the potential for twisting. In some embodiments, the link member 10305 can be used in lieu of member 10310.

In some embodiments, such as that illustrated in FIG. 15, transmitting drive members 10405, 10410 and receiving drive member 10415 (shown in FIG. 19A) can be arranged as shown in FIGS. 16A-16D to link the control member 10110, 10115 to the component arm 10120 and vary the adjustment ratio. Additionally, in some embodiments, other means of adjusting the pitch and/or yaw may be included.

With reference to FIG. 15, an embodiment of the apparatus 10100 is shown which includes a translation control system 10200, pitch/yaw adjustment system 10300, and a z-distance adjustment system 10400. This embodiment shares some general characteristics with the embodiment of FIG. 14A-B with modifications made to accommodate the z-distance adjustment system 10400. For example, joints 10112, 10117, and 10122 can be capstans which allow these joints to be operably coupled to the z-distance adjustment system 10400. In some embodiments, the z-distance adjustment system 10400 can include a drive assembly 10401.

Figure 19A:
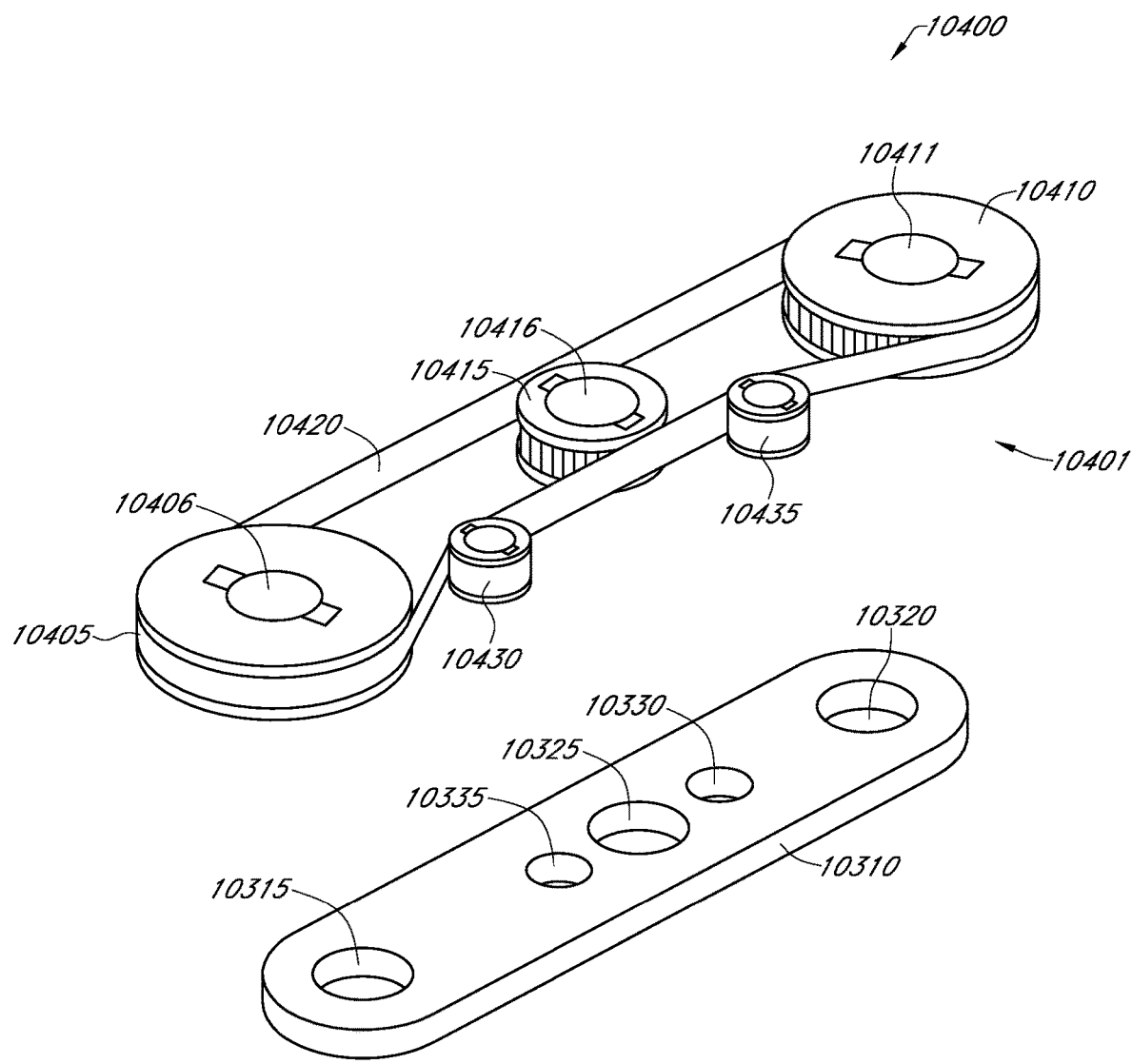
FIG. 19A is a perspective view of an embodiment of a z-distance adjustment system.
Figure 19B:
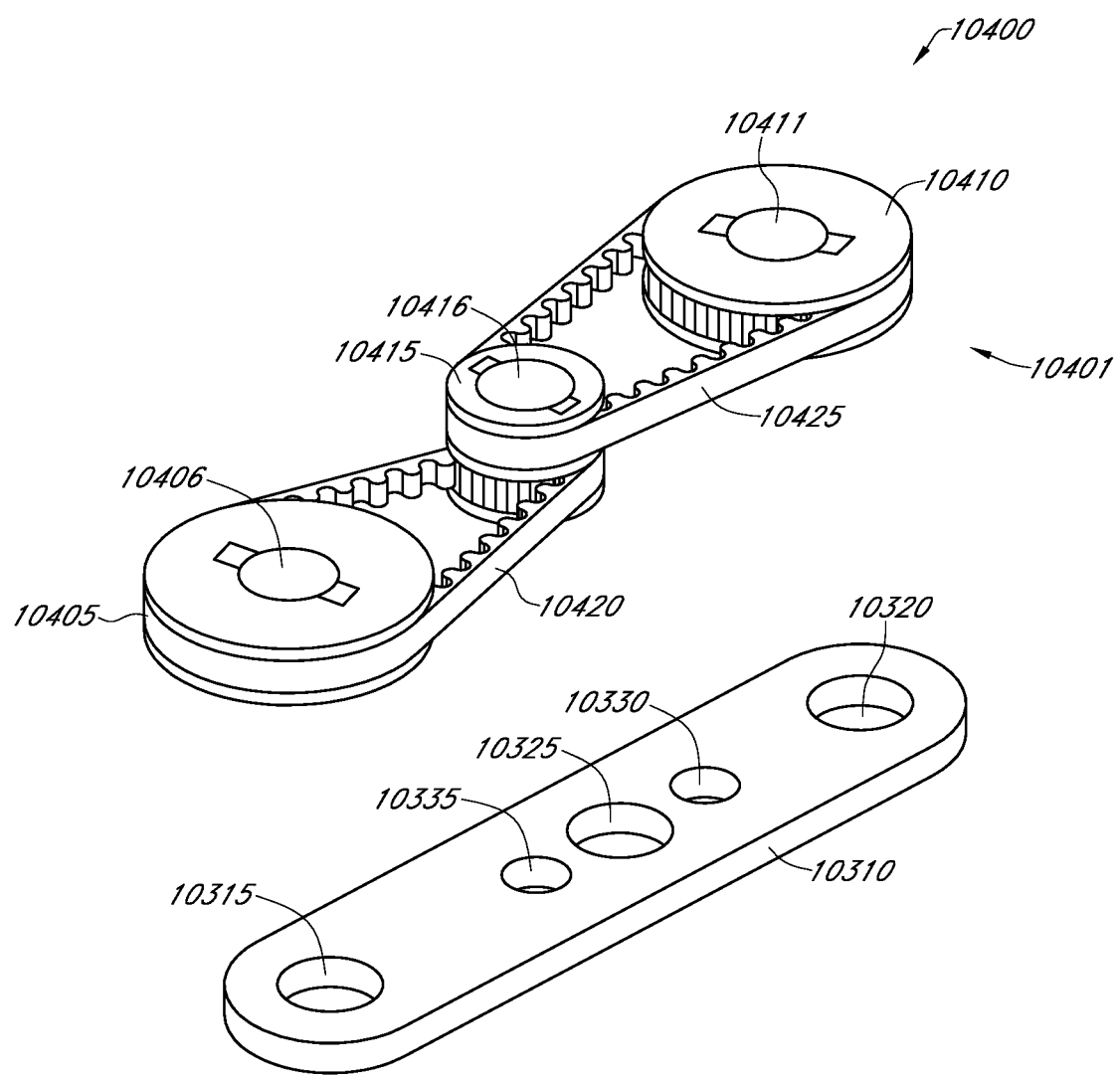
FIG. 19B is a perspective view of an embodiment of a z-distance adjustment system.

As illustrated in FIGS. 15 and 19A-B, the drive assembly 10401 can include multiple transmitting drive members 10405, 10410 attached to the control members 10110, 10115 respectively being disposed in and connected to apertures 10406, 10411 via joints 10112, 10117 respectively, receiving drive member 10415 attached to the component arm 10120 in aperture 10416 via joint 10122, and transmission member, such as cable 10420, designed to transmit torque from the transmitting drive members 10405, 10410 to the receiving drive members 10415. The cable 10420 can be tensioned on receiving drive member 10415 using cable tensioners 10430, 10435. The drive members 10405, 10410, 10415 can be centered along apertures 10315, 10320, 10325 respectively of the member, such as support member 10310. The cable tensioners 10430 and 10435 can be centered along apertures 10330 and 10335 of member 10310 respectively. In some embodiments, such as shown in FIG. 19B, a toothed belt can be used with corresponding gears. Additionally, in some embodiments, such as illustrated in FIG. 19B, two transmissions members 10420 and 10425 can be used to connect the drive members. As should be apparent to one of ordinary skill in the art, separate cables, with or without tensioners, or any other transmission members can be used. Additionally, other drive member designs, such as crown gears which can be used with transmission shafts having beveled gears, can also be used.

Figure 17:
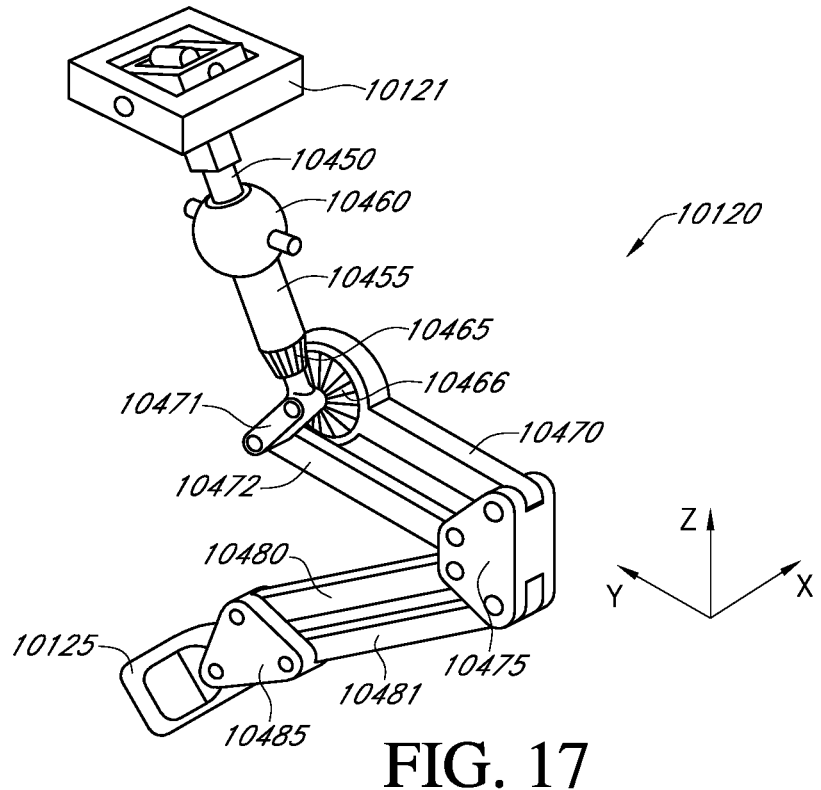
FIG. 17 is a perspective view of an embodiment of an arm for a component.
Figure 18:
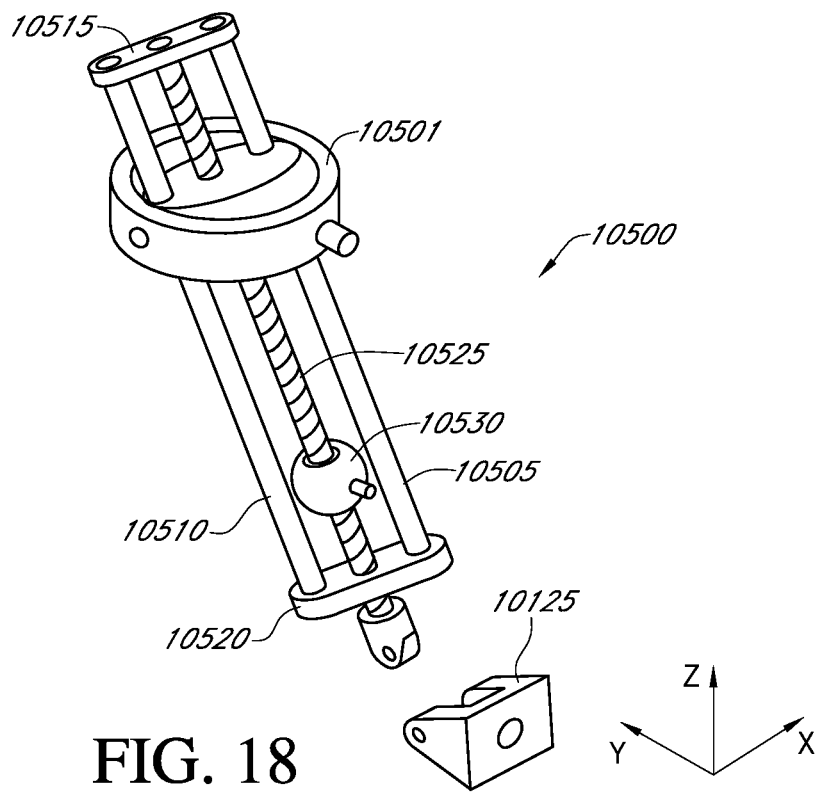
FIG. 18 is a perspective view of an embodiment of an arm for a component.

As shown in FIGS. 17 and 18, in one embodiment, the component arm 10120 can comprise a four-bar linkage assembly for adjusting the z-distance. In this embodiment, the component arm 10120 can include a shaft 10450 attached to the joint 10121 and a sleeve 10455 over the shaft 10450 which is rotatable around the longitudinal axis of the shaft 10450. The sleeve 10455 can include a torque receiving joint 10460, such as the illustrated capstan, at one end which can be received within aperture 10416 (see FIG. 19A-B) of the receiving drive member 10415, such as the illustrated keyed aperture, to receive a torque to rotate the sleeve 10455. The sleeve 10455 can include a first rotation redirecting member 10465, such as the illustrated bevel gear, at a second end which can interact with a second rotation redirecting member 10466, such as the illustrated corresponding bevel gear, on an end of a driven link 10470 of the four-bar linkage assembly. As such, rotation of the sleeve 10455 can result in rotation of the driven link 10470 around a different axis. Rotation of the driven link 10470 can result in vertical movement of the arm.

In some embodiments, the four-bar linkage assembly may include, in addition to a driven link 10470, a shaft link 10471 which can be rigidly attached to the shaft 10450, a free link 10472, and a hinge unit 10475. In some embodiments, a second four-bar linkage assembly can be included with a second free link 10480 and third free link 10481, a hinge unit 10475 attached to the first four-bar linkage assembly, and a second hinge unit 10485 for attaching the component 18 to the component arm 10120. In such embodiments, mechanisms may be added between the first four-bar linkage assembly and the second four-bar linkage assembly such that the second four-bar linkage assembly will correspondingly rotate when the driven link 10470 is rotated. For example, the first free link 10472 and the second free link 10480 can be rotatably connected via gearing. The gearing can be chosen such that there is a one-to-one rotational transfer between the first free link 10472 and the second free link 10480. In other embodiments, the gearing can be chosen such that there is greater than a one-to-one rotational transfer or lesser than a one-to-one rotational transfer. As should be appreciated by one of ordinary skill in the art, the lengths of the links and the ratio of the gearing can be chosen such that the z-distance adjustment system 10400 can adjust the z-distance, that is, adjust the position of the component 18 in a direction generally parallel to the z-axis, without causing any or at least a small amount of translation of the component in either the x-axis or y-axis.

The four-bar linkage component arm 10120 provides the advantage of reducing the form factor when the z-distance is greater. Due to the compact form factor of the four-bar linkage component arm 10120, the component 18 can be placed closer to the lower connecting member 10220.

In other embodiments, the component arm 10500 can include a screw-drive assembly for adjusting the z-distance. In this embodiment, the component arm 10500 can include two struts members 10505, 10510 designed to support the component arm 10500 rigidly attached to a first end 10515 and second end 10520, a screw member 10525 rigidly attached to the first end 10515, the second end 10520 and the component 18, and a threaded torque receiving joint 10530, such as the illustrated capstan, at one end which can be received within aperture 10416 (see FIG. 19A-B) of the receiving drive member 10415, such as the illustrated keyed aperture, to receive a torque to rotate the torque receiving joint 10530 (in some embodiments, torque receiving joint 10530 can also be the joint 10122 such as shown in FIG. 15). In some embodiments, the torque receiving joint 10530 can be supported by the receiving drive member 10415. Furthermore, in some embodiments, the two strut members 10505, 10510 and the screw member 10525 may freely translate through the joint 10501. In this embodiment, because torque receiving joint 10530 is threaded and screw member 10525 is rotationally fixed along the z-axis due to joint 10501 having only two degrees of rotational freedom, rotation of the torque receiving joint 10530 can result in translation of the component 18 in a direction along the length of screw member 10525 (e.g., the z-axis) via the screw member 10525. As should be appreciated by one of skill in the art, the pitch of the threaded torque receiving joint 10530 and the screw member 10525 can be chosen to determine the amount of translation per revolution of the joint 10530. Increasing the pitch can result in greater z-distance adjustment per revolution whereas decreased pitch can result in lesser z-distance adjustment per revolution.

The z-distance adjustment system 10400 can be operated by using the control members 10110, 10115. In the illustrated embodiment, control member 10110 can be rotatably coupled to transmitting drive member 10405 via aperture 10406, such as the illustrated keyed aperture, and control member 10115 can be rotatably coupled to transmitting drive member 10410 via aperture 10411. In some embodiments, the rotatable coupling can be achieved through use of a capstan, such as 10112 and 10117 of FIG. 15, which can be similar to the torque receiving joint 10460, 10530 of the component arm 10120, 10500 shown in FIGS. 17 and 18. As such, rotation of either control member around the z-axis results in rotation of the respective transmitting member. In some embodiments, since the transmitting drive members 10405, 10410 and receiving drive member 10415 can be physically coupled via transmission members 10420 such as a cable, toothed belt or similar apparatus, rotation of one control member can result in rotation of any other attached control member and component arm. As such, this provides the advantage of allowing the z-distance adjustment system 10400 to be operated using only a single control member.

As should be apparent to one of ordinary skill in the art, the radius of the transmitting drive members 10405, 10410 and receiving drive member 10415 can be chosen to modify the speed of the z-distance adjustment. For example, in some embodiments, the transmitting drive members 10405, 10410 can have a larger radius than the receiving drive member 10415 such that, for a single revolution of a control member 10110, 10115, the receiving drive member 10415 rotates more than one revolution.

Various embodiments may comprise a retractor, use a retractor, or are configured to be used with a retractor and not an endoscope, laparoscope, or arthroscope. Similarly, many embodiments comprise retractors or use retractors or are configured to be used with retractors wherein cameras are disposed on the retractors, not endoscope, laparoscope, or arthroscope.

In various embodiments the retractor fits in an opening in a manner to provide ample room for the surgeon to operate but does not provide a gas seal for pumping up a cavity as may a laparoscope. Similarly, in many embodiments the retractor does not maintain alignment of the layers of tissue that are cut through to form the incision.

In various embodiments, the retractor is not employed as a fulcrum for surgical tools.

In various embodiments the camera(s) can be positioned on top of the retractor near and above the body surface or on the retractor at a depth within the surgical site (e.g., at the far distal end of the retractor into the deepest portion of the surgical site, or elsewhere on the retractor such as more proximal).

Many embodiments are employed for spine surgery, neurosurgery, head and/or neck surgery, and ear nose and throat surgery and many embodiments involve the cutting and extraction of bone, for example, through the pathway provided by the retractor.

Various embodiments, however, may be used with devices other than retractors.

Many other embodiments are possible, including numerous combinations of the above recited features.

The embodiments described herein can differ from those specifically shown. For example, various elements of the different embodiments may be combined and/or rearranged. Components can be added, removed and/or rearranged. A wide variety of variations are possible.

CONCLUSION

Unless otherwise indicated, the functions described herein may be performed by software (e.g., including modules) including executable code and instructions running on one or more systems including one or more computers. The software may be stored in computer readable media (e.g., some or all of the following: optical media (e.g., CD-ROM, DVD, Blu-ray, etc.), magnetic media (e.g., fixed or removable magnetic media), semiconductor memory (e.g., RAM, ROM, Flash memory, EPROM, etc.), and/or other types of computer readable media.

The one or more computers can include one or more central processing units (CPUs) that execute program code and process data, non-transitory, tangible memory, including, for example, one or more of volatile memory, such as random access memory (RAM) for temporarily storing data and data structures during program execution, non-volatile memory, such as a hard disc drive, optical drive, or FLASH drive, for storing programs and data, including databases, a wired and/or wireless network interface for accessing an intranet and/or Internet, and/or other interfaces.

In addition, the computers can include a display for displaying user interfaces, data, and the like, and one or more user input devices, such as a keyboard, mouse, pointing device, touch screen, microphone and/or the like, used to navigate, provide commands, enter information, provide search queries, and/or the like. The systems described herein can also be implemented using general-purpose computers, special purpose computers, terminals, state machines, and/or hardwired electronic circuits.

Various embodiments provide for communications between one or more systems and one or more users. These user communications may be provided to a user terminal (e.g., an interactive television, a phone, a laptop/desktop computer, a device providing Internet access, or other networked device). For example, communications may be provided via Webpages, downloaded documents, email, SMS (short messaging service) message, MMS (multimedia messaging service) message, terminal vibrations, other forms of electronic communication, text-to-speech message, or otherwise.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single product or packaged into multiple products. Additionally, other embodiments are within the scope of the following claims. In some cases, the actions recited in the claims can be performed in a different order and still achieve desirable results.

What is claimed is:

1. A medical apparatus for use with a surgical tubular retractor configured to hold open an incision and thereby provide a pathway for access of surgical tools to a surgical site, the surgical retractor having a first end, a second end, and a longitudinal axis extending between the first and second ends, wherein the pathway extends along the longitudinal axis into the surgical site and the first end is more proximal than the second end, the apparatus comprising:
an imaging insert configured to be received within the tubular retractor, the imaging insert comprising a proximal end and a distal end, wherein the imaging insert is configured to extend along the longitudinal axis of the tubular retractor between the first and second ends of the tubular retractor without substantially obstructing the pathway and maintaining the pathway allowing the surgical tools to gain access to the surgical site through the proximal end of the imaging insert; and
wherein the imaging insert comprises:
a proximal head of the imaging insert at the proximal end, the proximal head configured to be disposed above the first end of the tubular retractor; and
a plurality of cameras facing radially inward toward the pathway; and
wherein the plurality of cameras are disposed on an inner surface of the imaging insert.

2. The medical apparatus of claim 1, wherein the imaging insert further comprises an illumination assembly disposed on the inner surface of the imaging insert.

3. The medical apparatus of claim 2, wherein the illumination assembly comprises at least one illumination source, the at least one illumination source comprising light guides or fibers.

4. The medical apparatus of claim 2, wherein the illumination assembly comprises at least one illumination source, the at least one illumination source configured to be longitudinally movable along a length of the imaging insert.

5. The medical apparatus of claim 1, wherein the imaging insert is substantially tubular and an outer surface of the imaging insert is configured to contact an inner surface of the tubular retractor.

6. The medical apparatus of claim 1, wherein the imaging insert comprises one or more pieces configured to be extending from the proximal head, and wherein an outer surface of the one or more a pieces is configured to contact an inner surface of the tubular retractor.

7. The medical apparatus of claim 1, wherein the imaging insert comprises one or more pieces configured to be disposed adjacent to one another, and wherein an outer surface of the one or more pieces is configured to contact an inner surface of the tubular retractor.

8. The medical apparatus of claim 1, wherein the imaging insert comprises one or more annular pieces configured to be disposed adjacent to one another to form a substantially tubular insert, and wherein an outer surface of the one or more annular pieces is configured to contact an inner surface of the tubular retractor.

9. The medical apparatus of claim 1, wherein the imaging insert comprises a restraint configured to prohibit the imaging insert from passing completely through the pathway of the tubular retractor.

10. The medical apparatus of claim 1, wherein the proximal head of the imaging insert is wider than a distal portion of the imaging insert to restrain the imaging insert from passing completely through the pathway of the tubular retractor.

11. The medical apparatus of claim 1, wherein the proximal end of the imaging insert abuts the first end of the tubular retractor and the distal end of the insert is configured to be aligned with the second end of the tubular retractor.

12. The medical apparatus of claim 1, wherein the imaging insert is configured to slidably engage with the tubular retractor.

13. The medical apparatus of claim 1, wherein the imaging insert comprises a ridge on an outer surface configured to correspond to a groove on an inner surface of the tubular retractor, wherein the groove is configured to receive the ridge and to allow the insert to be slidably engaged with the retractor.

14. The medical apparatus of claim 1, wherein the imaging insert comprises a groove on an outer surface configured to correspond to a ridge on an inner surface of the tubular retractor, wherein the groove is configured to receive the ridge and to allow the insert to be slidably engaged with the retractor.

15. The medical apparatus of claim 1, wherein at least one of the plurality of cameras is on a flexible cable that is configured to be moved between the proximal and distal end of the imaging insert.

16. The medical apparatus of claim 15, wherein the flexible cable is configured to be fed through a slot on the proximal head of the imaging insert, wherein the at least one of the plurality of cameras on the flexible cable is moved closer or further from the distal end as the flexible cable is raised and lowered within the imaging insert.

17. The medical apparatus of claim 1, further comprising a plurality of connectors on the proximal head of the imaging insert, wherein the plurality of connectors comprise an optical fiber input port, a fluid port, or an air port.

18. The medical apparatus of claim 1, wherein the imaging insert comprises one or more pieces, and wherein an outer surface of the one or more pieces does not cover substantially all of an inner surface of the tubular retractor.

19. The medical apparatus of claim 18, wherein the outer surface of the one or more pieces corresponds to less than ⅞ of the perimeter of the inner surface of the tubular retractor.

20. The medical apparatus of claim 19, wherein the outer surface of the one or more pieces corresponds to less than ¾ of the perimeter of the inner surface of the tubular retractor.

21. The medical apparatus of claim 20, wherein the outer surface of the one or more pieces corresponds to less than ½ of the perimeter of the inner surface of the tubular retractor.

22. The medical apparatus of claim 21, wherein the outer surface of the one or more pieces corresponds to at least ⅓ of the perimeter of the inner surface of the tubular retractor.

23. The medical apparatus of claim 20, wherein the outer surface of the one or more pieces corresponds to at least ⅓ of the perimeter of the inner surface of the tubular retractor.

24. The medical apparatus of claim 19, wherein the outer surface of the one or more pieces corresponds to at least ⅓ of the perimeter of the inner surface of the tubular retractor.

25. The medical apparatus of claim 1, wherein the plurality of cameras face one another.

* * * * *